US006927320B1

(12) United States Patent
Benfey et al.

(10) Patent No.: US 6,927,320 B1
(45) Date of Patent: Aug. 9, 2005

(54) SHORT-ROOT GENE, PROMOTER, AND USES THEREOF

(75) Inventors: Philip N. Benfey, New York, NY (US); Yrjo Helariutta, Helsinki (FI); Hidehiro Fukaki, Nara (JP); Keiji Nakajima, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/578,827

(22) Filed: May 24, 2000

(51) Int. Cl.$^7$ .......................... C12N 15/82; A01H 5/00

(52) U.S. Cl. ...................... 800/287; 800/300; 800/301; 800/302; 800/279; 800/284

(58) Field of Search ................................. 800/287, 300, 800/301, 302, 279, 284

(56) References Cited

U.S. PATENT DOCUMENTS

| | | |
|---|---|---|
| 5,023,179 A | 6/1991 | Lam et al. |
| 5,097,025 A | 3/1992 | Benfey et al. |
| 5,110,732 A | 5/1992 | Benfey et al. |
| 5,256,558 A | 10/1993 | Coruzzi et al. |
| 5,272,071 A | 12/1993 | Chappel |
| 5,545,806 A | 8/1996 | Lonberg et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |

OTHER PUBLICATIONS

Fiedler et al. A complex ensemble of cis–regulatory elements controls the expression of a Vicia faba non–storage seed protein gene. Plant Molecular Biology, 1993, vol. 22, pp. 669–679.*
Bevan et al. GenBank Accession No. AL035605, Mar. 4, 1999.*
Kim et al, "A 20 nucleotide upstream element is essential for the nopaline synthase (nos) promoter activity", 1994, Plant Molecular Biology vol. 24, pp. 105–117.*
Benfey et al, "The Cauliflower Mosaic Virus 35S Promoter: Combinatorial Regulation of Transcription in Plants" Nov. 1990, Science vol. 250, pp. 959–966.*
Bevan, et al, GenBank Accession No. AL035605, Mar. 1999.*
Helariutta et al., Database Accession No. AF233752 (2000).
Rounsley et al., Database Accession No. B97786 (1998).
Author Unknown, TrEMBL Accession No. Q9SN22 (2000).
Author Unknown, TrEMBL Accession No. Q9SZF7 (2000).
Martin, C., "Transcription Factors and the Manipulation of Plant Traits," *Current Opinion in Biotechnology*, 7(2):130–138 (1996).

Di Laurenzio et al., "The *SCARECROW* Gene Regulates and Asymmetric Cell Division That Is Essential for Generating the Radial Organization of the *Arabidopsis* Root," *Cell*, 86:423–433 (1996).
Nakajima et al., "Intercellular Movement of the Putative Transcription Factor SHR in Root Patterning," *Nature*, 413(6853):307–311 (2001).
Helariutta et al., "Towards the Molecular Cloning of the *SHORTROOT* Locus," *9th International Conference on Arabidopsis Research* Abstract No. 457 (Jun. 1998).
Aeschbacher et al., 1995, "The SABRE gene is required for normal cell expansion in *Arabidopsis*", Genes & Development 9: 330–340.
Aeschbacher et al., 1994, "The Genetic and Molecular Basis of Root Development," Annual Review of Plant Physiology and Plant Molecular Biology 45: 25–45.
Aeschbacher and Benfey, 1992, "Genes that regulate plant development," Plant Science 83: 115–126.
Aryan et al., 1991, "Structural and functional analysis of promoter from gliadin, and endosperm–specific storage protein gene of *Triticum aestivum* L.", Mol. Gen. Genet. 225–65–71.
Barlow, 1995, "Gravity perception in plants: a multiplicity of systems derived by evolution?," Plant Cell Environ. 18:951–962.
Benfey and Scheres, 2000, "Root Development Primer," Current Biology 10: R813–815.
Benfey, 1999, "Is the shoot a root with a view?" Current Opinion in Plant Biology 2: 39–43.
Benfey and Schiefelbein, 1994, "Insights Into root development from *Arabidopsis* root mutants," Plant, Cell and Environment 17: 675–680.
Benfey and Schiefelbein, 1994, "Getting to the root of plant development: the genetics of *Arabidopsis* root formation," Trends in Genetics 10: 84–88.
Benfey et al., 1993 "Root development In *Arabidopis*: four mutants with dramatically altered root morphogenesis," Development 119:57–70.

(Continued)

*Primary Examiner*—Amy J. Nelson
*Assistant Examiner*—Cynthia Collins
(74) *Attorney, Agent, or Firm*—Nixon Peabody LLP

(57) ABSTRACT

The structure and function of a regulatory gene, SHORT-ROOT (SHR), is described. The SHR gene is expressed specifically in root progenitor tissues of embryos, and in roots and stems of seedlings and plants. SHR expression controls cell division of certain cell types in roots and affects the organization of root and stem tissues, and affects gravitropism of aerial structures. The invention relates to the SHR gene, SHR-like genes, SHR gene products, (including but not limited to transcriptional products such as mRNAs, antisense, and ribozyme molecules, and translational products such the SHR protein, polypeptides, peptides and fusion proteins related thereto), antibodies to SHR gene products, SHR promoters and regulatory regions and the use of the foregoing to improve agronomically valuable plants.

5 Claims, 24 Drawing Sheets

OTHER PUBLICATIONS

Figure 1A:
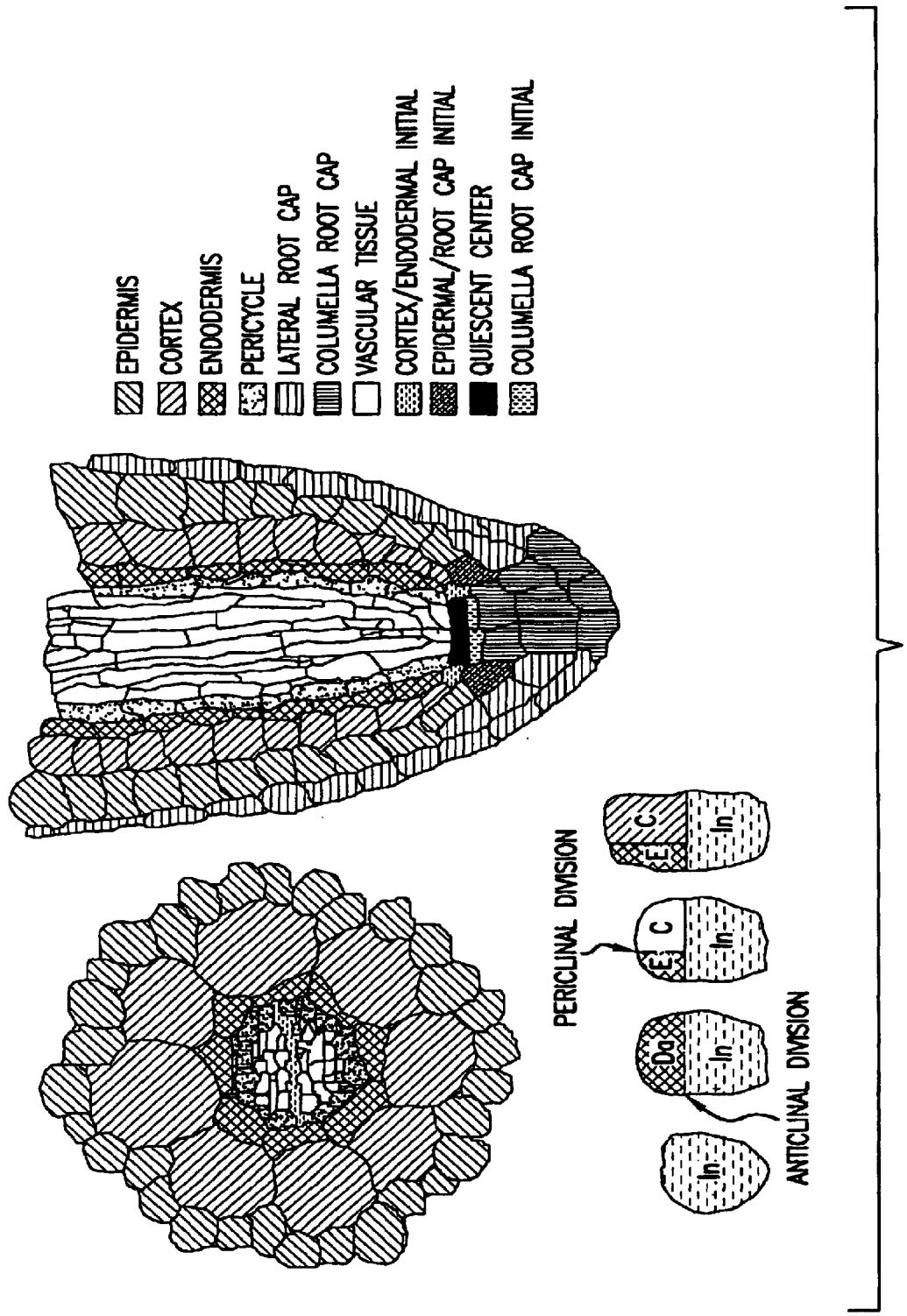
Figure 1B:
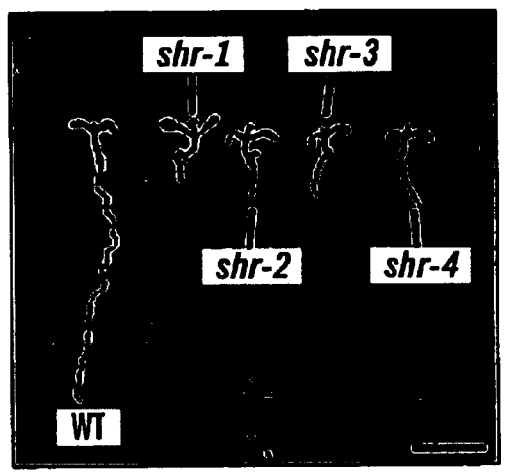

B nfey and Chua, 1989, "Regulated Genes in Transgenic Plants,"Science 244:174–181.

Bevan, 1984, "Binary *Agrobacterium* vectors for plant transf rmation," Nuc. Acid Res. 12:8711–8721.

Bevan and Chilton, 1982, "T–DNA of the *Agrobacterium* TI and RI Plasmids," Ann. Rev. Genet. 18:357–384.

Bjorkmann, 1992, "Perception of Gravity by Plants," Adv. Space Res. 12:195–201.

Bouton et al., 1989, "Specifi ity of *Agrobacterium*–mediated delivery of maize streak virus DNA to members of the Gramineae," Plant Mol. Biol. 12:31–40.

Broglie et al., "Light–Regulated Expression of a Pea Ribulose–1, 5–Bisphosphate Carboxylase Small Subunit Gene in Transformed Plant Cells," Science 224:838–843.

Casper and Pickard, 1989, "Gravitropism in a starchless mutant of *Arabidopsis*," Planta 177:185–197.

Chuang and Meyerowitz, 2000, "Specific and heritable genetic interference by double–stranded RNA in *Arabidopsis thaliana*," PNAS 97:4985–4990.

Clough and Bent, 1998, "Floral dip: a simplified method fro *Agrobacterium*–mediated transformation of *Arabidopsis thaliana*," Plant J, 16:735–743.

Comai et al., 1991, "Novel and useful properties of a chimeric plant promoter combining CaMV 35S and MAS elements," Plant Mol. Biol. 15:373–381.

Coruzzi et al., 1984, "Tissue–specific and light–regulated expression of a pea nuclear gene encoding the small subunit of ribulose–1, 5–biphosphate carboxylase," EMBO J. 3:1671–1679.

D'Halluin et al., 1992, "Transgenic Maize Plants by Tissue Electroporation," Plant Cell 4:1495–1505.

Dietrich et al., 1992, "Downstream DNA Sequences Are Required to Activate a Gene Expressed in the Root Cortex of Embryos and Seedlings," Plant Cell 4:1371–1382.

Di Laurenzio et al., 1998, "The SCARECROW Gene Regulates an Asymmetric Cell Division that is Essential for Generating the Radial Organization of the *Arabidopsis* Root," Cell 86:423–433.

Dolan et al., 1993, "Cellular organisation of the *Arabidopsis thaliana* root," Development 119:71–84.

Edwards et al., 1990, "Cell–specific expression in transgenic plants reveals nonoverlapping roles for chloroplast and cytosolic glutamine synthetase," Proc. Natl. Acad. Sci. USA 87:3459–3463.

Ellis et al., 1987, "Maize *Adh–1* promoter sequences control anaerobic regulation: addition of upstream promoter elements from constitutive genes is necessary for expression in tobacco," EMBO J. 6:11–16.

Fluhr et al., 1986, "Organ–Specific and Light–Induced Expression of Plant Genes," Science 232:1006–1112.

Freshour et al., 1996, "Developmental and Tissue–Specific Structural Alterations of the Cell–Wall Polysaccharides of *Arabidopsis thaliana* Roots," Plant Physiol. 110:1413–1429.

Fromm et al., 1985, "Expression of genes transferred into monocot and dicot plant cells by electroporation," Proc. Natl. Acad. Sci. USA 82:5824–5828.

Fukaki et al., 1996, "Gravitropic Response of Inflorescence Stems in *Arabidopsis thaliana*," Plant Physiol. 110:933–943, 945–955.

Fukaki et al., 1996, "SGR1, SGR2, and SGR3: Novel Genetic Loci Involved in Shoot Gravitropism in *Arabidopsis thaliana*," Plant Physiol. 110:945–955.

Fukaki et al., 1996, "How Do Plant Shoots Bend up?—The Initial Step to Elucidate the Molecular Mechansims of Shoot Gravitropism Using *Arabidopsis thaliana*," Plant Res. 109:129–137.

Fukaki et al., 1998, "Genetic evidence that the endodermis is essential for shoot gravitroplsm in *Arabidopsis thaliana*," Plant J. 14:425–430.

Gaiser and Lomax, 1993, "The Altered Gravitropic Response of the *lazy*–2 Mutant of Tomato is Phytochrome Regulated," Plant Physiol. 102:339–344.

Gautier et al., 1987, "α–DNA IV: α–anomeric and β–anomeric tetrahymidylates covalently linked to intercalating oxazalopyridocarbazole," Nucl. Acids Res. 15:6625–6641.

Greenspan and Bona, 1993, "Idiotypes: structure and immunogenicity," FASEB J 7(5):437–444.

Gurley et al., 1986, "Upstream Sequences Required for Efficient Expression of a Soybean Heat Shock Gene," Mol. Cell. Biol. 6:559–565.

Haseloff et al., 1997, "R moval of a cryptic intom and subcellular localization of green fluorescent protein are r quired to mark transgenic *Arabidopsis* plants brightly," Proc. Natl. Acad. Sci. USA 94:2122–2127.

Hauser et al., 1995, "Conditional root expansion mutants of *Arabidopsis*," Development 121: 1237–1252.

Hauser and Benfey, 1994, "Genetic Regulation of Root Expansion in *Arabidopsis thaliana*," In *Molecular Genetic Analysis of Plant Development and Metabolism*, ds. Coruzzi and Puigdomneceh, P. Springer, Berlin, pp. 31–40.

Helariutta et al., 2000, "The SHORT–ROOT Gen Controls Radial Patterning of the *Arabidopsis* Root through Radial Signaling," Cell 101: 555–567.

Helene et al., 1992, "Control of Gene Expression by Triple Helix–Forming Oligonucleotides," Ann. N.Y. Acad. Sci. 660:27–36.

Hemalsteen et al., 1984, "An *Agrobacterium*–transformed cell culture from the monocot *Asparagus officinalis*," EMBO J 3:3039–3041.

Hooykass–Van Slogteren et al., 1984, "Expression of Ti plasmid genes in monocotyledonous plant infected with *Agrobacterium tumefaciens*," Nature 311:763–764.

Jefferson, 1987, "Assaying Chimeric Genes in Plants: The GUS Gene Fusion System," Plant Mol. Biol. Rep. 5:387–405.

Jenkins, et al., 1986, "Gravitropic responses of wild–type and mutant strains of the moss *Physcomitrella patens*" Plant Cell Environ 9:637–644.

Jofuku et al., 1994, "Control of *Arabidopsis* Flower and Seed Development by the Homeotic Gene *APETALA2*," Plant Cell 6:1211–1225.

Kaeppler et al., 1990, "Silicon carbide fiber–mediated DNA delivery into plant cells," Plant Cell Reporter 9:415–418.

Klein et al., 1988, "Transfer of foreign genes into intact maize cells with high–velocity microprojectiles," Proc. Natl. Acad. Sci. USA 85:4305–4309.

Knox et al., 1990, "Pectin esterification is spatially regulated both within cell walls and between developing tissues of root apices," Planta 181:512–521.

Konieczny and Ausubel, 1993, "A procedure for mapping *Arabidopsis* mutations using co–dominant ecotype–specific PCR–based markers," Plant J. 4:403–410.

Koziel et al., 1984, "a Caulifower Mosaic Virus Promoter Directs Expression of Kanamycin Resistance in Morphogenic Transformed Plants," J. Mol. Appl. Genet. 2:549–562.

Lemaitre et al., 1987, "Specific antiviral acitivity of a poly(L–lysine)–conjugated oligodeoxyribonucleotide sequence complementary to vesicular stomatitis virus N protein mRNA initiation site," Proc. Natl. Acad. Sci. USA 84:648–652.

Li and Chory, 1997, "A Putative Leucine–Rich Repeat Receptor Kinase Involved in Brassinosteroid Signal Transduction," Cell 90:929–938.

Liang et al., 1989, "Differential Regulation of Phenylalanine Ammonia–lyase Genes during Plant Development and by Environmental Cues," J. Biol. Chem. 264:14486–14492.

Lim et al., 2000, "Molecular Analysis of the SCARECROW Gene in Maize Reveals a Common Basis for Radial Patterning in Diverse Meristems," Plant Cell 12: 1307–1318.

Linsbauer (ed.), 1943, *Die physiologischen Scheiden*, Handbuch der Pflanzenanalomie, Berlin: Gerbruder Borntraeger, vol. 5, p. 217.

Long et al., 1993, "The maize transposable element system Ac/Ds as a mutagen in *Arabidopsis*:Identification of an *albino* mutation induced by Ds insertion," Proc. Natl. Acad. Sci. USA 90:10370–10374.

Lucas et al., 1995, "Selective Trafficking of KNOTTED1 Homeodomain Protein and Its mRNA Through Plasmodesmata", Science 270:1980–1983.

Mahonen et al., 2000, "A novel two–component hybrid molecule regulates vascular morphogenesis of the *Arabidopsis* root," Genes & Development 14:2938–2943.

Malamy and B nfey, 1997, "Organization and cell differentiation in lateral roots of *Arabidopsis thaliana*," Development 124:33–44.

Malamy and Benfey, 1997, "Analysis of SCARECROW expression using a rapid system for assessing transgene expression in *Arabidopsis* roots," Plant Journal 12: 957–963.

Malamy and Benfey, 1997, "Down and out in *Arabidopsis*: the formation of lateral ro ts," Trends in Plant Science 2: 390–396.

Masson, 1996, "Root gravitropism," BioEssays 17:119–127.

Mayer et al., 1993, "Apical–based pattern formation in the *Arabidopsis* embryo: studies on the role of the *gnom* gen," Development 117:149–162.

Mayer et al., 1999, "Sequence and analysis of chromosome 4 of th plant *Arabidosspsis thaliana*," Nature 402:769–777.

Meier et al., 1991, "Elicitor–Inducible and Constitutive in Vivo DNA Footprints Indicate Novel cis–Acting Elements in the Promoter of a Parsley Gene Encoding Pathogenesis–Related Protein 1," Plant Cell 3:309–315.

Melo–Oliveira et al., 1996, "*Arabidopsis* mutant analysis and gene regulation define a nonredundant role for glutamate dehydrogenase in nitrogen assimilation," Proc. Natl. Acad. Sci. USA 93:4718–4723.

Odell et al., 1985, "Identification of DNA sequences required for activity of the cauliflower mosaic virus 35S promoter," Nature 313–810–812.

Offringa et al., 1990, "Extrachromosomal homologous recombination and gene targeting in plant cells after *Agrobacterium* mediated transformation," EMBO J. 9:3077–3084.

Ow et al., 1986, "Transient and Stable Expression of the Firefly Luciferase Gene in Plant Cells and Transgenic Plants," Science 234:856–859.

Paszkowski et al., 1984, "Direct gene transfers to plants," EMBO J 3:2717–2722.

Peng et al., 1997, "Teh *Arabidopsis GAI* gene defines a signaling pathway that negatively regulates gibberellin responses," Genes and Dev. 11:3194–3205.

Peng et al., 1997, "'Green revolution' genes encode mutant gibberellin response modulators," Nature 400:256–261.

Poff et al., 1994, in *The Physiology of Tropisms*, Meyerowitz & Somerville (eds), Cold Spring Laboratory Press, Plainview, NY, pp. 639–664.

Potrykus et al., 1985, "Molecular and general genetics of a hybrid foreign gene introduced into tobacco by direct gene transfer," Mol. Gen. Genet. 199:169–177.

Poulsen and Chua, 1988, "Dissection of 5' upsteam sequences for selective expression of the *Nicotiana plumbaginifolia* rbc–S–8B gene," Mol. Gen. Genet. 214:16–23.

Pysh et al., 1999, "The GRAS gene family in *Arabidopsis*: sequence characterization and basic expression analysis of the SCARECROW–LIKE genes," Plant J. 18:111–119.

Pysh and Benfey, 1997, "Root Cell Extension: Genetic and Molecular Approaches," in *Radical Biology: Advances and Perspectives in the Function of Plant Roots*, eds. Flores, Lynch and Eisenstadt, American Soc. Of Plant Physiologists, Maryland, pp. 34–47.

Rogers et al., 1986, "Gene Transfer in Plants: Production of Transformed Plants Using Ti Plasmid Vectors," Methods Enzymol. 118:627–641.

Sabatini et al., 1999, "An Auxin–Dependent Distal Organizer of Pattern and Polarity in the *Arabidopsis* Root," Cell 99:463–472.

Sack, 1987, "The structure of the stem endodermis in etiolated pea seedlings," Can J. Bot. 65:1514–1519.

Sack, 1991, "Plant Gravity Sensing," Intern. Rev. Cytol. 127:193–252.

Sack and Kiss, 1989, "Rootcap Structure in Wild Type and in a Starchless Mutant of *Arabidopsis*," Amer. J. Bot. 76:454–464.

Salinas et al., 1992, "Two G–Box–Related Sequences Confer Different Expression Patterns in Transgenic Tobacco," Plant Cell 4:1485–1493.

Scheres and Benfey, 1999, "Asymmetric Cell Division in Plants," Annual Review of Plant Physiology and Plant Molecular Biology 50: 505–537.

Scheres et al., 1995, "Mutations affecting the radial organisation of th *Arabidopsis* root display specific defects throughout the embryonic axis," Development 121:53–62.

Scheres et al., 1994, "Embryonic origin of the *Arabidopsis* primary root and root meristem initials," Development 120:2475–2487.

Schiefelbein and Benfey, 1994, "Root Development in *Arabidopsis*," In *Arabidopsis*, eds. Meyerowitz and Somerville, Cold Spring Laboratory Press, pp. 335–354.

Schiefelbein and Benfey, 1993, "Meeting Report: International Symposium on the Molecular Genetics of Root Developement," Plant Molecular Biology Report 11:60–64.

Schiefelbein and Benfey, 1991, "The Development of Plant Roots: New Approaches to Underground Problems," Plant Cell 3: 1147–1154.

Schumacher et al., 1999, "The *Lateral suppressor* (Ls) gene of tomato encodes a new member of the VHIIMD protein family," Proc. Natl. Acad. Sci. USA 96:290–295.

Shimamoto, 1989, "Fertile transgenic rice plant regenerated from transformed protoplasts," Nature 338:274–276.

Sievers and Braun, 1996, "Chapter 3—The Root Cap: Structure and Function," in *Plant Roots:The Hidden Half*, Wassail et al. (eds.), New York: M. Dekker, pp. 31–49.

Silverstone et al., 1998, "The *Arabidopsis* RGA Gene Encodes a Transcriptional Regulator Repressing the Gibberellin Signal Transduction Pathway," Plant Cell 10:155–169.

Skriver et al., 1991, "Cis–acting DNA elements responsive to gibberellin and its antagonist abscisic acid," Proc. Natl. Acad. Sci. USA 88:7266–7270.

Strittmatter and Chua, 1987, "Artificial combination of two cis–regulatory elements generates a unique pattern of expression in transgenic plants," Proc.Natl. Acad. Sci. USA 84:8986–8990.

Takatsuji et al., 1991, "Characterization of a zinc finger DNA–binding protein expressed specifically in *Petunia* petals and seedings," EMBO Journal 11: 241–249.

Tingey et al., 1987, "Glutamine synthetase genes of pea encode distinct polypeptides which are differentially expressed in leaves, roots and nodules," EMBO J. 6:1–9.

van den Berg et al., 1995, "Cell fate in the *Arbidopsis* root meristem determined by directional signalling," Nature 378:62–65.

van den Berg et al., 1997, "Short–range Control of Cell Differentiation in the *Arabidopsis* root meristem," Nature 390:287–289.

Volkmann and Sievers, 1979, "Graviperception in Multicellular Organs," Encyclopedia Plant Physiol., N.S. vol. 7, pp. 573–600.

Volkmann et al., 1993, "Graviresponsiveness of Cress Seedlins and Structural Status of Presumptive Statocytes from the Hypocotyl," J. Pl. Physiol. 142:710–716.

Weissenborn and Larson, 1992, "Structure and Regulation of the glpFK Operon Encoding Glycerol Diffusion Facilitator and Glycerol Kinase of *Escherichia coli* K–12," J. Biol. Chem. 267:6122–6131.

Wisman et al., 1998, "The behaviour of the autonomous maize transposable element En/Spm in *Arabidopsis thaliana* allows efficient mutagenesis," Plant Mol. Biol. 37:989–999.

Wysocka–Diller et al., 2000, "Molecular analysis of SCARECROW function reveals a radial patterning mechanism common to root and shoot," Development 127:595–603.

Wysocka–Diller and Benfey, 1997, "Root development: signaling down and around," BioEssays 19:959–965.

Yamamoto et al., 1980, "Identification of a Functional Promoter in the Long Terminal Repeat of a Rous Sarcoma Virus," Cell 22:787–797.

* cited by examiner

```
LS  144  PFIRFTQLTANQAILEAINGNHQAIHIVDFDINHGVQWPPLMQALADRYPA-PTLRITG
GAI 248  PYLKFAHFTANQAILEAFQGK-KRVHVIDFSMSQGLQWPALMQALALRPGGPPVFRLTG
RGA 301  PYLKFAHFTANQAILEAFEGK-KRVHVIDFSMNQGLQWPALMQALALREGGPPTFRLTG
SCR 379  PLVKFSHFTANQAIQEAFEKE-DSVHIIDLDIMQGLQWPGLFHILASRPGGPPHVRLTG
SHR 233  PWATFGHVAANGAILEAVDGE-AKIHIVDISSTFCTQWPTLLEALATRSDDTPHLRLTT
```

*FIG. 2B*

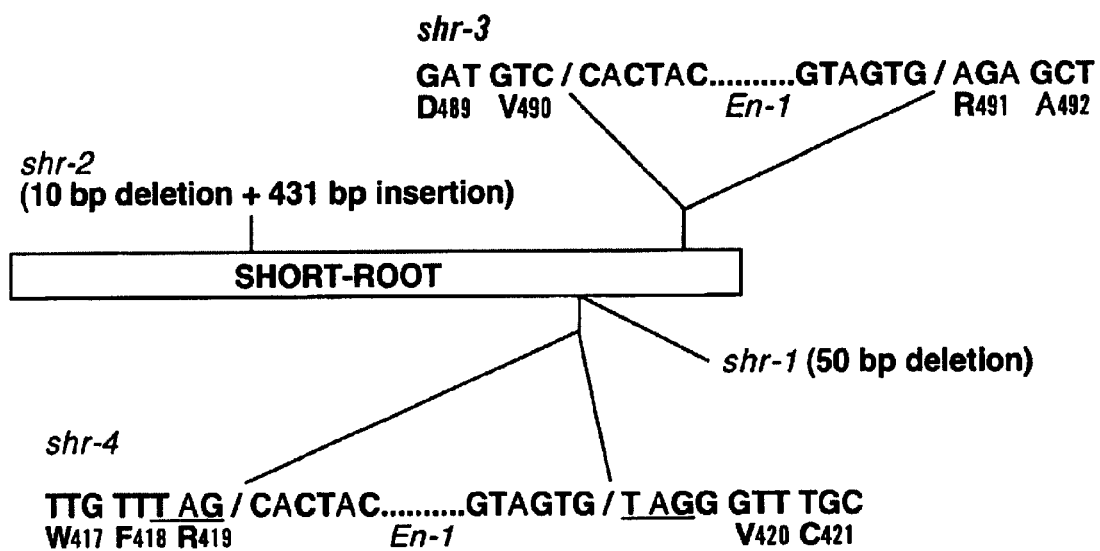

*FIG. 2C*

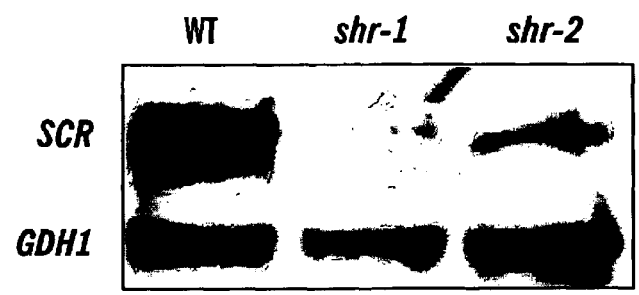
FIG. 5A
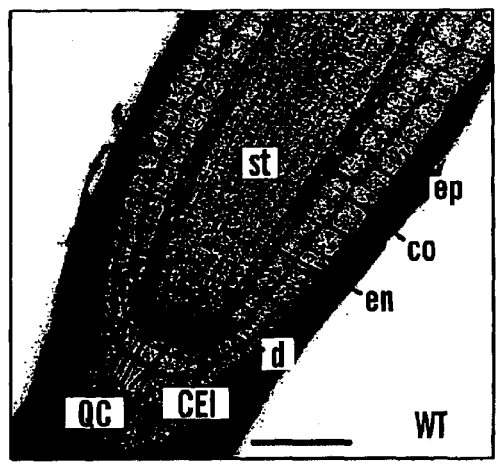 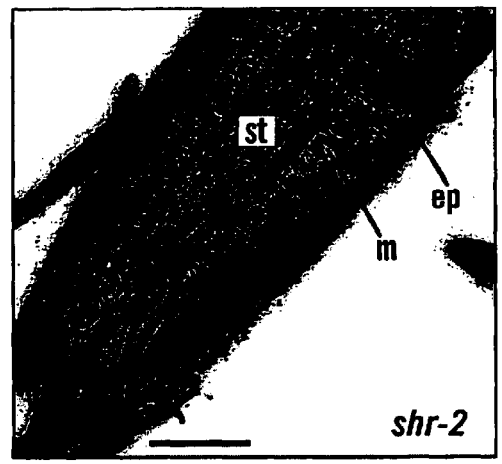
FIG. 5B   FIG. 5C

```
   1 atcgattaag agaaaataga gttttcatgc accagtgttg atagtaacgt agtcgcggaa
  61 tgtctaaaac gattatgagt ttggtgtttt gattggttag aattggtatt agtaggacat
 121 tctaactttt ttgttagtct gttgatttag gatgcgtaaa gagtcttttt attttacacc
 181 agttgagact tgggatcgat agtacttgaa acacttggtt ggtttcatgt atttggccta
 241 tatataaaca aacatcgtaa ttatatacgg attttttcg gaatttacg ccatatctgt
 301 aagtatatat aacatgcatg tcgttttcaa attcatatga tgaacgatcc acgtaagtgc
 361 tactactcct acaatattgc atgagagaga tatgtattta taaattttat tttgaagaag
 421 aaataagagg gaaggttact tgggtggatc gatgtgaaaa caaaagaaga aaaagcgaaa
 481 cccactaagc cattacatga tatcgacctt cttatctttt tcctctttat tttattttc
 541 tcaggacttt tttctactta atgaaacctc caaactatct aactaataca ctcccatgta
 601 gaataaagaa aattatataa gatattgttg atattttgta actagaaaat atatttgctc
 661 tgtaattttt cgtaagttaa atcaacattt ttcagtagaa acaaatatta ctgcaaaaag
 721 taggatcatt attttgtcc aaaatctcag ttagctatag ggttgtagta aaaacaaaac
 781 acattcttga tttgccccaa aaaataaaga gagagaagaa tattgttcaa aagtggtctc
 841 ttctctctct aattatgttt tcactaaacc caattagatt caaacagtct acaaagtcca
 901 aaagataaac atgggacaac aattcgatgc aaaaaatcct cttttcatgc tcttttttta
 961 ttctctagtc ttttaaatta ctaataaaaa ctcacaaatc caccaaaccc attctctaca
1021 actcaccttc atctagattt acccactccc accgagaaac acaagaaaaa aaatatacat
1081 atataaatat acaagacaac acatgatgct gatgcaatat acacaacaaa gtattaaatc
1141 ttagatattg tgggtctccc tttcttctat tcattttctt attcattaaa aaaaaaaat
1201 ggatactctc tttagactag tcagtctcca acaacaacaa caatccgata gtatcattac
1261 aaatcaatct tcgttaagca gaacttccac caccactact ggctctccac aaactgctta
1321 tcactacaac tttccacaaa acgacgtcgt cgaagaatgc ttcaactttt tcatggatga
1381 agaagacctt tcctcttctt cttctcacca caaccatcac aaccacaaca atcctaatac
1441 ttactactct cctttcacta ctcccaccca ataccatccc gccacatcat caacccttc
1501 ctccaccgcc gcagccgcag ctttagcctc gccttactcc tcctccggcc accataatga
1561 cccttccgcg ttctccatac ctcaaactcc tccgtccttc gacttctcag ccaatgccaa
1621 gtgggcagac tcggtccttc ttgaagcggc acgtgccttc tccgacaaag acactgcacg
1681 tgcgcaacaa atcctatgga cgctcaacga gctctcttct ccgtacggag acaccgagca
1741 aaaactggct tcttacttcc tccaagctct cttcaaccgc atgaccggtt caggcgaacg
1801 atgctaccga accatggtaa cagctgcagc cacagagaag acttgctcct tcgagtcaac
1861 gcgaaaaact gtactaaagt tccaagaagt tagcccctgg gccacgtttg gacacgtggc
1921 ggcaaacgga gcaatcttgg aagcagtaga cggagaggca aagatccaca tcgttgacat
1981 aagctccacg ttttgcactc aatggccgac tcttctagaa gctttagcca caagatcaga
2041 cgacacgcct cacctaaggc taaccacagt tgtcgtggcc aacaagtttg tcaacgatca
2101 aacggcgtcg catcggatga tgaaagagat cggaaaccga atggagaaat tcgctaggct
2161 tatgggagtt ccttcaaat ttaacattat tcatcacgtt ggagatttat ctgagtttga
2221 tctcaacgaa ctcgacgtta aaccagacga agtcttggcc attaactgcg taggcgcgat
2281 gcatgggatc gcttcacgtg gaagccctag agacgctgtg atatcgagtt tccgacggtt
2341 aagaccgagg attgtgacgg tcgtagaaga agaagctgat cttgtcggag aagaagaagg
2401 tggctttgat gatgagttct tgagagggtt tggagaatgt tacgatggt ttagggtttg
2461 cttcgagtca tgggaagaga gttttccaag gacgagcaac gagaggttga tgctagagcg
2521 tgcagcggga cgtgcgatcg ttgatcttgt ggcttgtgag ccgtcggatt ccacggagag
2581 gcgagagaca gcgaggaagt ggtcgaggag gatgaggaat agtgggtttg gagcggtggg
2641 gtatagtgat gaggtggcgg atgatgtcag agctttgttg aggagatata agaaggtgt
2701 ttggtcgatg gtacagtgtc ctgatgccgc cggaatattc ctttgttgga gagatcagcc
2761 ggtggtttgg gctagtgcgt ggcggccaac gtaaagggtt gttttattt tttcataagg
2821 aattc
```

FIG. 8

```
MDTLFRLVSL QQQQQSDSII TNQSSLSRTS TTTTGSPQTA YHYNFPQNDV VEECFNFFMD
EEDLSSSSSH HNHHNHNNPN TYYSPFTTPT QYHPATSSTP SSTAAAAALA SPYSSSGHHN
DPSAFSIPQT PPSFDFSANA KWADSVLLEA ARAFSDKDTA RAQQILWTLN ELSSPYGDTE
QKLASYFLQA LFNRMTGSGE RCYRTMVTAA ATEKTCSFES TRKTVLKFQE VSPWATFGHV
AANGAILEAV DGEAKIHIVD ISSTFCTQWP TLLEALATRS DDTPHLRLTT VVVANKFVND
QTASHRMMKE IGNRMEKFAR LMGVPFKFNI IHHVGDLSEF DLNELDVKPD EVLAINCVGA
MHGIASRGSP RDAVISSFRR LRPRIVTVVE EEADLVGEEE GGFDDEFLRG FGECLRWFRV
CFESWEESFP RTSNERLMLE RAAGRAIVDL VACEPSDSTE RRETARKWSR RMRNSGFGAV
GYSDEVADDV RALLRRYKEG VWSMVQCPDA AGIFLCWRDQ PVVWASAWRP T
```

*FIG. 9*

```
   1 aaaaaaaaaa aatggatact ctctttagac tagtcagtct ccaacaacaa caacaatccg
  61 atagtatcat tacaaatcaa tcttcgttaa gcagaacttc caccaccact actggctctc
 121 cacaaactgc ttatcactac aactttccac aaaacgacgt cgtcgaagaa tgcttcaact
 181 ttttcatgga tgaagaagac ctttcctctt cttcttctca ccacaaccat cacaaccaca
 241 acaatcctaa tacttactac tctcctttca ctactcccac ccaataccat cccgccacat
 301 catcaacccc ttcctccacc gccgcagccg cagctttagc ctcgccttac tcctcctccg
 361 gccaccataa tgacccttcc gcgttctcca tacctcaaac tcctccgtcc ttcgacttct
 421 cagccaatgc caagtgggca gactcggtcc ttcttgaagc ggcacgtgcc ttctccgaca
 481 aagacactgc acgtgcgcaa caaatcctat ggacgctcaa cgagctctct tctccgtaat
 541 gaaaaccgct tcatttttcct tgtatttgtc tgaggttagg attagaccat tggttgttac
 601 tttcgaattc ttccaattta gttgttactt tcgaattctt ccatctctta gtttactaaa
 661 acaaacttat gtgccccata tttctccaac aatttgttga gtggtagctt acgttttact
 721 gtatacgctt ttgcaggtta tatcagcaca accattaatg atggcccggg atgtttgatg
 781 ctaagatgtc ctgacccatc ttgtcttgct gctgttggtc atgatatggt tgacaaatta
 841 gcgtctgaag acgaaaagga gaagtacaac agatattttc ttaggtctta tattgaagac
 901 aacagaaagg taagcagtct agaaaattta tatcacacag actggtatta atgtcgctgg
 961 tcttttattg agcaaaaact ggcttcttac ttcctccaag ctctcttcaa ccgcatgacc
1021 ggttcaggcg aacgatgcta ccgaaccatg gtaacagctg cagccacaga gaagacttgc
1081 tccttcgagt caacgcgaaa aactgtacta aagttccaag aagttagccc ctgggccacg
1141 tttggacacg tggcggcaaa cggagcaatc ttggaagcag tagacggaga ggcaaagatc
1201 cacatcgttg acataagctc cacgtttgtgc actcaatggc cgactcttct agaagcttta
1261 gccacaagat cagacgacac gcctcaccta aggctaacca cagttgtcgt ggccaacaag
1321 tttgtcaacg atcaaacggc gtcgcatcgg atgatgaaag atcggaaa ccgaatggag
1381 aaattcgcta ggcttatggg agttcctttc aaatttaaca ttattcatca cgttggagat
1441 ttatctgagt tgatctcaa cgaactcgac gttaaaccag acgaagtctt ggccattaac
1501 tgcgtaggcg cgatgcatgg gatcgcttca cgtggaagcc ctagagacgc tgtgatatcg
1561 agtttccgac ggttaagacc gaggattgtg acggtcgtag aagaagaagc tgatcttgtc
1621 ggagaagaag aaggtggctt tgatgatgag ttcttgagag ggtttggaga atgtttacga
1681 tggtttaggg tttgcttcga gtcatgggaa gagagttttc caaggacgag caacgagagg
1741 ttgatgctag agcgtgcagc gggacgtgcg atcgttgatc ttgtggcttg tgagccgtcg
1801 gattccacgg agaggcgaga gacagcgagg aagtggtcga ggaggatgag gaatagtggg
1861 tttggagcgg tggggtatag tgatgaggtg gcggatgatg tcagagcttt gttgaggaga
1921 tataaagaag gtgtttggtc gatggtacag tgtcctgatg ccgccggaat attcctttgt
1981 tggagagatc agccggtggt ttgggctagt gcgtggcggc caacgtaaag ggttgttttt
2041 atttttcat aaggaattc
```

*FIG. 10*

FIG. 11
2.5-kb SHORT-ROOT PROMOTER SEQUENCE

```
           10         20         30         40         50
   1234567890 1234567890 1234567890 1234567890 1234567890
   AGAAGCAGAG CGTGGGGTTT CTTCTAATAA TTGTAGAAGA AACTGATCAT     50
   GAGAACATTT GATCTACCAG AGATGGTGAT GACTCATAAG ATGTAAATAT    100
   CTACTGCATT ATGTCTAGCC TAGGCTATAA TGTAGATTTG ATCACTTTCT    150
   TCATTAATTA GTTTGGAATT TTAGCATGAT ATAGCATATA TCTAAATATG    200
   TCCGAAACTT TCCTACATAC TAGAAAATAT GGAGAGTTAT GTAATGTAGG    250
   TTTGCTTGTT AATATACAAA ATAACATCAT CATTTAGTTT TTAGATTTTT    300
   TATTTTATTT TTTATAATGG TGCTACGTAC GTGGCGATCA AATTATTCCA    350
   ATTTTGAGAC TTCGGGATTT TAAACGAAAT TAAACAATGG GCATGAGCTC    400
   GGGGGGATAG ACAAGATTAA TGCTTTGTAT CGAGACAAAC GAGAAAATCA    450
   TGATGAGCCT ATGCATTAAG TGCCGTTGGT TAATTAGAGG TTCGCATATA    500
   CATAAACCAG TAGACATATG GATAAATATG AACACACACA CCAAAAAAGT    550
   GGGAAATCTA AATAAGTGTA GAGAATAATA AGTCCTCAGG TGGGAGATTC    600
   AAAGAGAGGA CAATGAAGGG TATATAGACT CTAAACAAAA ATGGCATGAC    650
   TTAGTGGAGA GGGTTTTAAA TTGAAACAAG TAGGATTGAA GAACAAGAAA    700
   ACAAAGAAGC ATGCCCTAGA TTTCTGAGAT AATAATTACA CATTGCTGTT    750
   TATATAAGGT AAGAGAATAT GACACATTGG TTGGTTTCTT ACGGGTAAAT    800
   GTGAAGAAAA AAAAATAGTA ATATTTGAGA AAATCTAAAA TAGTAAAGAG    850
   GTATATATGG AGAAGAAGAG AGAAAAGGGA AAAATAGTGG CAGAGAATGG    900
   AGAGAGGTTA GGAGGCAAAG GCAAATGTGG AGCTTTGATG ATGTTGATGC    950
   ACGCCGTCAG CTTTTCTTCA CGCCTGCTCC CACTCACTCA CACCTATGAA   1000
   CATTCTCTCT CTATTTTATA ATTATATTCA CATGTCTCTA TGTTACTATG   1050
   TAAATGGTGA CCACTTAAGT ATTTATATAT CATGTATATA TCTTATAGGT   1100
   ATCATACAAA ATGGTCATGA AACTTTTGCA ATTTCAATCT ACTTGTTCAT   1150
   TGTAGATGCT AGCTTTTCAC ATGTTTTGAA AATTAGTCTG GATCTGAAAT   1200
   TCTTTAATTA GCATTGTTTT GTTGGTCAAC GTTTAATTTC TTGATTATTG   1250
   ATGTCAAAAA TTCAGAGCGT TCAGAACTCT TACACTAATT TCTTAAAAAT   1300
   AATCGATTAA GAGAAAATAG AGTTTTCATG CACCAGTGTT GATAGTAACG   1350
   TAGTCGCGGA ATGTCTAAAA CGATTATGAG TTTGGTGTTT TGATTGGTTA   1400
   GAATTGGTAT TAGTAGGACA TTCTAACTTT TTTGTTAGTC TGTTGATTTA   1450
   GGATGCGTAA AGAGTCTTTT TATTTTACAC CAGTTGAGAC TTGGGATCGA   1500
   TAGTACTTGA AACACTTGGT TGGTTTCATG TATTTGGCCT ATATATAAAC   1550
   AAACATCGTA ATTATATACG GATTTTTTTC GGAATTTTAC GCCATATCTG   1600
   TAAGTATATA TAACATGCAT GTCGTTTTCA AATTCATATG ATGAACGATC   1650
   CACGTAAGTG CTACTACTCC TACAATATTG CATGAGAGAG ATATGTATTT   1700
   ATAAATTTTA TTTTGAAGAA GAAATAAGAG GGAAGGTTAC TTGGGTGGAT   1750
   CGATGTGAAA ACAAAAGAAG AAAAAGCGAA ACCCACTAAG CCATTACATG   1800
   ATATCGACCT TCTTATCTTT TTCCTCTTTA TTTTATTTTT CTCAGGACTT   1850
   TTTTCTACTT AATGAAACCT CCAAACTATC TAACTAATAC ACTCCCATGT   1900
   AGAATAAAGA AAATTATATA AGATATTGTT GATATTTGT AACTAGAAAA   1950
   TATATTTGCT CTGTAATTTT TCGTAAGTTA AATCAACATT TTTCAGTAGA   2000
   AACAAATATT ACTGCAAAAA GTAGGATCAT TATTTTGTC CAAAATCTCA   2050
   GTTAGCTATA GGGTTGTAGT AAAAACAAAA CACATTCTTG ATTTGCCCCA   2100
   AAAAATAAAG AGAGAGAAGA ATATTGTTCA AAAGTGGTCT CTTCTCTCTC   2150
   TAATTATGTT TTCACTAAAC CCAATTAGAT TCAAACAGTC TACAAAGTCC   2200
   AAAAGATAAA CATGGGACAA CAATTCGATG CAAAAAATCC TCTTTTCATG   2250
   CTCTTTTTTT ATTCTCTAGT CTTTTAAATT ACTAATAAAA ACTCACAAAT   2300
   CCACCAAACC CATTCTCTAC AACTCACCTT CATCTAGATT TACCCACTCC   2350
   CACCGAGAAA CACAAGAAAA AAAATATACA TATATAAATA TACAAGACAA   2400
   CACATGATGC TGATGCAATA TACACAACAA AGTATTAAAT CTTAGATATT   2450
   GTGGGTCTCC CTTTCTTCTA TTCATTTTCT TATTCATTAA AAAAAAAAAA   2500
   TG                                                      2502
```

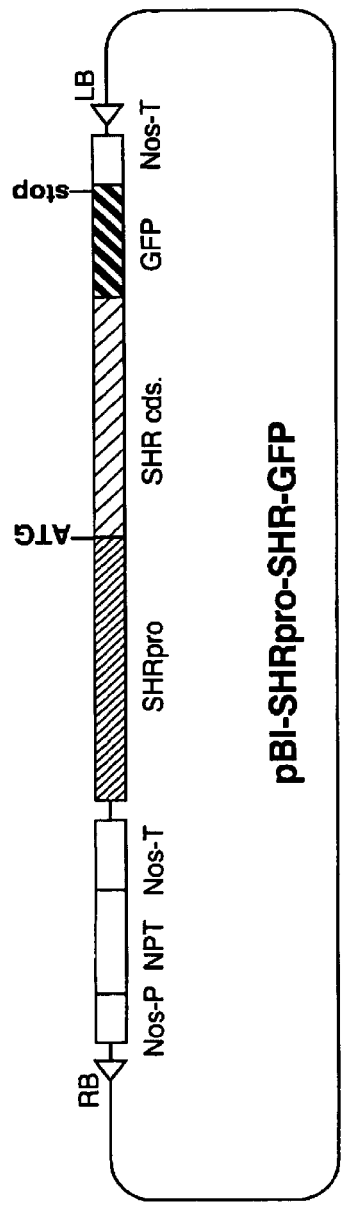 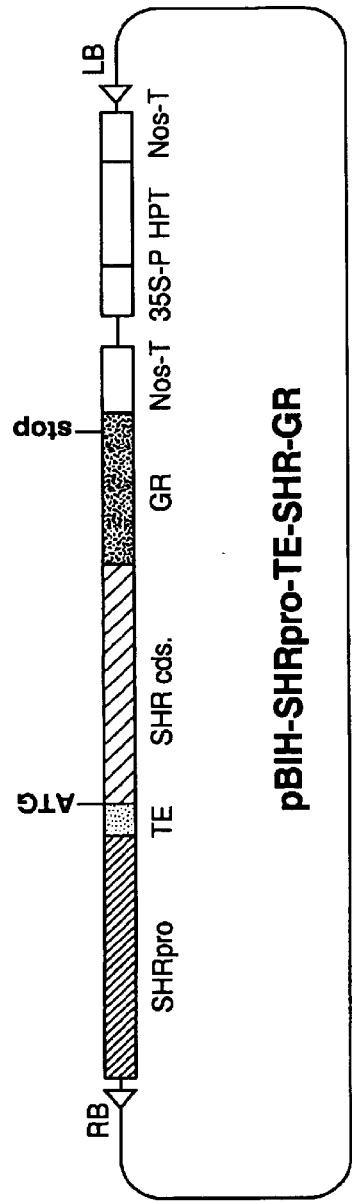

RB, right border sequence from *Agrobacterium* Ti plasmid
SHRpro, 2.5-Kb 5' upstream region of *SHORT-ROOT* gene
TE, translational enhancer element of tobacco etch virus
SHR cds., *SHORT-ROOT* protein coding region
GR, rat glucocorticoid receptor domain coding sequence
GFP, green fluorescent protein coding sequence
Nos-T, transcriprion terminator of nopaline synthetase gene
35S-P, cauliflower mosaic virus 35S promoter
HPT, hygromycin phosphotransferase coding sequence
NPT, neomycin phosphotransferase coding sequence
LB, left border sequence from *Agrobacterium* Ti plasmid

*FIG. 12A*

ECTOPIC SHR EXPRESSION CAUSED ABNORMAL ROOT CELL DIVISIONS

ECTOPIC SHR EXPRESSION UNDER THE SCR PROMOTER RESULTED IN THE INDETERMINATE CELL DIVISIONS IN GROUND TISSUE.

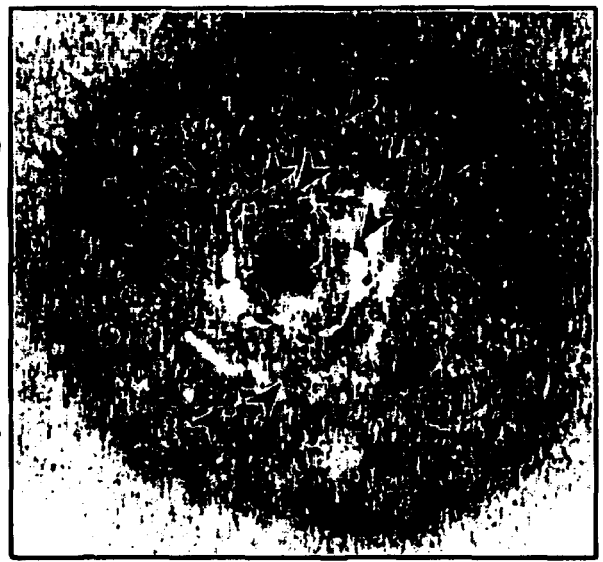
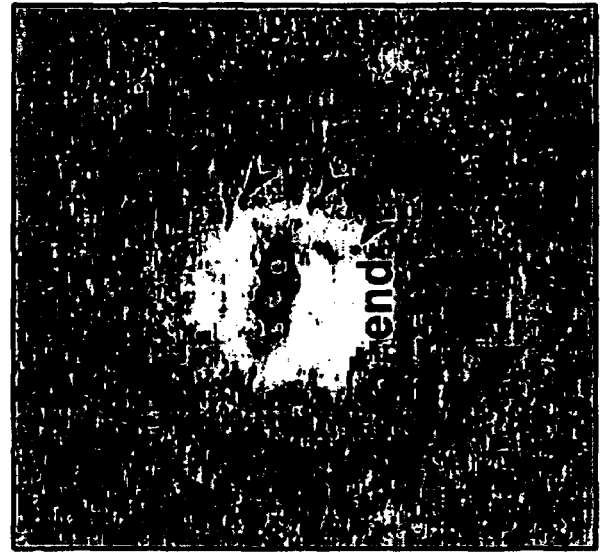
Casparian strip occurs ectopically in the *SCRpro::SHR* transgenic root
*FIG. 16*

SEQUENCE LISTING

<160> NUMBER OF SEQ ID NOS: 17

<210> SEQ ID NO 1
<211> LENGTH: 2825
<212> TYPE: DNA
<213> ORGANISM: Arabidopsis thaliana

<400> SEQUENCE: 1

```
atcgattaag agaaaataga gttttcatgc accagtgttg atagtaacgt agtcgcggaa      60
tgtctaaaac gattatgagt ttggtgtttt gattggttag aattggtatt agtaggacat     120
tctaactttt ttgttagtct gttgatttag gatgcgtaaa gagtcttttt attttacacc     180
agttgagact tgggatcgat agtacttgaa acacttggtt ggtttcatgt atttggccta     240
tatataaaca aacatcgtaa ttatatacgg atttttttcg gaattttacg ccatatctgt     300
aagtatatat aacatgcatg tcgttttcaa attcatatga tgaacgatcc acgtaagtgc     360
tactactcct acaatattgc atgagagaga tatgtattta taaattttat tttgaagaag     420
aaataagagg gaaggttact tgggtggatc gatgtgaaaa caaagaaga aaaagcgaaa      480
cccactaagc cattacatga tatcgaccct cttatctttt tcctctttat tttatttttc     540
tcaggacttt tttctactta atgaaacctc caaactatct aactaataca ctcccatgta     600
gaataaagaa aattatataa gatattgttg atattttgta actagaaaat atatttgctc     660
tgtaattttt cgtaagttaa atcaacattt ttcagtagaa acaaatatta ctgcaaaaag     720
taggatcatt atttttgtcc aaaatctcag ttagctatag ggttgtagta aaaacaaaac     780
acattcttga tttgccccaa aaaataaaga gagagaagaa tattgttcaa aagtggtctc     840
ttctctctct aattatgttt tcactaaacc caattagatt caaacagtct acaaagtcca     900
aaagataaac atgggacaac aattcgatgc aaaaaatcct cttttcatgc tctttttta      960
ttctctagtc ttttaaatta ctaataaaaa ctcacaaatc caccaaaccc attctctaca    1020
actcaccttc atctagattt acccactccc accgagaaac acaagaaaaa aaatatacat    1080
atataaatat acaagacaac acatgatgct gatgcaatat acacaacaaa gtattaaatc    1140
ttagatattg tgggtctccc tttcttctat tcattttctt attcattaaa aaaaaaaat     1200
ggatactctc tttagactag tcagtctcca acaacaacaa caatccgata gtatcattac    1260
aaatcaatct tcgttaagca gaacttccac caccactact ggctctccac aaactgctta    1320
tcactacaac tttccacaaa acgacgtcgt cgaagaatgc ttcaactttt tcatggatga    1380
agaagacctt tcctcttctt cttctcacca caaccatcac aaccacaaca atcctaatac    1440
ttactactct cctttcacta ctcccaccca ataccatccc gccacatcat caacccttc     1500
ctccaccgcc gcagccgcag ctttagcctc gccttactcc tcctccggcc accataatga    1560
cccttccgcg ttctccatac ctcaaactcc tccgtccttc gacttctcag ccaatgccaa    1620
gtgggcagac tcggtccttc ttgaagcggc acgtgccttc tccgacaaag acactgcacg    1680
tgcgcaacaa atcctatgga cgctcaacga gctctcttct ccgtacggag acaccgagca    1740
aaaactggct tcttacttcc tccaagctct cttcaaccgc atgaccggtt caggcgaacg    1800
atgctaccga accatggtaa cagctgcagc cacagagaag acttgctcct tcgagtcaac    1860
gcgaaaaact gtactaaagt tccaagaagt tagcccctgg gccacgtttg gacacgtggc    1920
ggcaaacgga gcaatcttgg aagcagtaga cggagaggca aagatccaca tcgttgacat    1980
aagctccacg ttttgcactc aatggccgac tcttctagaa gctttagcca caagatcaga    2040
```

```
cgacacgcct cacctaaggc taaccacagt tgtcgtggcc aacaagtttg tcaacgatca      2100
aacggcgtcg catcggatga tgaaagagat cggaaaccga atggagaaat cgctaggct      2160 tatgggagtt cctttcaaat ttaacattat tcatcacgtt ggagatttat ctgagtttga      2220
tctcaacgaa ctcgacgtta aaccagacga agtcttggcc attaactgcg taggcgcgat      2280
gcatgggatc gcttcacgtg gaagccctag agacgctgtg atatcgagtt tccgacggtt      2340
aagaccgagg attgtgacgg tcgtagaaga agaagctgat cttgtcggag aagaagaagg      2400
tggctttgat gatgagttct tgagagggtt tggagaatgt ttacgatggt ttagggtttg      2460
cttcgagtca tgggaagaga gttttccaag gacgagcaac gagaggttga tgctagagcg      2520
tgcagcggga cgtgcgatcg ttgatcttgt ggcttgtgag ccgtcggatt ccacggagag      2580
gcgagagaca gcgaggaagt ggtcgaggag gatgaggaat agtgggtttg gagcggtggg      2640
gtatagtgat gaggtggcgg atgatgtcag agctttgttg aggagatata agaaggtgt      2700 ttggtcgatg gtacagtgtc ctgatgccgc cggaatattc ctttgttgga gagatcagcc      2760
ggtggtttgg gctagtgcgt ggcggccaac gtaaagggtt gttttttattt tttcataagg      2820 aattc                                                                  2825
```

<210> SEQ ID NO 2
<211> LENGTH: 531
<212> TYPE: PRT
<213> ORGANISM: Arabidopsis thaliana

<400> SEQUENCE: 2

```
Met Asp Thr Leu Phe Arg Leu Val Ser Leu Gln Gln Gln Gln Gln Ser
1               5                   10                  15

Asp Ser Ile Ile Thr Asn Gln Ser Ser Leu Ser Arg Thr Ser Thr Thr
            20                  25                  30

Thr Thr Gly Ser Pro Gln Thr Ala Tyr His Tyr Asn Phe Pro Gln Asn
        35                  40                  45

Asp Val Val Glu Glu Cys Phe Asn Phe Phe Met Asp Glu Glu Asp Leu
    50                  55                  60

Ser Ser Ser Ser His His Asn His Asn His Asn Asn Pro Asn
65                  70                  75                  80
Thr Tyr Tyr Ser Pro Phe Thr Pro Thr Gln Tyr His Pro Ala Thr
                85                  90                  95

Ser Ser Thr Pro Ser Ser Thr Ala Ala Ala Ala Leu Ala Ser Pro
            100                 105                 110

Tyr Ser Ser Gly His His Asn Asp Pro Ser Ala Phe Ser Ile Pro
        115                 120                 125

Gln Thr Pro Pro Ser Phe Asp Phe Ser Ala Asn Ala Lys Trp Ala Asp
    130                 135                 140

Ser Val Leu Leu Glu Ala Ala Arg Ala Phe Ser Asp Lys Asp Thr Ala
145                 150                 155                 160

Arg Ala Gln Gln Ile Leu Trp Thr Leu Asn Glu Leu Ser Ser Pro Tyr
                165                 170                 175

Gly Asp Thr Glu Gln Lys Leu Ala Ser Tyr Phe Leu Gln Ala Leu Phe
            180                 185                 190

Asn Arg Met Thr Gly Ser Gly Glu Arg Cys Tyr Arg Thr Met Val Thr
        195                 200                 205

Ala Ala Ala Thr Glu Lys Thr Cys Ser Phe Glu Ser Thr Arg Lys Thr
    210                 215                 220

Val Leu Lys Phe Gln Glu Val Ser Pro Trp Ala Thr Phe Gly His Val
```

-continued

```
            225                 230                 235                 240
Ala Ala Asn Gly Ala Ile Leu Glu Ala Val Asp Gly Glu Ala Lys Ile
                245                 250                 255
His Ile Val Asp Ile Ser Ser Thr Phe Cys Thr Gln Trp Pro Thr Leu
                260                 265                 270
Leu Glu Ala Leu Ala Thr Arg Ser Asp Asp Thr Pro His Leu Arg Leu
                275                 280                 285
Thr Thr Val Val Val Ala Asn Lys Phe Val Asn Asp Gln Thr Ala Ser
            290                 295                 300
His Arg Met Met Lys Glu Ile Gly Asn Arg Met Glu Lys Phe Ala Arg
305                 310                 315                 320
Leu Met Gly Val Pro Phe Lys Phe Asn Ile Ile His His Val Gly Asp
                325                 330                 335
Leu Ser Glu Phe Asp Leu Asn Glu Leu Asp Val Lys Pro Asp Glu Val
                340                 345                 350
Leu Ala Ile Asn Cys Val Gly Ala Met His Gly Ile Ala Ser Arg Gly
                355                 360                 365
Ser Pro Arg Asp Ala Val Ile Ser Ser Phe Arg Arg Leu Arg Pro Arg
            370                 375                 380
Ile Val Thr Val Val Glu Glu Ala Asp Leu Val Gly Glu Glu Glu
385                 390                 395                 400
Gly Gly Phe Asp Asp Glu Phe Leu Arg Gly Phe Gly Glu Cys Leu Arg
                405                 410                 415
Trp Phe Arg Val Cys Phe Glu Ser Trp Glu Gly Ser Phe Pro Arg Thr
                420                 425                 430
Ser Asn Glu Arg Leu Met Leu Glu Arg Ala Ala Gly Arg Ala Ile Val
            435                 440                 445
Asp Leu Val Ala Cys Glu Pro Ser Asp Ser Thr Glu Arg Arg Glu Thr
            450                 455                 460
Ala Arg Lys Trp Ser Arg Met Arg Asn Ser Gly Phe Gly Ala Val
465                 470                 475                 480
Gly Tyr Ser Asp Glu Val Ala Asp Val Arg Ala Leu Leu Arg Arg
                485                 490                 495
Tyr Lys Glu Gly Val Trp Ser Met Val Gln Cys Pro Asp Ala Ala Gly
                500                 505                 510
Ile Phe Leu Cys Trp Arg Asp Gln Pro Val Val Trp Ala Ser Ala Trp
            515                 520                 525
Arg Pro Thr
    530

<210> SEQ ID NO 3
<211> LENGTH: 2059
<212> TYPE: DNA
<213> ORGANISM: Arabidopsis thaliana

<400> SEQUENCE: 3
aaaaaaaaaa aatggatact ctctttagac tagtcagtct ccaacaacaa caacaatccg      60
atagtatcat tacaaatcaa tcttcgttaa gcagaacttc caccaccact actggctctc     120
cacaaactgc ttatcactac aactttccac aaaacgacgt cgtcgaagaa tgcttcaact     180
ttttcatgga tgaagaagac ctttcctctt cttcttctca ccacaaccat cacaaccaca     240
acaatcctaa tacttactac ctccttttca ctactcccac ccaataccat cccgccacat     300
catcaacccc ttcctccacc gccgcagccg cagctttagc ctcgccttac tcctcctccg     360
```

-continued

| | |
|---|---|
| gccaccataa tgacccttcc gcgttctcca tacctcaaac tcctccgtcc ttcgacttct | 420 |
| cagccaatgc caagtgggca gactcggtcc ttcttgaagc ggcacgtgcc ttctccgaca | 480 |
| aagacactgc acgtgcgcaa caaatcctat ggacgctcaa cgagctctct tctccgtaat | 540 |
| gaaaaccgct tcattttcct tgtatttgtc tgaggttagg attagaccat tggttgttac | 600 |
| tttcgaattc ttccaattta gttgttactt tcgaattctt ccatctctta gtttactaaa | 660 |
| acaaacttat gtgccccata tttctccaac aatttgttga gtggtagctt acgttttact | 720 |
| gtatacgctt tgcaggtta tatcagcaca accattaatg atggcccggg atgtttgatg | 780 |
| ctaagatgtc ctgacccatc ttgtcttgct gctgttggtc atgatatggt tgacaaatta | 840 |
| gcgtctgaag acgaaaagga gaagtacaac agatattttc ttaggtctta tattgaagac | 900 |
| aacagaaagg taagcagtct agaaaattta tatcacacag actggtatta atgtcgctgg | 960 |
| tcttttattg agcaaaaact ggcttcttac ttcctccaag ctctcttcaa ccgcatgacc | 1020 |
| ggttcaggcg aacgatgcta ccgaaccatg gtaacagctg cagccacaga gaagacttgc | 1080 |
| tccttcgagt caacgcgaaa aactgtacta agttccaag aagttagccc ctgggccacg | 1140 |
| tttggacacg tggcggcaaa cggagcaatc ttggaagcag tagacggaga ggcaaagatc | 1200 |
| cacatcgttg acataagctc cacgttttgc actcaatggc cgactcttct agaagcttta | 1260 |
| gccacaagat cagacgacac gcctcaccta aggctaacca cagttgtcgt ggccaacaag | 1320 |
| tttgtcaacg atcaaacggc gtcgcatcgg atgatgaaag agatcggaaa ccgaatggag | 1380 |
| aaattcgcta ggcttatggg agttcctttc aaatttaaca ttattcatca cgttggagat | 1440 |
| ttatctgagt ttgatctcaa cgaactcgac gttaaaccag acgaagtctt ggccattaac | 1500 |
| tgcgtaggcg cgatgcatgg gatcgcttca cgtggaagcc ctagagacgc tgtgatatcg | 1560 |
| agtttccgac ggttaagacc gaggattgtg acggtcgtag aagaagaagc tgatcttgtc | 1620 |
| ggagaagaag aagtggcttt gatgatgag ttcttgagag ggtttggaga atgtttacga | 1680 |
| tggtttaggg tttgcttcga gtcatgggaa gagagttttc caaggacgag caacgagagg | 1740 |
| ttgatgctag agcgtgcagc gggacgtgcg atcgttgatc ttgtggcttg tgagccgtcg | 1800 |
| gattccacgg agaggcgaga gacagcgagg aagtggtcga ggaggatgag gaatagtggg | 1860 |
| tttggagcgg tggggtatag tgatgaggtg gcggatgatg tcagagcttt gttgaggaga | 1920 |
| tataaagaag gtgtttggtc gatggtacag tgtcctgatg ccgccggaat attcctttgt | 1980 |
| tggagagatc agccggtggt ttgggctagt gcgtggcggc caacgtaaag ggttgttttt | 2040 |
| attttttcat aaggaattc | 2059 |

<210> SEQ ID NO 4
<211> LENGTH: 2502
<212> TYPE: DNA
<213> ORGANISM: Arabidopsis thaliana

<400> SEQUENCE: 4

| | |
|---|---|
| agaagcagag cgtggggttt cttctaataa ttgtagaaga aactgatcat gagaacattt | 60 |
| gatctaccag agatggtgat gactcataag atgtaaatat ctactgcatt atgtctagcc | 120 |
| taggctataa tgtagatttg atcactttct tcattaatta gtttggaatt ttagcatgat | 180 |
| atagcatata tctaaatatg tccgaaactt tcctacatac tagaaaatat ggagagttat | 240 |
| gtaatgtagg tttgcttgtt aatatacaaa ataacatcat catttagttt ttagattttt | 300 |
| tatttattt tttataatgg tgctacgtac gtggcgatca aattattcca attttgagac | 360 |
| ttcgggattt taaacgaaat taaacaatgg gcatgagctc gggggatag acaagattaa | 420 |

-continued

```
tgctttgtat cgagacaaac gagaaaatca tgatgagcct atgcattaag tgccgttggt      480
taattagagg ttcgcatata cataaaccag tagacatatg gataaatatg aacacacaca      540
ccaaaaaagt gggaaatcta ataagtgta gagaataata agtcctcagg tgggagattc       600
aaagagagga caatgaaggg tatatagact ctaaacaaaa atggcatgac ttagtggaga      660
gggttttaaa ttgaaacaag taggattgaa gaacaagaaa acaaagaagc atgccctaga     720
tttctgagat aataattaca cattgctgtt tatataaggt aagagaatat gacacattgg     780
ttggtttctt acgggtaaat gtgaagaaaa aaaatagta atatttgaga aaatctaaaa      840
tagtaaagag gtatatatgg agaagaagag agaaaaggga aaaatagtgg cagagaatgg    900
agagaggtta ggaggcaaag gcaaatgtgg agctttgatg atgttgatgc acgccgtcag    960
cttttcttca cgcctgctcc cactcactca cacctatgaa cattctctct ctattttata    1020
attatattca catgtctcta tgttactatg taaatggtga ccacttaagt atttatatat    1080
catgtatata tcttataggt atcatacaaa atggtcatga aacttttgca atttcaatct    1140
acttgttcat tgtagatgct agcttttcac atgttttgaa aattagtctg gatctgaaat    1200
tctttaatta gcattgtttt gttggtcaac gtttaatttc ttgattattg atgtcaaaaa    1260
ttcagagcgt tcagaactct tacactaatt tcttaaaaat aatcgattaa gagaaaatag    1320
agttttcatg caccagtgtt gatagtaacg tagtcgcgga atgtctaaaa cgattatgag    1380
tttggtgttt tgattggtta gaattggtat tagtaggaca ttctaacttt tttgttagtc    1440
tgttgattta ggatgcgtaa agagtctttt tatttacac cagttgagac ttgggatcga    1500
tagtacttga aacacttggt tggtttcatg tatttggcct atatataaac aaacatcgta    1560
attatatacg gattttttc ggaattttac gccatatctg taagtatata taacatgcat    1620
gtcgttttca aattcatatg atgaacgatc cacgtaagtg ctactactcc tacaatattg    1680
catgagagag atatgtattt ataaatttta ttttgaagaa gaaataagag ggaaggttac    1740
ttgggtggat cgatgtgaaa acaaagaag aaaaagcgaa acccactaag ccattacatg    1800
atatcgacct tcttatcttt ttcctcttta ttttattttt ctcaggactt ttttctactt    1860
aatgaaacct ccaaactatc taactaatac actcccatgt agaataaaga aaattatata    1920
agatattgtt gatattttgt aactagaaaa tatattgct ctgtaatttt tcgtaagtta    1980
aatcaacatt tttcagtaga aacaaatatt actgcaaaaa gtaggatcat tattttgtc    2040 caaaatctca gttagctata gggttgtagt aaaaacaaaa cacattcttg atttgcccca    2100
aaaaataaag agagagaaga atattgttca aaagtggtct cttctctctc taattatgtt    2160
ttcactaaac ccaattagat tcaaacagtc tacaaagtcc aaaagataaa catgggacaa    2220
caattcgatg caaaaaatcc tcttttcatg ctctttttt attctctagt cttttaaatt    2280
actaataaaa actcacaaat ccaccaaacc cattctctac aactcacctt catctagatt    2340
tacccactcc caccgagaaa cacaagaaaa aaaatataca tatataaata tacaagacaa    2400
cacatgatgc tgatgcaata tacacaacaa agtattaaat cttagatatt gtgggtctcc    2460 cttctcta ttcattttct tattcattaa aaaaaaaaa tg                          2502
```

<210> SEQ ID NO 5
<211> LENGTH: 58
<212> TYPE: PRT
<213> ORGANISM: Arabidopsis thaliana

<400> SEQUENCE: 5

```
Pro Phe Ile Arg Phe Thr Gln Leu Thr Ala Asn Gln Ala Ile Leu Glu
1               5                  10                 15

Ala Ile Asn Gly Asn His Gln Ala Ile His Ile Val Asp Phe Asp Ile
            20                  25                 30

Asn His Gly Val Gln Trp Pro Leu Met Gln Ala Leu Ala Asp Arg
        35                  40                  45

Tyr Pro Ala Pro Thr Leu Arg Ile Thr Gly
    50                  55
```

<210> SEQ ID NO 6
<211> LENGTH: 58
<212> TYPE: PRT
<213> ORGANISM: Arabidopsis thaliana

<400> SEQUENCE: 6

```
Pro Tyr Leu Lys Phe Ala His Phe Thr Ala Asn Gln Ala Ile Leu Glu
1               5                  10                 15

Ala Phe Gln Gly Lys Lys Arg Val His Val Ile Asp Phe Ser Met Ser
            20                  25                 30

Gln Gly Leu Gln Trp Pro Ala Leu Met Gln Ala Leu Ala Leu Arg Pro
        35                  40                  45

Gly Gly Pro Pro Val Phe Arg Leu Thr Gly
    50                  55
```

<210> SEQ ID NO 7
<211> LENGTH: 58
<212> TYPE: PRT
<213> ORGANISM: Arabidopsis thaliana

<400> SEQUENCE: 7

```
Pro Tyr Leu Lys Phe Ala His Phe Thr Ala Asn Gln Ala Ile Leu Glu
1               5                  10                 15

Ala Phe Glu Gly Lys Lys Arg Val His Val Ile Asp Phe Ser Met Asn
            20                  25                 30

Gln Gly Leu Gln Trp Pro Ala Leu Met Gln Ala Leu Ala Leu Arg Glu
        35                  40                  45

Gly Gly Pro Pro Thr Phe Arg Leu Thr Gly
    50                  55
```

<210> SEQ ID NO 8
<211> LENGTH: 58
<212> TYPE: PRT
<213> ORGANISM: Arabidopsis thaliana

<400> SEQUENCE: 8

```
Pro Leu Val Lys Phe Ser His Phe Thr Ala Asn Gln Ala Ile Gln Glu
1               5                  10                 15

Ala Phe Glu Lys Glu Asp Ser Val His Ile Ile Lys Leu Asp Ile Met
            20                  25                 30

Gln Gly Leu Gln Trp Pro Gly Leu Phe His Ile Leu Ala Ser Arg Pro
        35                  40                  45

Gly Gly Pro Pro His Val Arg Leu Thr Gly
    50                  55
```

<210> SEQ ID NO 9
<211> LENGTH: 58
<212> TYPE: PRT
<213> ORGANISM: Arabidopsis thaliana

<400> SEQUENCE: 9

```
Pro Trp Ala Thr Phe Gly His Val Ala Ala Asn Gly Ala Ile Leu Glu
1               5                   10                  15

Ala Val Asp Gly Glu Ala Lys Ile His Ile Val Asp Ile Ser Ser Thr
            20                  25                  30

Phe Cys Thr Gln Trp Pro Thr Leu Leu Glu Ala Leu Ala Thr Arg Ser
        35                  40                  45

Asp Asp Thr Pro His Leu Arg Leu Thr Thr
    50                  55
```

<210> SEQ ID NO 10
<211> LENGTH: 20
<212> TYPE: DNA
<213> ORGANISM: Arabidopsis thaliana

<400> SEQUENCE: 10
ggctcacatc atgctagtcc         20

<210> SEQ ID NO 11
<211> LENGTH: 20
<212> TYPE: DNA
<213> ORGANISM: Arabidopsis thaliana

<400> SEQUENCE: 11
gttgaccgac actcttagcc         20

<210> SEQ ID NO 12
<211> LENGTH: 21
<212> TYPE: DNA
<213> ORGANISM: Arabidopsis thaliana

<400> SEQUENCE: 12
tctatacgaa taagagcgtc c       21

<210> SEQ ID NO 13
<211> LENGTH: 21
<212> TYPE: DNA
<213> ORGANISM: Arabidopsis thaliana

<400> SEQUENCE: 13
tattcgcgtc acaatagttc c       21

<210> SEQ ID NO 14
<211> LENGTH: 36
<212> TYPE: DNA
<213> ORGANISM: Arabidopsis thaliana

<400> SEQUENCE: 14
cagtcgacta gtcatatgga tactctcttt agatta    36

<210> SEQ ID NO 15
<211> LENGTH: 17
<212> TYPE: DNA
<213> ORGANISM: Arabidopsis thaliana

<400> SEQUENCE: 15
tgtggaattg tgagccg             17

<210> SEQ ID NO 16
<211> LENGTH: 29
<212> TYPE: DNA
<213> ORGANISM: Arabidopsis thaliana

```
<400> SEQUENCE: 16
cgggatccag aagcagagcg tggggtttc                               29

<210> SEQ ID NO 17
<211> LENGTH: 28
<212> TYPE: DNA
<213> ORGANISM: Arabidopsis thaliana

<400> SEQUENCE: 17
cgggatcctt ttaatgaata agaaaatg                                28
```

US 6,927,320 B1

SHORT-ROOT GENE, PROMOTER, AND USES THEREOF

This invention was made with government support under grant number: GM RO1 43778 awarded by the National Institute of Health. The government may have certain rights in the invention.

1. INTRODUCTION

The present invention generally relates to the SHORT-ROOT (SHR) gene family and their promoters. The invention more particularly relates to ectopic expression of members of the SHORT-ROOT gene family in transgenic plants to artificially modify plant structures. The invention also relates to utilization of the SHORT-ROOT promoter for tissue and organ specific expression of heterologous gene products.

2. BACKGROUND OF THE INVENTION

Asymmetric cell divisions, in which a cell divides to give two daughters with different fates, play an important role in the development of all multicellular organisms. In plants, because there is no cell migration, the regulation of asymmetric cell divisions is of heightened importance in determining organ morphology. In contrast to animal embryogenesis, most plant organs are not formed during embryogenesis. Rather, cells that form the apical meristems are set aside at the shoot and root poles. These reservoirs of stem cells are considered to be the source of all post-embryonic organ development in plants. A fundamental question in developmental biology is how meristems function to generate plant organs.

2.1. Root Development

Root organization is established during embryogenesis. This organization is propagated during postembryonic development by the root meristem. Following germination, the development of the postembryonic root is a continuous process, wherein a series of initials or stem cells continuously divide to perpetuate the pattern established in the embryonic root (Steeves & Sussex, 1972, *Patterns in Plant Development*, Englewood Cliffs, N.J.: Prentice-Hall, Inc.).

2.1.1. *Arabidopsis* Root Development

Due to the organization of the *Arabidopsis* root, it is possible to follow the fate of cells from the meristem to maturity and identify the progenitors of each cell type (Dolan et al., 1993, Development 119:71–84). The *Arabidopsis* root is a relatively simple and well characterized organ. The radial organization of the mature tissues in the *Arabidopsis* root has been likened to tree rings with the epidermis, cortex, endodermis and pericycle forming radially symmetric cell layers that surround the vascular cylinder. See also Dolan et al, 1993, Development 119:71–84. These mature tissues are derived from four sets of stem cells or initials: i) the columella root cap initial; ii) the pericycle/vascular initial; iii) the epidermal/lateral root cap initial; and iv) the cortex/endodermal initial (Dolan et al., 1993, Development 119:71–84). It has been shown that these initials undergo asymmetric divisions (Scheres et al., 1995, Development 121:53–62). The cortex/endodermal initial, for example, first divides anticlinally (in a transverse orientation). This asymmetric division produces another initial and a daughter cell. The daughter cell, in turn, expands and then divides periclinally (in the longitudinal orientation). This second asymmetric division produces the progenitors of the endodermis and the cortex cell lineages.

Furthermore, root radial organization in *Arabidopsis* is produced by three distinct developmental strategies. First, primary roots employ stem cells, wherein initials undergo asymmetric divisions first to regenerate themselves and then to generate the cell lineages of the root. Second, in the embryo, sequential asymmetric divisions subdivide pre-existing tissue to form the cell layers of the embryonic root. Finally, lateral roots are formed by a strategy of cell proliferation that originates in differentiated tissues. Remarkably, within a given species, all three strategies result in roots with a nearly identical radial organization.

2.2. Genes Regulating Root Structure

Mutations that disrupt the asymmetric divisions of the cortex/endodermal initial have been identified and characterized (Benfey et al., 1993, Development 119:57–70; Scheres et al., 1995, Development 121:53–62). short-root (shr) and scarecrow (scr) mutants are missing a cell layer between the epidermis and the pericycle. In both types of mutants, the cortex/endodermal initial divides anticlinally, but the subsequent periclinal division that increases the number of cell layers does not take place (Benfey et al., 1993, Development 119:57–70; Scheres et al., 1995, Development 121:53–62). The defect is first apparent in the embryo and it extends throughout the entire embryonic axis, which includes the embryonic root and hypocotyl (Scheres et al., 1995, Development 121:53–62). This is true also for other radial organization mutants characterized to date, suggesting that radial patterning that occurs during embryonic development may influence the post-embryonic pattern generated by the meristematic initials (Scheres et al., 1995, Development 121:53–62).

In embryos, cortex and endodermis are also formed from the asymmetric division of embryonic ground tissue at the early torpedo stage. This division occurs along the length of the embryonic axis which encompasses the embryonic root and hypocotyl. In both scarecrow and short-root, the embryonic ground tissue fails to undergo the asymmetric division into cortex and endodermis. Hence, these two mutations identify genes required for the asymmetric division that produces cortex and endodermis from ground tissue in the embryo and from the cortex/endodermal initials in primary and lateral roots.

Characterization of the mutant cell layer in shr indicated that two endodermal-specific markers were absent, while the cortex-specific markers were present, indicating that the mutant layer has differentiated attributes only of cortex. Thus, in short-root the initial cell divides transversely, then fails to make the longitudinal division and in the resulting cell only the cortex differentiation program is activated. This suggests that the short-root mutant phenotype is equivalent to the loss of the endodermal cell layer and distinct from the scarecrow phenotype. For SHORT-ROOT, the findings suggest that it is involved in specification of endodermis identity and is also directly or indirectly required for the asymmetric division to form cortex and endodermis. (Benfey et al., 1993, Development 119:57–70).

2.3. Role of SHR in Radial Patterning of the Shoot

SHR functions are not confined to the roots. The hypocotyls of SHR mutants are also missing one of the ground tissue derived cell layers (Scheres, B., et al., 1995, Development 121, 53–62; Fukaki et al., 1998, Plant J. 14, 425–430) but the cellular identities of the remaining cell layers are not known. The absence of normal hypocotyl and shoot endodermis correlates with an agravitropic phenotype in both hypocotyl and shoot inflorescence (Fukaki, et al 1998, Plant J. 14, 425–430). Thus, mutations in the SHR genes lead to a radial pattern deficiency both in the roots and shoots. However, the pattern defects have no effect on root gravitropism. The data suggests that lack of sedimenting amyloplasts in the shr mutant stems is responsible for the shoot agravitropic phenotype (Fukaki, et al, 1998, Plant J. 14, 425–430).

2.4. Geotropism

In plants, the capacity for gravitropism has been correlated with the presence of amyloplast sedimentation. See, e.g., Volkmann and Sievers, 1979, Encyclopedia Plant Physiol., N.S. vol 7, pp. 573–600; Sack, 1991, Intern. Rev. Cytol. 127:193–252; Björkmann, 1992, Adv. Space Res. 12:195–201; Poff et al., in *The Physiology of Tropisms*, Meyerowitz & Somerville (eds); Cold Spring Harbor Laboratory Press, Plainview, N.Y. (1994) pp. 639–664; Barlow, 1995, Plant Cell Environ. 18:951–962. Amyloplast sedimentation only occurs in cells in specific locations at distinct developmental stages. That is, when and where sedimentation occurs is precisely regulated (Sack, 1991, Intern. Rev. Cytol. 127:193–252). In roots, amyloplast sedimentation only occurs in the central (columella) cells of the rootcap; as these cells mature into peripheral cap cells, the amyloplasts no longer sediment (Sack & Kiss, 1989, Amer. J. Bot. 76:454464; Sievers & Braun, in *The Root Cap: Structure and Function*, Wassail et al. (eds.), New York: M. Dekker (1996) pp. 31–49). In stems of many plants, including *Arabidopsis*, amyloplast sedimentation occurs in the starch sheath (endodermis) especially in elongating regions of the stem (von Guttenberg, *Die Physiologischen Scheiden*, Handbuch der Pflanzenanatomie; K. Linsbauer (ed.), Berlin: Gebruder Borntraeger, vol. 5 (1943) p. 217; Sack, 1987, Can. J. Bot. 65:1514–1519; Sack, 1991, Intern. Rev. Cytol. 127:193–252; Caspar & Pickard, 1989, Planta 177:185–197; Volkmann et al., 1993, J. Pl. Physiol. 142:710–6).

Gravitropic mutants have been studied for evidence that proves the role of amyloplast sedimentation in gravity sensing. However, many gravitropic mutations affect downstream events such as auxin sensitivity or metabolism (Masson, 1995, BioEssays 17:119–127). Other mutations seem to affect gene products that process information from gravity sensing. For example, the lazy mutants of higher plants and comparable mutants in mosses can clearly sense and respond to gravity, but the mutations reverse the normal polarity of the gravitropic response (Gaiser & Lomax, 1993, Plant Physiol. 102:339–344; Jenkins et al., 1986, Plant Cell Environ 9:637–644). Other mutations appear to affect gravitropism of specific organs. For example, sgr mutants have defective shoot gravitropism (Fukaki et al., 1996, Plant Physiol. 110:933–943; Fukaki et al., 1996, Plant Physiol. 110:945–955; Fukaki et al., 1996, Plant Res. 109:129–137).

Citation or identification of any reference herein shall not be construed as an admission that such reference is available as prior art to the present invention.

3. SUMMARY OF THE INVENTION

The structure and function of a regulatory gene, SHORT-ROOT (SHR), is described. The SHR gene is expressed specifically in root progenitor tissues of embryos, and in certain tissues of roots and stems. More specifically, SHR is expressed in tissues internal to the endodermis, namely, the pericycle, phloem, protoxylem and procambium.

SHR expression controls cell division of certain cell types in roots, and affects the organization of root and stem. The present invention relates to the SHORT-ROOT (SHR) gene (which encompasses the *Arabidopsis* SHR gene and its orthologs and paralogs), SHR-like genes, SHR gene products, (including, but not limited to, transcriptional products such as mRNAs, antisense and ribozyme molecules, and translational products such as the SHR protein, polypeptides, peptides and fusion proteins related thereto), antibodies to SHR gene products, SHR regulatory regions and the use of the foregoing to improve agronomically valuable plants.

The invention is based, in part, on the discovery, identification and cloning of the gene responsible for the short-root phenotype. The inventors have determined that the mutant cell layer in roots of shr mutants has differentiated characteristics of cortex but not of endodermis. This is consistent with a role for SHR in the regulation of asymmetric cell division and in specification of the identity of endodermis. The inventors have determined also that SHR expression affects the gravitropism of plant aerial structures such as the shoot.

One aspect of the invention relates to the heterologous expression of SHR genes and related nucleotide sequences, and specifically the *Arabidopsis* SHR gene, in stably transformed higher plant species. Modulation of SHR expression levels can be used to advantageously modify root and aerial structures of transgenic plants and enhance the agronomic properties of such plants.

Another aspect of the invention relates to the use of promoters of SHR genes, and specifically the use of the *Arabidopsis* SHR promoter to control the expression of protein and RNA products in plants. Plant SHR promoters have a variety of uses, including, but not limited to, expressing heterologous genes in the embryo, root, root nodule and shoot of transformed plants.

The invention is illustrated by working examples, described infra, which demonstrate the expression, cloning and characterization of the *Arabidopsis* SHR gene.

Structural analysis of the deduced amino acid sequence of *Arabidopsis* SHR protein indicates that SHR encodes a transcription factor. Promoter marker gene analysis and in situ hybridization analysis show highly localized expression of *Arabidopsis* SHR in embryos and roots. Genetic analysis shows SHR expression also affects gravitropism of aerial structures (e.g., stems and shoots). This indicates that SHR is also expressed in those structures.

The present invention further provides compositions and methods for screening compounds that modulate expression within embryos, roots, and shoots. In particular, it provides compositions comprising nucleotides from the SHR promoter, and transcriptionally active fragments thereof, as well as nucleic acids that hybridize under highly stringent conditions to such nucleotides, that control the expression of such SHR promoter. Specifically provided are expression vectors comprising the SHR promoter, and transcriptionally active fragments thereof, operably associated to a heterologous reporter gene, and host cells and transgenic plants containing such vectors. The invention also provides methods for using such vectors, cells and plants for screening candidate molecules for agonists and antagonists of the SHR promoter.

For example, and not by way of limitation, a composition comprising a reporter gene is operatively linked to a SHR promoter. The SHR driven reporter gene is expressed as a transgene in plants. The transgenic plant, and cells derived from embryos, roots or shoots of such transgenic plant, can be used to screen compounds for candidates useful for modulating a SHR promoter. Without being bound by any particular theory, such compounds are likely to interfere with the function of trans-acting factors, such as transcription factors, cis-acting elements, such as promoters and enhancers, as well as any class of post-transcriptional, translational or post-translational compounds involved in modulating a SHR promoter.

In another embodiment, the transgenic plant models of the invention can be used for in vivo screening to test the mechanism of action of candidate drugs for their effect on root or shoot-related disorders.

In addition to tissue specific promoters, the present invention encompasses vectors using inducible promoters. Inducible promoters have the advantage that they can be switched on and off. Therefore, if a cell is stably transfected with a transgene under the control of an inducible promoter, its expression could be controlled over the life-time of the cell.

The invention further provides methods for screening for novel transcription factors that modulate the SHR promoter sequence. Such novel transcription factors identified by this method can be used as targets for treating root or shoot-related disorders.

The various embodiments of the claimed invention presented herein are by way of illustration only and are in no manner intended to limit the scope of the invention.

3.1. Definitions

As used herein, the terms listed below will have the meanings indicated.

| | |
|---|---|
| 35S = | cauliflower mosaic virus promoter for the 35S transcript |
| cDNA = | complementary DNA |
| cis-regulatory element = | A promoter sequence 5' upstream of the TATA box that confers specific regulatory response to a promoter containing such an element. A promoter may contain one or more cis-regulatory elements, each responsible for a particular regulatory response |
| coding sequence = | sequence that encodes a complete or partial gene product (e.g., a complete protein or a fragment thereof) |
| DNA = | deoxyribonucleic acid |
| EST = | expressed sequence tag |
| functional portion = | a functional portion of a promoter is any portion of a promoter that is capable of causing transcription of a linked gene sequence, e.g., a truncated promoter |
| gene fusion = | a gene construct comprising a promoter operably linked to a heterologous gene, wherein said promoter controls the transcription of the heterologous gene |
| gene product = | the RNA or protein encoded by a gene sequence |
| gene sequence = | sequence that encodes a complete gene product (e.g., a complete protein) |
| GUS = | 1,3-β-Glucuronidase |
| gDNA = | genomic DNA |
| heterologous gene = | In the context of gene constructs, a heterologous gene means that the gene is linked to a promoter that said gene is not naturally linked to. The heterologous gene may or may not be from the organism contributing said promoter. The heterologous gene may encode messenger RNA (mRNA), antisense RNA or ribozymes |
| homologous promoter = | a native promoter of a gene that selectively hybridizes to the sequence of a *SHR* gene described herein |
| mRNA = | messenger RNA |
| operably linked = | A linkage between a promoter and gene sequence such that the transcription of said gene sequence is controlled by said promoter |
| ortholog = | related gene in a different plant |
| paralog = | related gene in the same plant |
| RNA = | ribonucleic acid |
| RNase = | ribonuclease |
| *SHR* (italic) = | *SHORT-ROOT* gene or portion thereof, encompasses *SHR* genes and its orthologs and paralogs |
| SHR = | SHORT-ROOT protein |
| *shr* (lower case, italic) = | *short-root* mutant (e.g., *shr1*) |

SHR polypeptides and peptides include deleted or truncated forms of the SHR protein, and fragments corresponding to the SHR motifs described herein.

SHR fusion proteins encompass proteins in which the SHR protein or a SHR polypeptide or peptide is fused to a heterologous protein, polypeptide or peptide.

SHR gene, nucleotides or coding sequences mean nucleotides, e.g., gDNA or cDNA encoding SHR protein, SHR polypeptides, peptides or SHR fusion proteins.

SHR gene products include transcriptional products such as mRNAs, antisense and ribozyme molecules, as well as translational products of the SHR nucleotides described herein, including, but not limited to, the SHR protein, polypeptides, peptides and/or SHR fusion proteins.

SHR promoter means the regulatory region native to the SHR gene in a variety of species, which promotes the organ and tissue specific pattern of SHR expression described herein.

4. BRIEF DESCRIPTION OF THE FIGURES

The following drawings form part of the present specification and are included to further demonstrate certain aspects of the present invention. The invention may be understood better by reference to one or more of these drawings in combination with the detailed description of specific embodiments presented herein.

FIGS. 1A-1H. Phenotype of shr Mutant Plants. (A) Schematic of *Arabidopsis* root anatomy (left). Transverse section showing epidermis, cortex, endodermis, and pericycle surrounding the vascular tissue. In the longitudinal section, the epidermal/lateral root cap initials and the cortex/endodermal initials are shown at the base of their respective cell files. Schematic of division pattern of the cortex/endodermal initial (right). The initial expands and then divides anticlinally to reproduce itself and a daughter cell. The daughter then divides periclinally to produce the progenitors of the endodermis and cortex cell lineages. Abbreviations: C, cortex; Da, daughter cell; E, endodermis; In, initial. Similar schematics were in Di Laurenzio et al., 1996 Cell 86, 423–433. (B) 12-day old wild-type (WT), shr-1, shr-2, shr-3, and shr-4 seedlings grown vertically on nutrient agar medium. Transverse plastic sections of primary root of (C) wild-type and (D) shr-2. CCRC-M2 antibody staining in (E) epidermis and cortex of wild-type and in (B) epidermis and mutant layer of shr-1 primary roots. AX92::GUS expression in mutant layer of (G) a longitudinal optical section and (H) a transverse section of a shr-1 primary root. Abbreviations: ep, epidermis; co, cortex; en, endodermis; m, mutant ground tissue layer in shr.

Figure 2A:
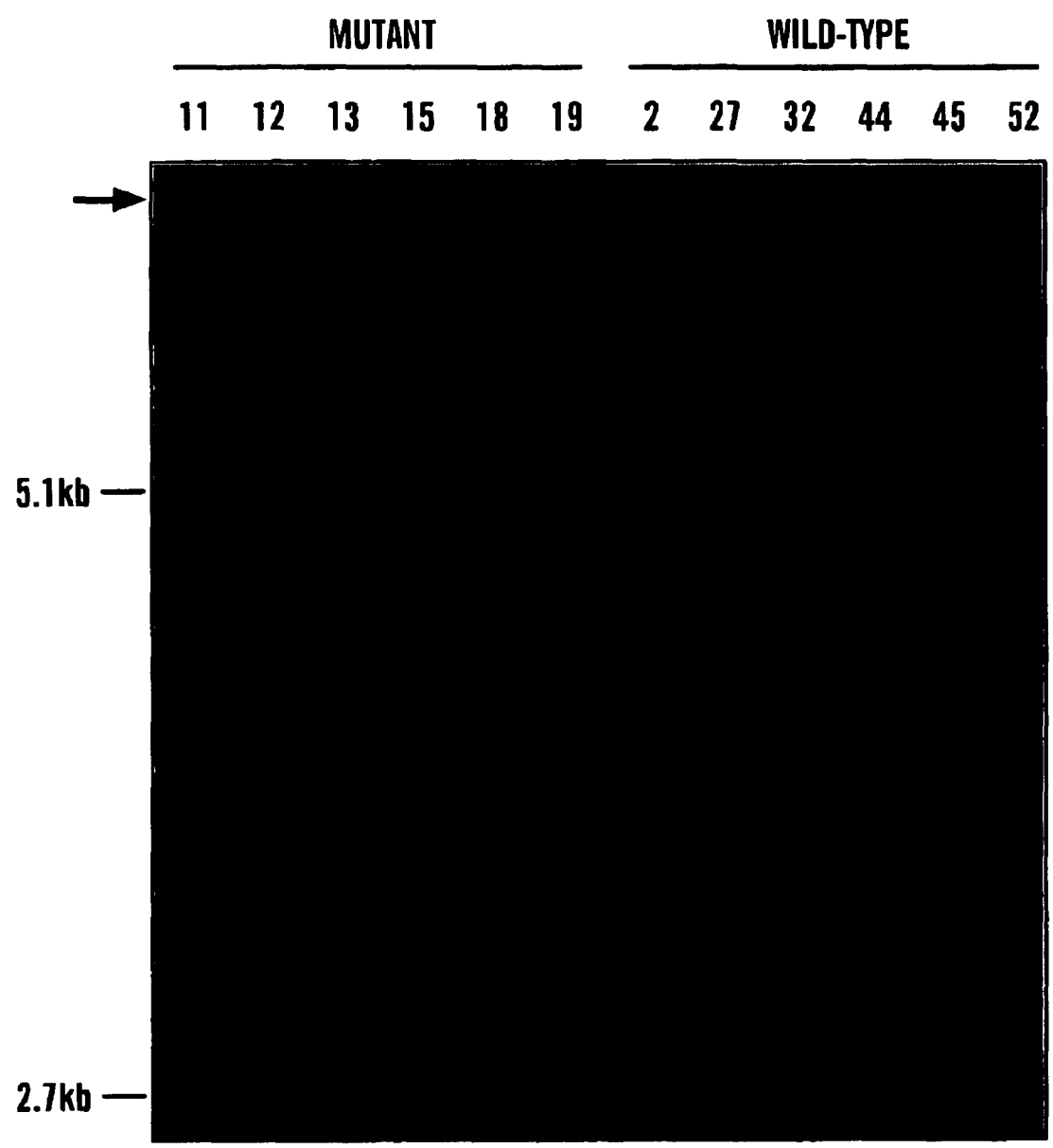

FIGS. 2A-2C. Molecular Cloning of the SHR Gene. (A) The candidate band of En hybridization cosegregating with the shr mutant phenotype is indicated (arrow). A similar size band is found in one of the homozygous wild-type plants (line 52). PCR analysis of the En-SHR junction in this line indicated that the similar molecular weight band does not correspond to the band observed in the homozygous mutants. Numbers above the gel lanes indicate individual plants of the segregating population. Molecular size markers are indicated on the left. (B) Alignment of the deduced amino acid sequence of the "VHIID domains" of five functionally characterized GRAS family genes (Ls: Schumacher et al., 1999, Proc. Natl. Acad. Sci. USA 96, 290–295 (SEQ ID NO: 5); GAI: Peng et al., 1997, Nature 400, 256–261 (SEQ ID NO: 6); RGA: Silverstone et al., 1998, Plant Cell 10, 155–169 (SEQ ID NO: 7); SCR: Di Laurenzio et al., 1996 Cell 86, 423–433 (SEQ ID NO: 8)). Numbers before the sequence indicate the position of the first amino acid of the alignment in the corresponding position in the proteins. Conserved amino acids are shown in bold. SHR (SEQ ID NO: 9) is not highly similar to any other functionally characterized GRAS gene. (C) Mutation sites in shr alleles. Note that shr-4 has a duplication of nucleotide triplets (TAG; underlined) at the En insertion site, while the En insertion in shr-3 did not result in an alteration of the host sequence. shr-1, which has a 50 nucleotide base pair deletion, has a deletion from the threonine at position 408 and includes the cysteine at position 424 of the native SHR sequence. Thus, the remaining sequence is GATGAGTTC . . . ATGGGAAGAGA.

FIGS. 3A-3G. SHR Expression in the Primary Root. (A) SHR RNA accumulation in seedlings. Northern blot analysis was performed with total RNA from 12-day old root tissues hybridized with a SHR gene-specific probe. Lanes are as marked. (B and C) In situ RNA hybridization with a SHR gene-specific probe. (B) Longitudinal and (C) transverse sections of wild-type primary roots hybridized with a digoxigenin-labeled antisense SHR gene-specific probe. Longitudinal optical sections of wild-type roots with (D) confocal laser scanning microscopy of SHR::GFP or (E) histochemical staining (0.5 hr) of SHR::GUS reveal SHR expression in the stele tissue, not in the ground tissue lineage. Confocal images of SHR::GFP expression in (F) shr-3, and (G) shr-1 primary roots. Abbreviations as above except: CEI, cortex/endodermal initial; QC, quiescent center; st, stele.

FIGS. 4A-4F. SHR Expression during Embryogenesis. Longitudinal view of SHR::GFP expression during wild-type embryogenesis. (A) Late globular stage; (B) triangular stage; (C) heart stage; (D) torpedo stage; (E) mature embryonic root; (F) mature embryonic shoot. Abbreviations as above except: cot, cotyledon; hyp, hypophysis; g, ground tissue; gm, ground meristem; my, mid vein of cotyledon; pc, procambium; pd, protoderm; SAM, shoot apical meristem; su, suspensor.

FIGS. 5A-5C. SCR Expression in shr Background. (A) SCR RNA accumulation in seedling roots. Northern blot analysis was performed with total RNA from 12-day-old wild-type, shr-1, and shr-2 root tissues hybridized with a SCR gene-specific probe. The same blot was hybridized with a GDH1 (Melo-Oliveira et al., 1996, Proc. Natl. Acad. Sci. USA 93, 4718–4723) gene-specific probe as a loading control. (B and C) Expression of SCR::GFP in the primary root. GFP expression in (B) wild-type and (C) shr-2 seedling roots harboring the SCR::GFP transgene indicating that the shr mutation results in reduced expression from the SCR promoter. Abbreviations as above.

FIGS. 6A-6H. Primary Root Sector in the Unstable shr-3 Allele. (A, C, and E) Transverse sections and (B, D, F) JIM 13 antibody staining (endodermis and stele marker) of primary roots. (A, B) wildtype; (C, D) shr-3 (mutant phenotype); (E, F) shr-3 with a primary root sector. (F) Red arrows indicate the divided ground tissue cells decorated by JIM13. The red star indicates an undivided ground tissue cell decorated by JIM13. (G and H) Expression of the SCR::GFP reporter gene in the same shr-3 seedling with the primary root sector shown in (E and F). Note that the SCR::GFP reporter gene is expressed strongly only in one cell file on the right side of the root, which corresponds to the divided cells seen in Figures E and F. Abbreviations as above.

Figure 1C:
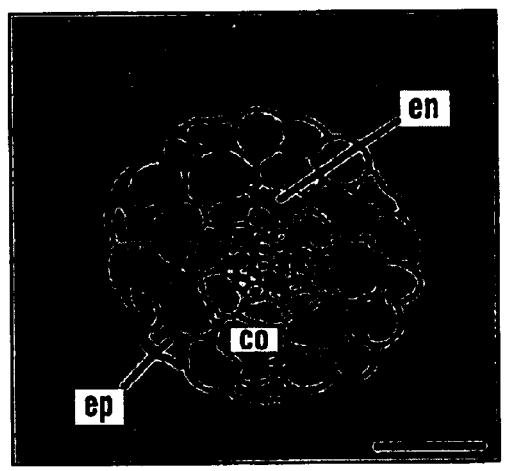
Figure 1D:
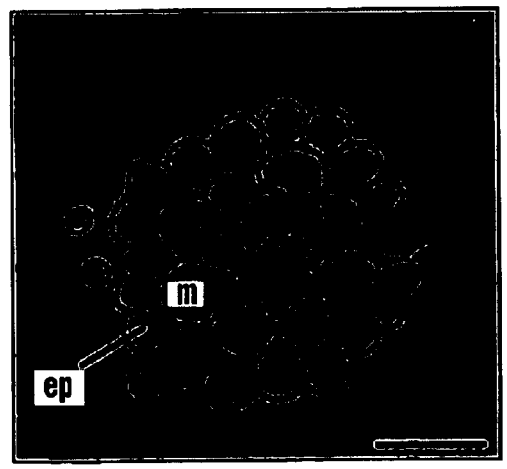
Figure 1E:
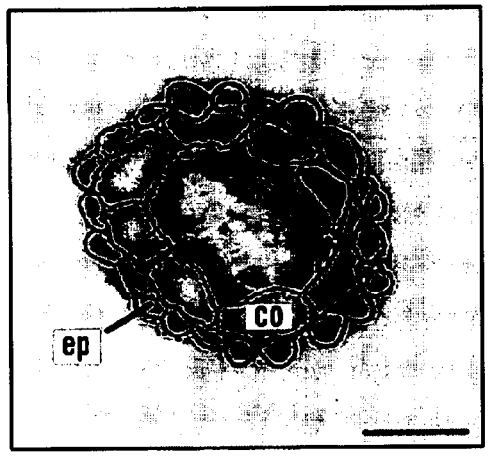
Figure 1F:
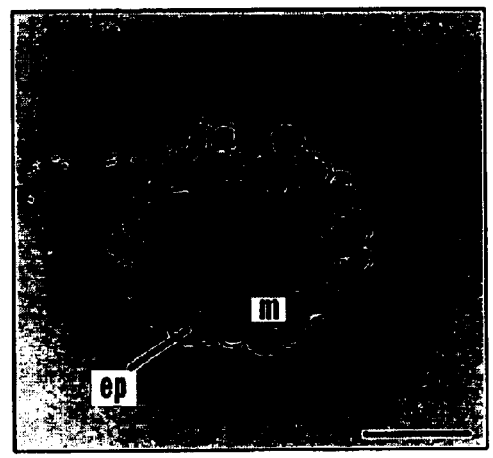
Figure 6A:
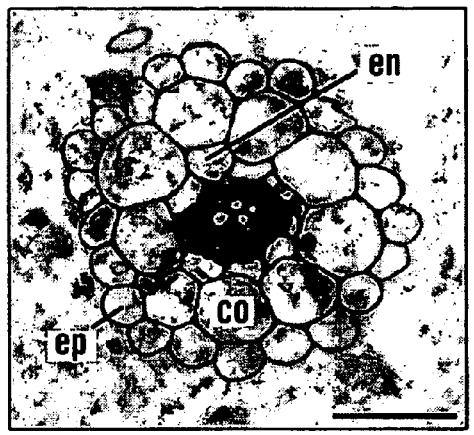
Figure 6B:
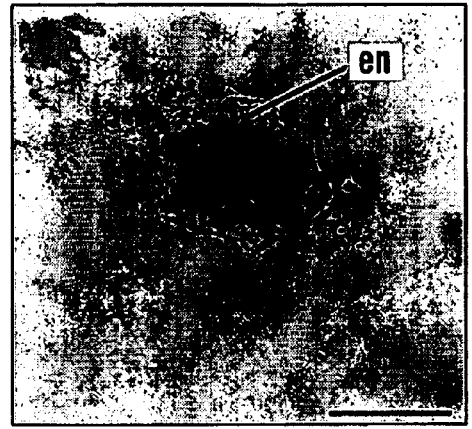
Figure 6C:
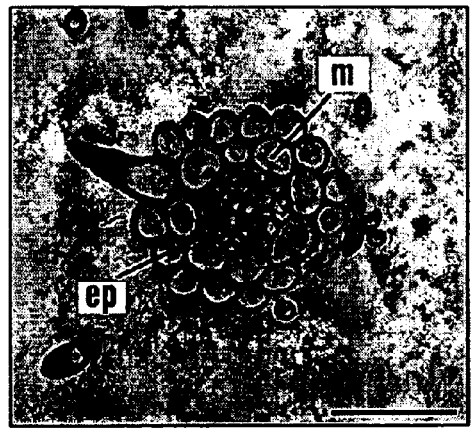
Figure 6D:
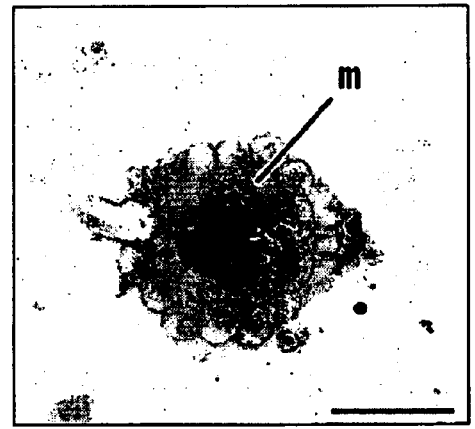

FIGS. 7A-7E. Effects of ectopic expression of SHR. (A) Confocal image of longitudinal optical section of root meristem of 35S::SHR seedling. Note supernumerary cell files as compared to wildtype (FIG. 5B). (B) Transverse section of 35S::SHR seedling root. Compare to wild-type transverse section (FIG. 1C). (C) Ectopic SHR expression results in altered cell specification as revealed by JIM 13 antibody staining of cross-section of 35S::SHR root (serial section of that shown in FIG. 5B). Compare to wildtype JIM 13 staining (FIG. 6B) and shr JIM 13 staining (FIG. 6D). (D) Expression of SHR in 35S::SHR seedling analyzed by in situ hybridization on transverse root section with antisense SHR probe (compare to wildtype expression in FIG. 3C). (E) Expression of SCR in 35S::SHR seedling analyzed by in situ hybridization on transverse root section with antisense SCR probe. In contrast to wildtype, in which expression is restricted to the endodermis (Pysh et al., 1999, Plant J. 18, 111–119), expression in 35S::SHR is detected in all tissues except stele and root cap. Abbreviations as above except: sn, supernumerary cell layers.

FIG. 8. Nucleotide sequence of the *Arabidopsis thaliana* SHR (SEQ ID NO:1). The sequence is from 1 to 2825 base pairs. The mRNA spans 1199 to 2794.

FIG. 9. Deduced amino acid sequence of the *Arabidopsis thaliana* SHR (SEQ ID NO:2). The sequence comprises 531 amino acid residues.

FIG. 10. Nucleotide sequence of the *Arabidopsis thaliana* shr-2 mutant (SEQ ID NO-3). The sequence is from 1 to 2059 base pairs.

FIG. 11. Nucleotide sequence of the *Arabidopsis thaliana* SHR promoter (SEQ ID NO:4). The sequence is from 1 to 2502 base pairs.

Figure 12B:
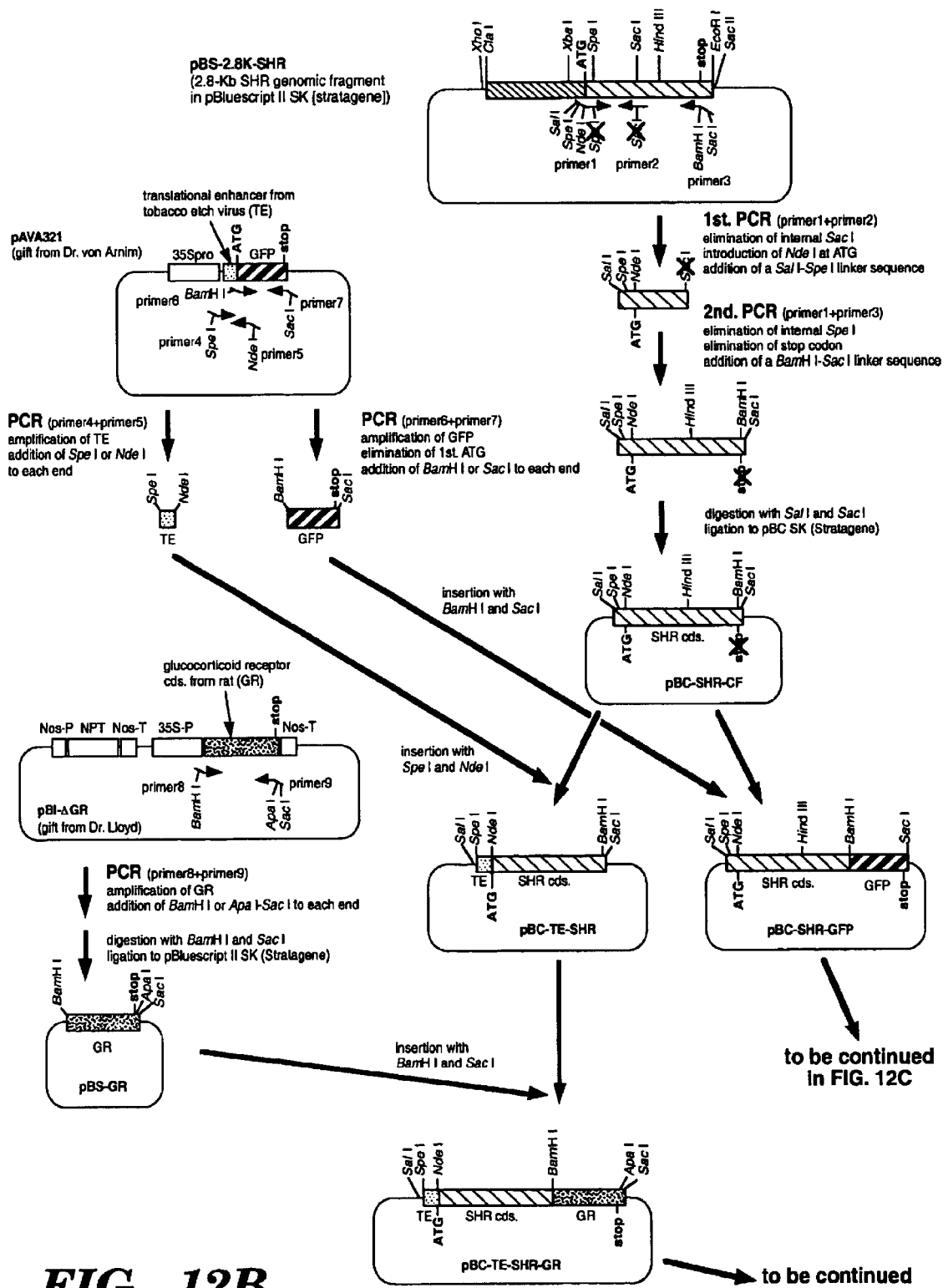

FIGS. 12A-12D. Description of the pBI-SHRpro-SHR-GFP and pBIH-SHRpro-TE-SHR-GR constructs. FIG. 12A represents a schematic of the constructs.

Figure 12C:
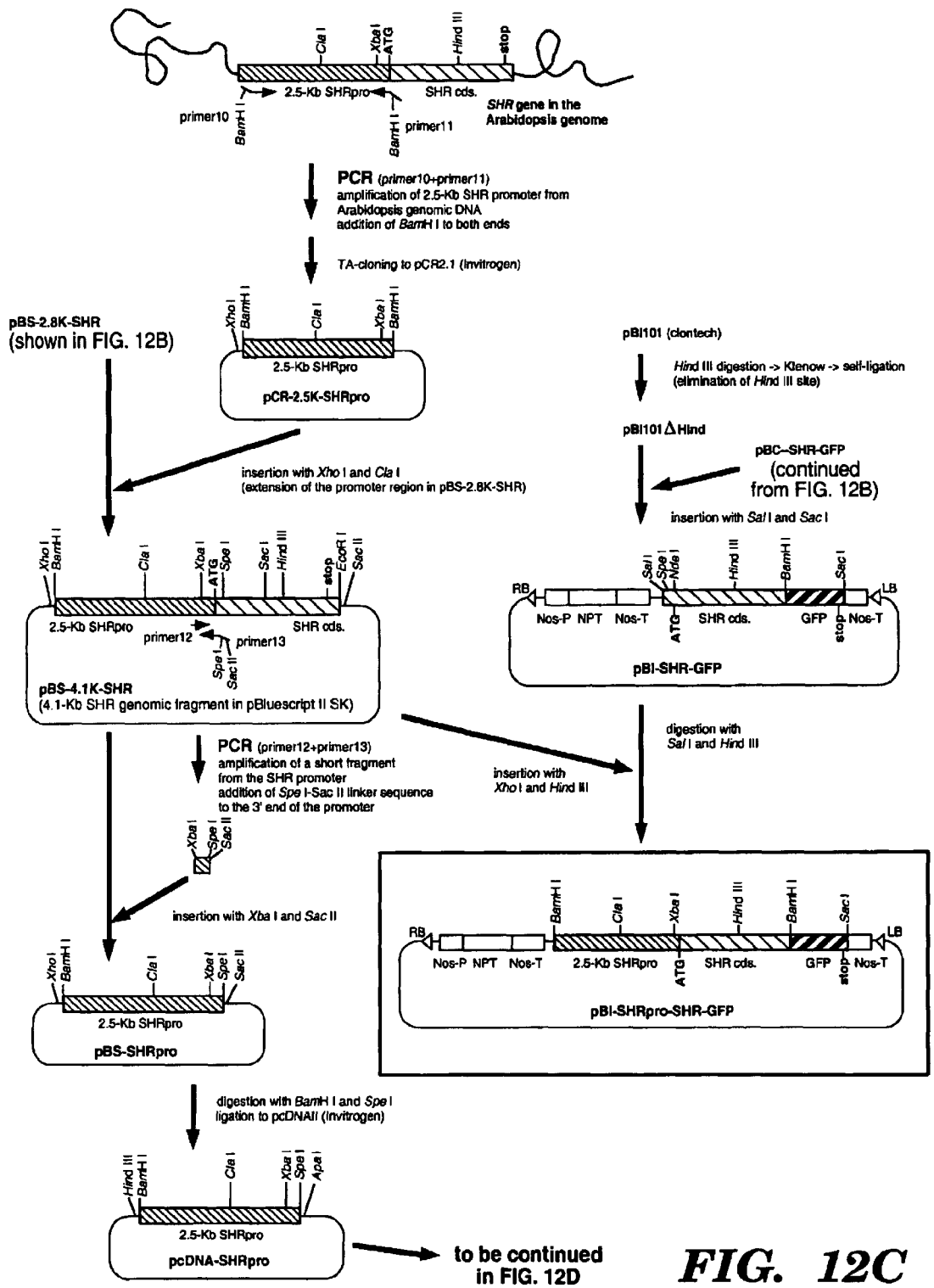
Figure 12D:
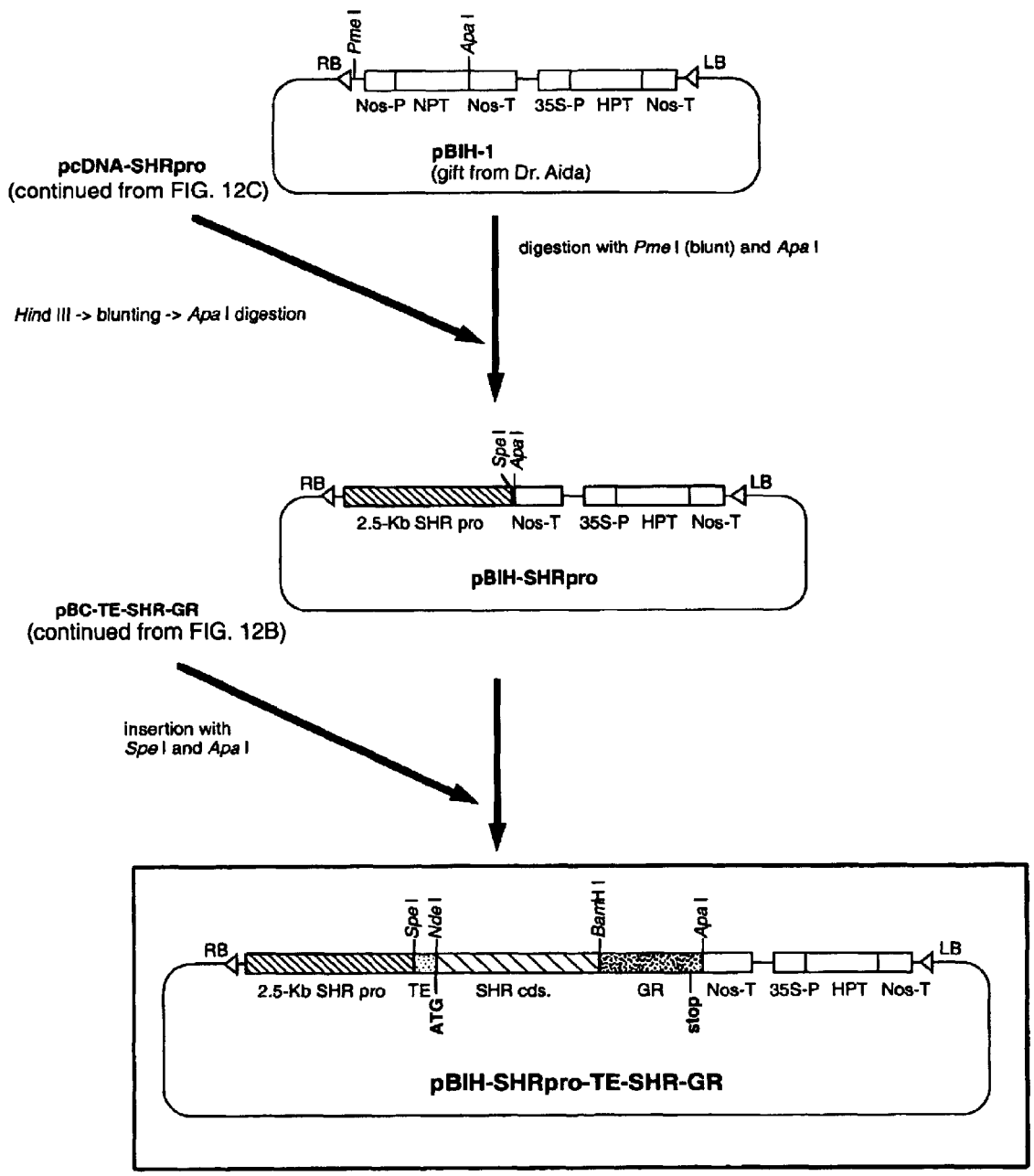

FIGS. 12B-12D represents the method for preparing the constructs.

Figure 13:
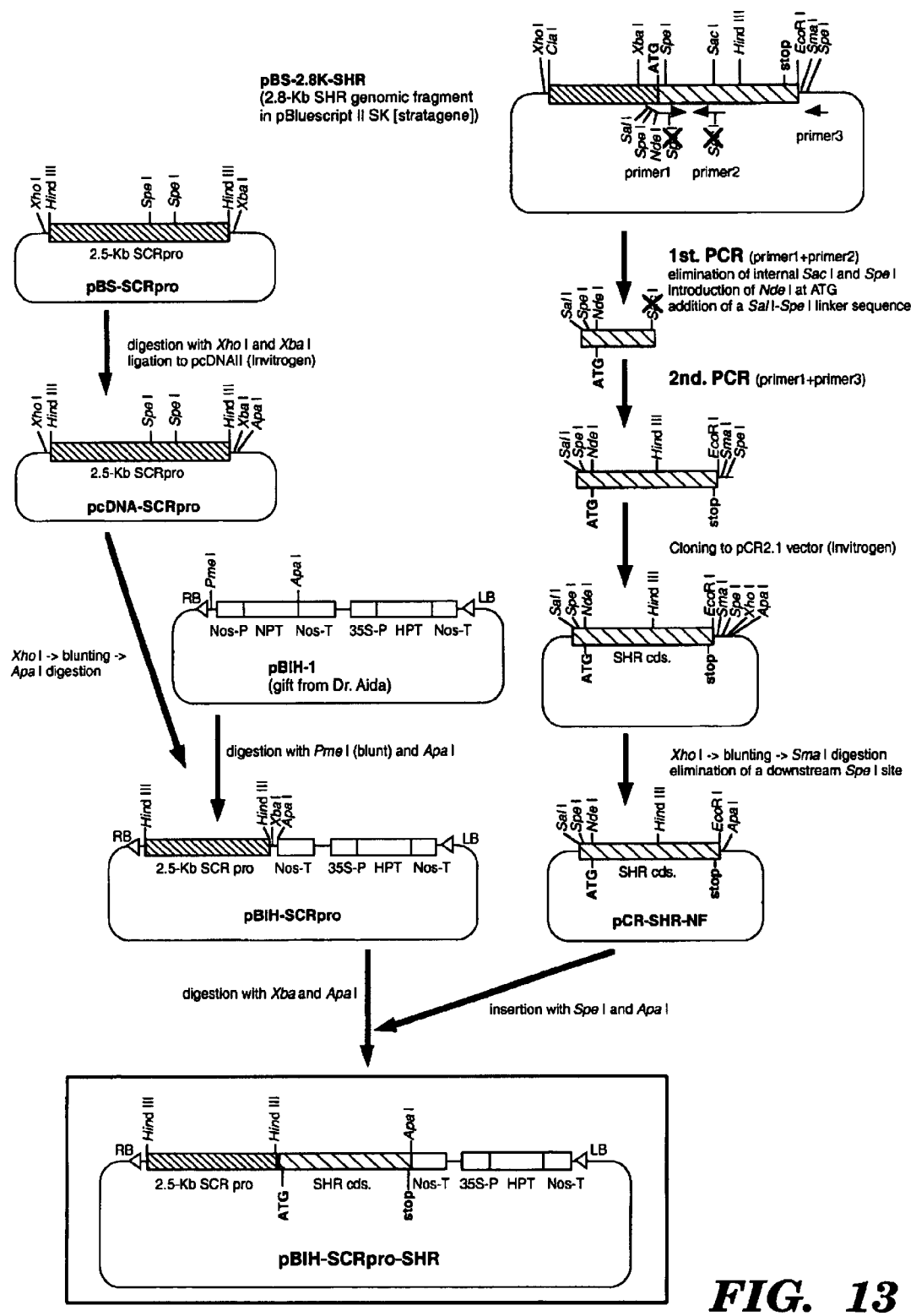

FIG. 13. Description of the pBIH-SCRpro-SHR construct.

Figure 14:
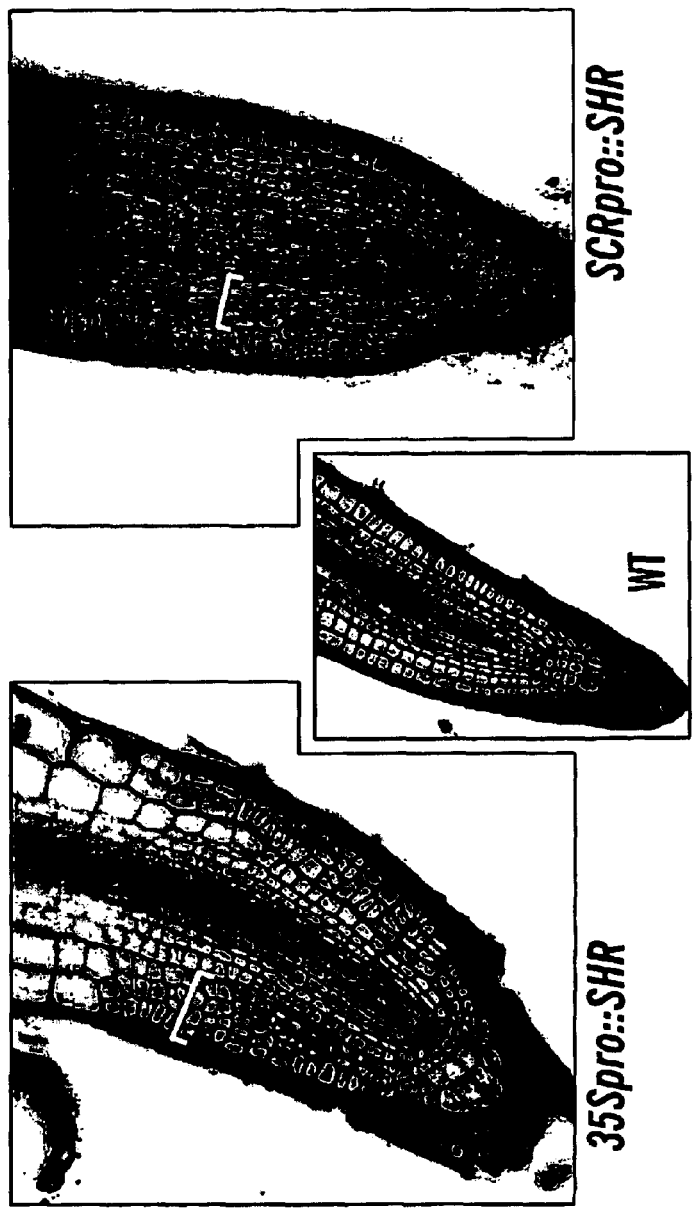

FIG. 14. Results of attaching the promoter region from the SCARECROW gene to the coding region of SHORT-ROOT.

Figure 15:
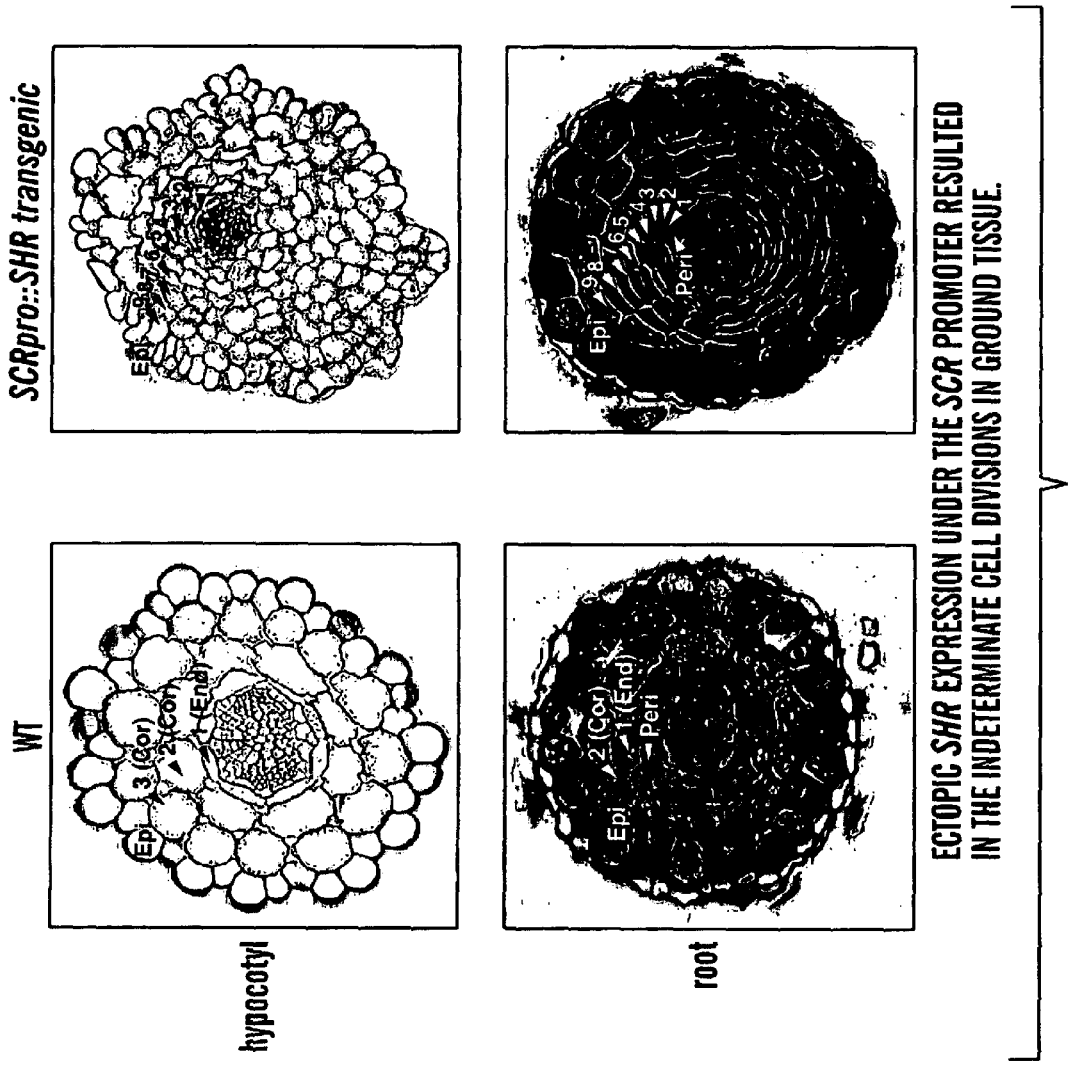

FIG. 15. Cross sections of hypocotyl and root comparing wildtype and plants with the pB1H—SCRpro-SHR construct.

FIG. 16. Staining for the Casparian Strip in wildtype and plants with the pB1H—SCRpro-SHR construct.

5. DETAILED DESCRIPTION OF THE INVENTION

The invention relates to the SHORT-ROOT (SHR) gene; SHORT-ROOT-like (SHL) genes, SHR gene products, including, but not limited to, transcriptional products such as mRNAs, antisense and ribozyme molecules, translational products such as the SHR protein, polypeptides, peptides and fusion proteins related thereto; antibodies to SHR gene products; SHR regulatory regions; and the use of the foregoing to improve agronomically valuable plants.

In summary, the data described herein show the identification of SHR, a gene involved in the regulation of a specific asymmetric division, in controlling gravitropic response in aerial structures, and in controlling pattern formation in roots. Sequence analysis shows that the SHR protein has many hallmarks of transcription factors. In situ and 115 marker line expression studies show that SHR is expressed in the tissues internal to the endodermis, namely, the pericycle, phloem and procambium. Together, these findings indicate that the SHR gene regulates key events that establish the asymmetric division that generates separate cortex and endodermal cell lineages, and that affect tissue organization of roots.

Genetic analysis indicates that SHR expression affects gravitropism of plant stems, hypocotyls and shoots. This indicates that SHR is expressed also in these aerial structures of plants.

The SHR genes and promoters of the present invention have a number of important agricultural uses. The SHR promoters of the invention may be used in expression constructs to express desired heterologous gene products only in stele tissues (vasculature and pericycle) in the root of transgenic plants transformed with such constructs. For example, SHR promoters may be used to express disease resistance genes such as lysozymes, cecropins, maganins or thionins for anti-bacterial protection, or the pathogenesis-related (PR) proteins such as glucanases and chitinases for anti-fungal protection. SHR promoters also may be used to express a variety of pest resistance genes in the aforementioned plant structures and tissues. Examples of useful gene products for controlling nematodes or insects include *Bacillus thuringiensis* endotoxins, protease inhibitors, coliagenases, chitinase, glucanases, lectins and glycosidases.

Gene constructs that express or ectopically express SHR, and the SHR-suppression constructs of the invention, may be used to alter the root and/or stem structure, and the gravitropism of aerial structures of transgenic plants. Since SHR regulates root cell divisions, overexpression of SHR can be used to increase division of certain cells in roots and thereby form thicker and stronger roots. Thicker and stronger roots are beneficial in preventing plant lodging. Conversely, suppression of SHR expression can be used to decrease cell division in roots and thereby form thinner roots. Thinner roots are more efficient in uptake of soil nutrients. Since SHR affects gravitropism of aerial structures, overexpression of SHR may be used to develop "straighter" transgenic plants that are less susceptible to lodging.

Further, the SHR gene sequence may be used as a molecular marker for a quantitative trait, e.g., a root or gravitropism trait, in molecular breeding of crop plants.

Further, the ability to control the length and internal architecture of plant roots would serve several critical problems of modern agriculture and biotechnology. Federal regulations governing fertilizer use combined with the high energy cost of fertilizer production are forcing the AgBiotech industry to look for alternatives to intensive agriculture practices. One attractive alternative is to engineer plants so that they will be better able to utilize the nutrients found in particular locations. Frequently this means that the plant's root must grow deep into the soil. The problem is that most crop plants today have been bred for relatively shallow roots because that is where all of the nutrients are located when high fertilizer levels are used. If one were able to control the length of a plant's roots and one knew where in the soil particular nutrients are at higher concentration (this is frequently already known), then one could program the plant to grow roots to the proper length for optimal utilization of the natural resources.

Another use for controlled root length is in phytoremediation. Plants are currently being engineered to be used in toxic waste clean-up. For them to work effectively, their roots must penetrate to the sites of the toxic substances. Thus, plants in which roots can be programmed to grow to particular lengths would be of great use in this area of biotechnology. A similar argument could be made for plants used in erosion control.

In the presently described unstable allele of short-root, roots of vastly different sizes growing from the same plant have been obtained. Longer roots have been correlated with restoration of SHORT-ROOT activity in some cells in those roots. This indicates that controlling SHORT-ROOT gene activity is one means of controlling root length. Thus, armed with the SHR sequence disclosed herein, one has the potential of altering root length in specific ways by altering the activity level of the SHORT-ROOT gene.

The ability to control of the internal architecture of root and shoot could also have potential for agriculture improvement. The endodermis is a specialized tissue in both root and shoot. In the root, it is the site of formation of the Casparian strip, a water impermeable barrier that forces selective uptake of nutrients and ions. In the shoot, it is the location of sedimenting amyloplasts which are part of the gravity sensing apparatus. Since SHORT-ROOT expression is necessary for differentiation of endodermal cells in both root and shoot, regulating SHORT-ROOT activity in the root could result in plants better able to assimilate water-soluble nutrients. Regulating SHORT-ROOT activity in the shoot could result in plants that are less liable to fall over ("lodge") as a result of environmental stress.

5.1. Polynucleotides and Nucleic Acids of the Invention

The present invention relates to nucleic acid molecules that encode polypeptides referred to as SHR. In accordance with the invention, any nucleotide sequence which encodes the amino acid sequence of the SHR gene product can be used to generate recombinant molecules which direct the expression of SHR. Additionally, the invention also relates to a fusion polynucleotide between a SHR coding sequence and a second coding sequence for a heterologous protein.

In order to clone full length homologous cDNA sequences from any species encoding the entire SHR cDNA or to clone family members or variant forms such as allelic variants, labeled DNA probes made from fragments corresponding to any part of the cDNA sequences disclosed herein may be used to screen a cDNA library derived from a cell or tissue type believed to express SHR, e.g. roots. More specifically, oligonucleotides corresponding to either the 5' or 3' terminus of the coding sequence may be used to obtain longer nucleotide sequences. Briefly, the library may be plated out to yield a maximum of 30,000 pfu for each 150 mm plate. Approximately 40 plates may be screened. The plates are incubated at 37° C. until the plaques reach a diameter of 0.25 mm or are just beginning to make contact with one another (3–8 hours). Nylon filters are placed onto the soft top agarose and after 60 seconds, the filters are peeled off and floated on a DNA denaturing solution consisting of 0.4N sodium hydroxide. The filters are then immersed in neutralizing solution consisting of 1M Tris HCl, pH 7.5, before being allowed to air dry. The filters are prehybridized in casein hybridization buffer containing 10% dextran sulfate, 0.5M NaCl, 50 mM Tris HCl, pH 7.5, 0.1% sodium pyrophosphate, 1% casein, 1% SDS, and denatured salmon sperm DNA at 0.5 mg/ml for 6 hours at 60° C. The radiolabelled probe is then denatured by heating to 95° C. for 2 minutes and then added to the prehybridization solution containing the filters. The filters are hybridized at 60° C. for 16 hours. The filters are then washed in 1× wash mix (10× wash mix contains 3M NaCl, 0.6M Tris base, and 0.02M EDTA) twice for 5 minutes each at room temperature, then in 1× wash mix containing 1% SDS at 60° C. for 30 minutes, and finally in 0.3× wash mix containing 0.1% SDS at 60° C. for 30 minutes. The filters are then air dried and exposed to x-ray film for autoradiography.

After developing, the film is aligned with the filters to select a positive plaque. If a single, isolated positive plaque cannot be obtained, the agar plug containing the plaques will be removed and placed in lambda dilution buffer containing 0.1M NaCl, 0.01M magnesium sulfate, 0.035M Tris HCl, pH 7.5, 0.01% gelatin. The phage may then be replated and rescreened to obtain single, well isolated positive plaques. Positive plaques may be isolated and the cDNA clones sequenced using primers based on the known cDNA sequence. This step may be repeated until a full length cDNA is obtained.

It may be necessary to screen multiple cDNA libraries from different tissues to obtain a full length cDNA. In the event that it is difficult to identify cDNA clones encoding the complete 5' terminal coding region, an often encountered situation in cDNA cloning, the RACE (Rapid Amplification of cDNA Ends) technique may be used. RACE is a proven PCR-based strategy for amplifying the 5' end of incomplete cDNAs. 5'-RACE-Ready RNA synthesized from human placenta containing a unique anchor sequence is commercially available (Clontech). To obtain the 5' end of the cDNA, PCR is carried out on 5'-RACE-Ready cDNA using the provided anchor primer and the 3' primer. A secondary PCR is then carried out using the anchored primer and a nested 3' primer according to the manufacturer's instructions. Once obtained, the full length cDNA sequence may be translated into amino acid sequence and examined for certain landmarks such as a continuous open reading frame flanked by translation initiation and termination sites, a potential signal sequence and finally overall structural similarity to the SHR gene sequences disclosed herein.

Alternatively, a labeled probe may be used to screen a genomic library derived from any organism of interest using appropriate stringent conditions as described, infra.

Isolation of a SHR coding sequence or a homologous sequence may be carried out by the polymerase chain reactions (PCR) using two degenerate oligonucleotide primer pools designed on the basis of the SHR coding sequences disclosed herein. The template for the reaction may be cDNA obtained by reverse transcription (RT) of mRNA prepared from, for example, plant cell lines or tissues known or suspected to express a SHR gene allele.

The PCR product may be subcloned and sequenced to ensure that the amplified sequences represent the sequences of a SHR coding sequence. The PCR fragment may then be used to isolate a full length cDNA clone by a variety of methods. For example, the amplified fragment may be labeled and used to screen a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source. An RT reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated.

A cDNA clone of a mutant or allelic variant of the SHR gene may be isolated, for example, by using PCR. In this case, the first cDNA strand may be synthesized by hybridizing an oligo-dT oligonucleotide to mRNA isolated from tissue known or suspected to be expressed in a plant putatively carrying the mutant SHR allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant SHR allele to that of the normal SHR allele, the mutation(s) responsible for the loss or alteration of function of the mutant SHR gene product can be ascertained.

Alternatively, a genomic library can be constructed using DNA obtained from a plant suspected of or known to carry a mutant SHR allele, or a cDNA library can be constructed using RNA from a tissue known, or suspected, to express a mutant SHR allele. An unimpaired SHR gene or any suitable fragment thereof may then be labeled and used as a probe to identify the corresponding mutant SHR allele in such libraries. Clones containing the mutant SHR gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant SHR allele in a plant suspected of or known to carry such a mutant allele. In this manner, gene products made by the putatively mutant tissue may be expressed and screened using standard antibody screening techniques in conjunction with antibodies raised against the normal SHR gene product, as described, below. (For screening techniques, see, for example, Harlow and Lane, eds., 1988, "Antibodies: A Laboratory Manual", Cold Spring Harbor Press, Cold Spring Harbor.)

In cases where a SHR mutation results in an expressed gene product with altered function (e.g., as a result of a missense), a polyclonal set of anti-SHR gene product antibodies are likely to cross-react with the mutant SHR gene product. Library clones detected via their reaction with such labeled antibodies can be purified and subjected to sequence analysis according to methods well known to those of skill in the art.

Functional equivalents of the SHR gene product include any plant gene product that regulates plant embryo or root development, or, preferably, that regulates root cell division or root tissue organization, or affects gravitropism of plant aerial structures (e.g., stems and hypocotyls). Functional equivalents of the SHR gene product include naturally occurring SHR gene products, and mutant SHR gene products, whether naturally occurring or engineered.

As used herein, the terms nucleic acid, polynucleotide and nucleotide are interchangeable and refer to any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages.

The terms nucleic acid, polynucleotide and nucleotide also specifically includes nucleic acids composed of bases other than the five biologically occurring bases (adenine, guanine, thymine, cytosine and uracil). For example, a polynucleotide of the invention might contain at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

Furthermore, a polynucleotide of the invention may comprise at least one modified sugar moiety selected from the group including but not limited to arabinose, 2-fluoroarabinose, xylulose, and hexose.

It is not intended that the present invention be limited by the source of the polynucleotide. The polynucleotide can be from a plant or non-plant, derived from any recombinant source, synthesized in vitro or by chemical synthesis. The nucleotide may be DNA or RNA and may exist in a double-stranded, single-stranded or partially double-stranded form.

Nucleic acids useful in the present invention include, by way of example and not limitation, oligonucleotides such as antisense DNAs and/or RNAs; ribozymes; DNA for gene therapy; DNA and/or RNA chimeras; various structural forms of DNA including single-stranded DNA, double-stranded DNA, supercoiled DNA and/or triple-helix DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, *Oligonucleotide Synthesis: A Practical Approach*, IRL Press, Oxford, England). RNAs may be produce in high yield via in vitro transcription using plasmids such as SP65 (Promega Corporation, Madison, Wis.).

The present invention includes any mRNA transcript encoded by the SHR genes of the invention, including in particular, mRNA transcripts resulting from alternative splicing or processing of mRNA precursors.

In some circumstances, as where increased nuclease stability is desired, nucleic acids having modified internucleoside linkages may be preferred. Nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($—CH_2—S—CH_2$), dimethylene-sulfoxide ($—CH_2—SO—CH_2$), dimethylene-sulfone ($—CH_2—SO_2—CH_2$), 2'-O-alkyl, and 2'-deoxy-2'-fluoro phosphorothioate internucleoside linkages are well known in the art (see Uhlmann et al., 1990, *Chem. Rev.* 90:543–584; Schneider et al., 1990, *Tetrahedron Lett.* 31:335 and references cited therein).

In some embodiments of the present invention, the nucleotide is an α-anomeric nucleotide. An α-anomeric nucleotide forms specific double-stranded hybrids with complementary RNA in which, contrary to the usual β-units, the strands run parallel to each other (Gautier et al., 1987, Nucl. Acids Res. 15:6625–6641). The nucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

The nucleic acids may be purified by any suitable means, as are well known in the art. For example, the nucleic acids can be purified by reverse phase or ion exchange HPLC, size exclusion chromatography or gel electrophoresis. Of course, the skilled artisan will recognize that the method of purification will depend in part on the size of the DNA to be purified.

The nucleic acid itself may act as a therapeutic agent, such as for example an antisense DNA that inhibits mRNA translation, or the nucleic acid may encode a SHR capable of inducing a therapeutic affect upon expression in a plant. These gene products can potentially function as therapeutic molecules in a variety of contexts, for example, as cytokines, chemokines, signaling molecules, membrane proteins, transcription factors, intracellular proteins, cytokine binding proteins, and the like.

The invention also relates to isolated or purified polynucleotides having at least 12 nucleotides (i.e., a hybridizable portion) of a SHR coding sequence or its complement. In other embodiments, the polynucleotides contain at least 25 (continuous) nucleotides, 50 nucleotides, 100 nucleotides, 150 nucleotides, or 200 nucleotides of a SHR coding sequence, or a full-length SHR coding sequence. Nucleic acids can be single or double stranded. Additionally, the invention relates to polynucleotides that selectively hybridize to a complement of the foregoing coding sequences. In preferred embodiments, the polynucleotides contain at least 12, 25, 50, 100, 150 or 200 nucleotides or the entire length of a SHR coding sequence.

In a specific embodiment, a polynucleotide which hybridizes to a SHR coding sequence or its complement under conditions of low stringency is provided. By way of example and not limitation, exemplary conditions of low stringency are as follows (Shilo and Weinberg, 1981, Proc. Natl. Acad. Sci. USA 78:6789–6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which may be used are well known in the art (e.g., as employed for cross-species hybridizations).

In another specific embodiment, a polynucleotide which hybridizes to a SHR coding sequence or its complement under conditions of high stringency is provided. By way of example and not limitation, exemplary conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10⁶ cpm of ³²P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

In another specific embodiment, a polynucleotide which hybridizes to a SHR coding sequence or its complement under conditions of moderate stringency is provided. Exemplary conditions of moderate stringency are as follows: Filters containing DNA are pretreated for 6 h at 55° C. in a solution containing 6×SSC, 5× Denhart's solution, 0.5% SDS and 100 µg/ml denatured salmon sperm DNA. Hybridizations are carried out in the same solution and 5–20×10⁶ cpm ³²P-labeled probe is used. Filters are incubated in hybridization mixture for 18–20 h at 55° C., and then washed twice for 30 minutes at 60° C. in a solution containing 1×SSC and 0.1% SDS. Filters are blotted dry and exposed for autoradiography. Other conditions of moderate stringency which may be used are well-known in the art.

Other conditions of high stringency which may be used are well known in the art. In general, for probes between 14 and 70 nucleotides in length the melting temperature (TM) is calculated using the formula: $Tm(°C.)=81.5+16.6(\log[\text{monovalent cations (molar)}])+0.41(\% G+C)-(500/N)$ where N is the length of the probe. If the hybridization is carried out in a solution containing formamide, the melting temperature is calculated using the equation $Tm(°C.)=81.5+16.6(\log[\text{monovalent cations (molar)}])+0.41(\% G+C)-(0.61\% \text{ formamide})-(500/N)$ where N is the length of the probe. In general, hybridization is carried out at about 20–25 degrees below Tm (for DNA-DNA hybrids) or 10–15 degrees below Tm (for RNA-DNA hybrids).

The invention also encompasses nucleotide sequences that encode a mutant of SHR, peptide fragments of SHR, truncated forms of SHR, and SHR fusion proteins. These include, but are not limited to, nucleotide sequences encoding mutant SHR proteins and polypeptides; polypeptides or peptides corresponding to one or more domains of SHR, e.g., the bZIP, VHIID or leucine heptad domains, or portions of these domains; truncated forms of SHR, in which one or more of the domains is deleted; or a truncated, nonfunctional SHR. Nucleotides encoding fusion proteins may include, but are not limited to, full length SHR sequences, truncated forms of SHR, or nucleotides encoding peptide fragments of SHR fused to an unrelated protein or peptide, such as for example, a SHR domain fused to an Ig Fc domain which increases the stability and half life of the resulting fusion protein (e.g., SHR-Ig); or an enzyme such as a fluorescent protein or a luminescent protein which can be used as a marker.

The invention encompasses highly related gene homologs, e.g., orthologs and paralogs, of the SHR encoding polynucleotide sequences described above. Highly related gene homologs are polynucleotides encoding proteins that are at least 30% identical, or at least 40% identical, preferably 50% identical, more preferably 60% identical, even more preferably 70% or even 80% identical, and most preferably 90% identical, at the amino acid level to the disclosed SHR proteins.

SHR genes share substantial amino acid sequence similarities at the protein level and nucleotide sequence similarities in their encoding genes. The term "substantially similar" or "substantial similarity" when used herein with respect to two amino acid sequences means that the two sequences have at least 75% identical residues, preferably at least 85% identical residues and most preferably at least 95% identical residues. The same term when used herein with respect to two nucleotide sequences means that the two sequences have at least 70% identical residues, preferably at least 85% identical residues and most preferably at least 95% identical residues. Determining whether two sequences are substantially similar may be carried out using any methodologies known to one skilled in the art, preferably using computer assisted analysis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical overlapping positions/total # of positions×100). In one embodiment, the two sequences are the same length.

The determination of percent identity between two sequences also can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the NBLAST and XBLAST programs of Altschul, et al. (1990) *J. Mol. Biol.* 215:403410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389–3402. Alternatively, PSI-Blast can be used to perform an iterated search which detects distant relationships between molecules (Id.). When utilizing BLAST, Gapped BLAST and PSI-Blast programs, the default parameters of the respective programs (e.g., XBLAST and NBLAST) can be used (see http://www.ncbi.nlm.nih.gov). Another preferred, non-limiting example of a mathematical algorithm utilized for the comparison of sequences is the algorithm of Myers and Miller, (1988) *CABIOS* 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12 and a gap penalty of 4 can be used. In an alternate embodiment, alignments can be obtained using the NA_MULTIPLE_ALIGNMENT 1.0 program, using a GapWeight of 5 and a GapLengthWeight of 1.

The percent identity between two sequences can be determined using techniques similar to those described above, with or without allowing gaps. In calculating percent identity, typically only exact matches are counted.

Moreover, SHR genes show highly localized expression in embryos and, particularly, roots. Such expression patterns may be ascertained by Northern hybridizations and in situ hybridizations using antisense probes.

The invention also encompasses (a) DNA vectors that contain any of the foregoing SHR coding sequences and/or their complements (i.e., antisense); (b) DNA expression vectors that contain any of the foregoing SHR coding sequences operatively associated with a regulatory element that directs the expression of the coding sequences; (c) genetically engineered host cells that contain any of the foregoing SHR coding sequences operatively associated with a regulatory element that directs the expression of the coding sequences in the host cell; and (d) genetically engineered host cells that express an endogenous SHR gene under the control of an exogenously introduced regulatory element (i.e., gene activation).

5.1.1. Isolation of SHR Genes

The following methods can be used to obtain SHR and SHL genes and coding sequences from a wide variety of plants, including, but not limited to, *Arabidopsis thaliana, Zea mays, Nicotiana tabacum, Daucus carota, Oryza, Glycine max, Lemna gibba* and *Picea abies*.

Nucleotide sequences encoding a SHR gene, a SHL gene or portions thereof may be obtained by PCR amplification of plant genomic DNA or cDNA. Useful cDNA sources include "free" cDNA preparations (i.e., the products of cDNA synthesis) and cloned cDNA in cDNA libraries. Root cDNA preparations or libraries are particularly preferred.

The amplification may use, as the 5'-primer (i.e., forward primer), a degenerate oligonucleotide that corresponds to a segment of a known SHR amino acid sequence, preferably from the amino-terminal region. The 3'-primer (i.e., reverse primer) may be a degenerate oligonucleotide that corresponds to a distal segment of the same known SHR amino acid sequence (i.e., carboxyl to the sequence that corresponds to the 5'-primer). For example, the amino acid sequence of the *Arabidopsis* SHR protein (SEQ ID NO:2) may be used to design useful 5' and 3' primers. Preferably, the primers correspond to segments in the VHIID domain of the SHR protein (see FIG. 2). The sequence of the optimal degenerate oligonucleotide probe corresponding to a known amino acid sequence may be determined by standard algorithms known in the art. See for example, Sambrook et al., *Molecular Cloning: A Laboratory Manual*, 2nd ed., Cold Spring Harbor Laboratory Press, Cold Spring Harbor, N.Y., Vol 2 (1989).

Further, for amplification from cDNA sources, the 3'-primer may be an oligonucleotide comprising an 3' oligo (dT) sequence. The amplification also may use as primers nucleotide sequences of SHR and SHL genes or coding sequences.

PCR amplification can be carried out, e.g., by use of a Perkin-Elmer Cetus thermal cycler and Taq polymerase (Gene Amp™). One can choose to synthesize several different degenerate primers for use in the PCR reactions. It also is possible to vary the stringency of hybridization conditions used in priming the PCR reactions, to allow for greater or lesser degrees of nucleotide sequence similarity between the degenerate primers and the corresponding sequences in the cDNA library. One of ordinary skill in the art will know that the appropriate amplification conditions and parameters depend, in part, on the length and base composition of the primers and that such conditions may be determined using standard formulae. Protocols for executing all PCR procedures discussed herein are well known to those skilled in the art, and may be found in references such as Gelfand, 1989, *PCR Technology, Principles and Applications for DNA Amplification*, H. A. Erlich, ed., Stockton Press, New York; and *Current Protocols In Molecular Biology*, Vol. 2, Ch. 15, Ausubel et al., eds 1988, New York, Wiley & Sons, Inc.

A PCR amplified sequence may be molecularly cloned and sequenced. The amplified sequence may be utilized as a probe to isolate genomic or cDNA clones of a SHR gene, as described below. This, in turn, will permit the determination of a SHR gene's complete nucleotide sequence, including its promoter, the analysis of its expression, and the production of its encoded protein, as described infra.

A SHR or SHL gene coding sequence also may be isolated by screening a plant genomic or cDNA library using a SHR or SHL nucleotide sequence as a hybridization probe. For example, the whole, or a segment, of the *Arabidopsis* SHR nucleotide sequence may be used. Alternatively, a SHR or SHL gene may be isolated from such libraries using a degenerate oligonucleotide that corresponds to a segment of a SHR amino acid sequence as a probe. For example, a degenerate oligonucleotide probe corresponding to a segment of the *Arabidopsis* SHR amino acid sequence may be used.

In preparation of cDNA libraries, total RNA is isolated from plant tissues, preferably roots. Poly(A)+ RNA is isolated from the total RNA, and cDNA prepared from the poly(A)+ RNA, all using standard procedures. See, for example, Sambrook et al., *Molecular Cloning: A Laboratory Manual*, 2d ed., Vol. 2 (1989). The cDNAs may be synthesized with a restriction enzyme site at their 3'-ends by using an appropriate primer and further have linkers or adaptors attached at their 5'-ends to facilitate the insertion of the cDNAs into suitable cDNA cloning vectors. Alternatively, adaptors or linkers may be attached to the cDNAs after the completion of cDNA synthesis.

In preparation of genomic libraries, plant DNA is isolated and fragments are generated, some of which will encode parts of the whole SHR protein. The DNA may be cleaved at specific sites using various restriction enzymes. Alternatively, one may use DNase in the presence of manganese to fragment the DNA, or the DNA can be physically sheared, as for example, by sonication. The DNA fragments can then be separated according to size by standard techniques, including, but not limited to, agarose and polyacrylamide gel electrophoresis, column chromatography and sucrose gradient centrifugation.

The genomic DNA or cDNA fragments can be inserted into suitable vectors, including, but not limited to, plasmids, cosmids, bacteriophages lambda or $T_4$, and yeast artificial chromosome (YAC) [See, for example, Sambrook et al., *Molecular Cloning: A Laboratory Manual*, 2d ed., Cold Spring Harbor Laboratory Press, Cold Spring Harbor, N.Y. (1989); Glover, D. M (ed.), *DNA Cloning: A Practical Approach*, MRL Press, Ltd., Oxford, U.K., Vols. I and II (1985)].

The identity of a cloned or amplified SHR gene sequence can be verified by comparing the amino acid sequences of its three open reading frames with the amino acid sequence of a SHR gene (e.g., *Arabidopsis* SHR protein [SEQ ID No:2]). A SHR gene or coding sequence encodes a protein or polypeptide whose amino acid sequence is substantially similar to that of a SHR protein or polypeptide. The identity of the cloned or amplified SHR gene sequence may be further verified by examining its expression pattern, which should show highly localized expression in the embryo and/or root of the plant from which the SHR gene sequence was isolated.

Comparison of the amino acid sequences encoded by a cloned or amplified sequence may reveal that it does not contain the entire SHR gene or its promoter. In such a case, the cloned or amplified SHR gene sequence may be used as a probe to screen a genomic library for clones having inserts that overlap the cloned or amplified SHR gene sequence. A complete SHR gene and its promoter may be reconstructed by splicing the overlapping SHR gene sequences.

5.2. Products Encoded by The Polynucleotides Disclosed Herein

In accordance with the invention, a SHR polynucleotide which encodes full length SHR polypeptides, mutant polypeptides, peptide fragments of SHR, SHR fusion proteins or functional equivalents thereof, may be used to generate recombinant DNA molecules that direct the expression of SHR polypeptides, mutant polypeptides, SHR peptide fragments, SHR fusion proteins or a functional equivalent thereof, in appropriate host cells. Such polynucleotides, as well as other polynucleotides which selectively hybridize to at least a part of such SHR polynucleotides or their complements, may also be used to produce SHR polypeptides or they may be used in nucleic acid hybridization assays, such as Southern and Northern blot analyses, etc. The polypeptide products encoded by such polynucleotides may be naturally occurring or altered by molecular manipulation of the coding sequence.

Moreover, SHR proteins, polypeptides and peptide fragments, mutated, truncated or deleted forms of SHR and/or SHR fusion proteins can be prepared for a variety of uses, including, but not limited to, the generation of antibodies, as reagents in assays, the identification of other cellular gene products involved in regulation of root development; etc.

Due to the inherent degeneracy of the genetic code, other DNA sequences which encode substantially the same or functionally equivalent SHR amino acid sequences may be used in the practice of the invention for the cloning and expression of SHR proteins. Such DNA sequences include those which are capable of hybridizing to the SHR coding sequences disclosed herein or their complementary sequences under low, moderate or high stringency conditions as described in Section 5.1.

SHR translational products include, but are not limited to, those proteins and polypeptides encoded by the SHR gene sequences described in Section 5.1, above. The invention encompasses proteins that are functionally equivalent to the SHR gene products described in Section 5.1. Such a SHR gene product may contain one or more deletions, additions or substitutions of SHR amino acid residues within the amino acid sequence encoded by any one of the SHR gene sequences described, above, in Section 5.1, but which result in a silent change, thus producing a functionally equivalent SHR gene product.

Amino acid substitutions may be made on the basis of similarity in polarity, charge, solubility, hydrophobicity, hydrophilicity and/or the amphipathic nature of the residues involved. For example, nonpolar (hydrophobic) amino acids include alanine, leucine, isoleucine, valine, proline, phenylalanine, tryptophan and methionine; polar neutral amino acids include glycine, serine, threonine, cysteine, tyrosine, asparagine and glutamine; positively charged (basic) amino acids include arginine, lysine and histidine; and negatively charged (acidic) amino acids include aspartic acid and glutamic acid.

"Functionally equivalent", as utilized herein, refers to a protein capable of exhibiting a substantially similar in vivo activity as the endogenous SHR gene products encoded by the SHR gene sequences described in Section 5.1, above. Alternatively, "functionally equivalent" may refer to peptides capable of regulating gene expression in a manner substantially similar to the way in which the corresponding portion of the endogenous SHR gene product would.

The nucleotide sequences of the invention may be engineered in order to alter a SHR coding sequence for a variety of ends, including but not limited to, alterations which modify processing and expression of the gene product. For example, mutations may be introduced using techniques which are well known in the art, e.g., site-directed mutagenesis, to insert new restriction sites, to alter glycosylation patterns, phosphorylation, etc. Alterations may also affect one or more biologic activities of SHR. For example, cysteine residues can be deleted or substituted with another amino acid to eliminate disulfide bridges.

Based on the domain organization of the SHR protein, a large number of SHR mutant polypeptides can be constructed by rearranging the nucleotide sequences that encode the SHR domains.

In another embodiment of the invention, a SHR coding sequence, a modified SHR coding sequence or a truncated SHR coding sequence corresponding to a specific domain may be ligated to a heterologous sequence to produce a fusion protein. For example, for screening of peptide libraries for molecules that bind SHR, it may be useful to encode a chimeric SHR protein expressing a heterologous epitope that is recognized by a commercially available antibody. A fusion protein may also be engineered to contain a cleavage site located between a SHR sequence and the heterologous protein sequence, so that the SHR may be cleaved and separated from the heterologous moiety. A heterologous moiety includes, but is not limited to, immunoglobulin constant domain which prolongs in vivo half life of the fusion protein, a cell surface molecule which anchors the fusion protein to the cell membrane, and a detectable label such as a fluorescent protein or an enzyme.

In a specific embodiment of the invention, the nucleotide sequence of SHR could be synthesized in whole or in part, using chemical methods well known in the art. See, for example, Caruthers et al., 1980, *Nuc. Acids Res. Symp. Ser.* 7:215–233; Crea and Horn, 180, *Nuc. Acids Res.* 9(10) :2331; Matteucci and Caruthers, 1980, *Tetrahedron Letter* 21:719; and Chow and Kempe, 1981, *Nuc. Acids Res.* 9(12):2807–2817. Alternatively, the polypeptide itself could be produced using chemical methods to synthesize a SHR amino acid sequence in whole or in part. For example, peptides can be synthesized by solid phase techniques, cleaved from the resin, and purified by preparative high performance liquid chromatography. (e.g., see Creighton, 1983, *Proteins Structures And Molecular Principles*, W.H. Freeman and Co., N.Y. pp. 50–60). The composition of the synthetic peptides may be confirmed by amino acid analysis or sequencing (e.g., the Edman degradation procedure; see Creighton, 1983, *Proteins, Structures and Molecular Principles*, W.H. Freeman and Co., N.Y., pp. 34–49).

In a specific embodiment of the invention, a polypeptide containing at least 10 (continuous) amino acids of the SHR protein is provided. In other embodiments, the polypeptide may contain at least 20 or 50 amino acids. In specific embodiments, such polypeptides do not contain more than 100, 150 or 200 amino acids. Derivatives or analogs of the polypeptides include, but are not limited to, molecules containing regions that are substantially homologous to the SHR protein or fragments thereof (e.g. in various embodiments, at least 60% or 70% or 80% or 90% or 95% identity over an amino acid sequence of identical size or when compared to an aligned sequence in which the alignment is done by a computer homology program known in the art) or product encoded by a polynucleotide that is capable of hybridizing to a naturally-occurring coding sequence, under highly stringent, moderately stringent, or low stringent conditions. Percent homology may be determined, for example, by comparing sequence information using the BLAST or GAP programs described supra.

The present invention also encompasses SHR polypeptides that are coded for by alternatively spliced SHR mRNA transcripts.

The derivatives and analogs of SHR protein can be produced by various methods known in the art. The manipulations which result in their production can occur at the nucleic acid or protein level. For example, a cloned coding sequence can be modified by any of numerous strategies known in the art (Maniatis, T., 1990, Molecular Cloning, A Laboratory Manual, 2d ed., Cold Spring Harbor Laboratory, Cold Spring Harbor, New York). The sequence can be cleaved at appropriate sites with restriction endonuclease(s), followed by further enzymatic modification if desired, isolated, and ligated in vitro. In the production of a polynucleotide encoding a derivative or analog, care should be taken to ensure that the modified coding sequence remains within the same translational reading frame as the antigen, uninterrupted by translational stop signals, in the coding region where the functional domain is encoded.

Additionally, the coding sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:6551), use of TAB® linkers (Pharmacia), and the like.

The invention also encompasses mutant SHR proteins and polypeptides that are not functionally equivalent to the gene products described in Section 5.1. Such a mutant SHR protein or polypeptide may contain one or more deletions, additions or substitutions of SHR amino acid residues within the amino acid sequence encoded by any one the SHR gene sequences described above in Section 5.1., and which result in loss of one or more functions of the SHR protein (e.g., recognition of a specific nucleic sequence, binding of a transcription factor, etc.), thus producing a SHR gene product not functionally equivalent to the wild-type SHR protein.

While random mutations can be made to SHR DNA (using random mutagenesis techniques well known to those skilled in the art) and the resulting mutant SHRs tested for activity, site-directed mutations of the SHR gene and/or coding sequence can be engineered (using site-directed mutagenesis techniques well known to those skilled in the art) to generate mutant SHRs with increased function, (e.g., resulting in improved root formation), or decreased function (e.g., resulting in suboptimal root function).

Manipulations may also be made at the protein level. Included within the scope of the invention are protein fragments or other derivatives or analogs which are differentially modified during or after translation, e.g., by glycosylation, acetylation, phosphorylation, amidation, derivatization by known protecting/blocking groups, proteolytic cleavage, linkage to a heterologous polypeptide or another antigen. Any of numerous chemical modifications may be carried out by known techniques, including but not limited to, specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives can be chemically synthesized. Non-classical amino acids (i.e., amino acids not encoded by the genetic code) or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In a specific embodiment, the derivative is a chimeric or fusion protein containing SHR or a fragment thereof joined at its amino- or carboxy-terminus to a heterologous protein via a peptide bond. Alternatively, the proteins are connected by a flexible polylinker such as Gly-Cys-Gly or Gly-Gly-Gly-Gly-Ser repeated 1 to 3 times (Bird et al., 1988, Science 242:423426; Chaudhary et al., 1990, Proc. Nat'l. Acad. Sci. U.S.A. 87:1066–1070). In one embodiment, such a chimeric protein is produced by recombinant expression of a nucleic acid encoding the protein (a SHR coding sequence joined in-frame to a coding sequence for another antigen or a heterologous protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of the SHR coding sequence fused to any other coding sequences may be constructed.

In another specific embodiment, the derivative is a molecule comprising a region of homology with SHR. By way of example, in various embodiments, a protein region can be considered "homologous" to a second protein region when the amino acid sequence of the first region is at least 30%, 40%, 50%, 60%, 70%, 75%, 80%, 90%, or 95% identical, when compared to any sequence in the second region of an equal number of amino acids as the number contained in the first region or when compared to an aligned sequence of the second region that has been aligned by a computer homology program known in the art e.g., the BLAST program described above.

5.3. Production of SHR Polypeptides

While the SHR polypeptides and peptides can be chemically synthesized (e.g., see Creighton, 1983, Proteins: Structures and Molecular Principles, W.H. Freeman & Co., N.Y.) large polypeptides derived from SHR and the full length SHR may advantageously be produced by recombinant DNA technology using techniques well known to those skilled in the art for expressing nucleic acid sequences.

Methods which are well known to those skilled in the art can be used to construct expression vectors containing the SHR coding sequence and appropriate transcriptional/translational control signals. These methods include in vitro recombinant DNA techniques, synthetic techniques and in vivo recombination/genetic recombination. (See, for example, the techniques described in Sambrook et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.). RNA capable of encoding SHR polypeptide may also be chemically synthesized (Gait, ed., 1984, Oligonucleotide Synthesis, IRL Press, Oxford).

A variety of host-expression vector systems may be utilized to express the SHR gene products of the invention. Such host-expression systems represent vehicles by which the SHR gene products of interest may be produced and subsequently recovered and/or purified from the culture or plant (using purification methods well known to those skilled in the art), but also represent cells which may, when transformed or transfected with the appropriate nucleotide coding sequences, exhibit the SHR protein of the invention in situ.

These include, but are not limited to, microorganisms such as bacteria (e.g., *E. coli, B. subtilis*) transformed with recombinant bacteriophage DNA, plasmid DNA or cosmid DNA expression vectors containing SHR protein coding sequences; yeast (e.g., *Saccharomyces, Pichia*) transformed with recombinant yeast expression vectors containing the SHR protein coding sequences; insect cell systems infected with recombinant virus expression vectors (e.g., baculovirus) containing the SHR protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing SHR protein coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter; the cytomegalovirus promoter/enhancer; etc.).

Depending on the host/vector system utilized, any of a number of suitable transcription and translation elements, including constitutive and inducible promoters, may be used in the expression vector. For example, when cloning in bacterial systems, inducible promoters such as pL of bacteriophage A, plac, ptrp, ptac (ptrp-lac hybrid promoter; cytomegalovirus promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll $\alpha/\beta$ binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the SHR coding sequence, SV40-, BPV- and EBV-based vectors may be used with an appropriate selectable marker.

5.3.1. Expression Systems

In bacterial systems a number of expression vectors may be advantageously selected depending upon the use intended for the expressed SHR product. For example, when large quantities of SHR protein are to be produced for the generation of antibodies, screening peptide libraries or formulating pharmaceutical compositions, vectors which direct the expression of high levels of fusion protein products that are readily purified may be desirable. Such vectors include but are not limited to the *E. coli* expression vector pUR278 (Ruther et al., 1983, EMBO J. 2:1791), in which the SHR coding sequence may be ligated into the vector in frame with the lacZ coding region so that a hybrid protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In one such embodiment of a bacterial system, full length cDNA sequences are appended with in-frame Bam HI sites at the amino terminus and Eco RI sites at the carboxyl terminus using standard PCR methodologies (Innis et al., 1990, supra) and ligated into the pGEX-2TK vector (Pharmacia, Uppsala, Sweden). The resulting cDNA construct contains a kinase recognition site at the amino terminus for radioactive labeling and glutathione S-transferase sequences at the carboxyl terminus for affinity purification (Nilsson, et al., 1985, EMBO J. 4: 1075; Zabeau and Stanley, 1982, *EMBO J.* 1: 1217).

The recombinant constructs of the present invention may include a selectable marker for propagation of the construct. For example, a construct to be propagated in bacteria preferably contains an antibiotic resistance gene, such as one that confers resistance to kanamycin, tetracycline, streptomycin or chloramphenicol. Suitable vectors for propagating the construct include plasmids, cosmids, bacteriophages or viruses, to name but a few.

In addition, the recombinant constructs may include plant-expressible, selectable or screenable marker genes for isolating, identifying or tracking plant cells transformed by these constructs. Selectable markers include, but are not limited to, genes that confer antibiotic resistance, (e.g., resistance to kanarnycin or hygromycin) or herbicide resistance (e.g., resistance to sulfonylurea, phosphinothricin or glyphosate). Screenable markers include, but are not be limited to, genes encoding β-glucuronidase (Jefferson, 1987, Plant Mol. Biol. Rep. 5:387405), luciferase (Ow et al., 1986, Science 234:856–859) and B protein that regulates anthocyanin pigment production (Goff et al., 1990, EMBO J. 9:2517–2522).

In embodiments of the present invention which utilize the *Agrobacterium tumefacien* system for transforming plants, the recombinant constructs may additionally comprise at least the right T-DNA border sequences flanking the DNA sequences to be transformed into the plant cell. Alternatively, the recombinant constructs may comprise the right and left T-DNA border sequences flanking the DNA sequence. The proper design and construction of such T-DNA based transformation vectors are well known to those skilled in the art.

In yeast, a number of vectors containing constitutive or inducible promoters may be used (Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast *Saccharomyces*, 1982, Eds. Strathern et al., Cold Spring Harbor Press, Vols. I and II).

In cases where plant expression vectors are used, the expression of the SHR coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, R1 plasmids, plant virus vectors, direct DNA transformation, microinjection, electroporation, etc. (Weissbach & Weissbach, 1988, Methods for Plant Molecular Biology, Academic Press, NY, Section VIII, pp. 421463; and Grierson & Corey, 1988, Plant Molecular Biology, 2d Ed., Blackie, London, Ch. 7–9).

An alternative expression system which could be used to express SHR is an insect system. In one such system, *Autographa californica* nuclear polyhedrosis virus (AcNPV) is used as a vector to express foreign genes. The virus grows in *Spodoptera frugiperda* cells. The SHR coding sequence may be cloned into non-essential regions (for example the polyhedron gene) of the virus and placed under control of an AcNPV promoter (for example the polyhedron promoter). Successful insertion of the SHR coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., see Smith et al., 1983, J. Viol. 46:584; Smith, U.S. Pat. No. 4,215,051).

In mammalian host cells, a number of viral based expression systems may be utilized. In cases where an adenovirus is used as an expression vector, the SHR coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing SHR in infected hosts (e.g., See Logan & Shenk, 1984, Proc. Natl. Acad. Sci. USA 81:3655–3659). Alternatively, a vector derived from vaccinia virus can be used, which would typically make use of the vaccinia 7.5K promoter (See, e.g., Mackett et al., 1982, Proc. Natl. Acad. Sci. USA 79:7415–7419; Mackett et al., 1984, J. Virol. 49:857–864; Panicali et al., 1982, Proc. Natl. Acad. Sci. USA 79:4927–4931). Regulatable expression vectors such as the tetracycline repressible vectors may also be used to express the coding sequences in a controlled fashion.

Specific initiation signals may also be required for efficient translation of inserted SHR coding sequences. These signals include the ATG initiation codon and adjacent sequences. In cases where the entire SHR gene, including its own initiation codon and adjacent sequences, is inserted into the appropriate expression vector, no additional translational control signals may be needed. However, in cases where only a portion of the SHR coding sequence is inserted, exogenous translational control signals, including the ATG initiation codon, must be provided. Furthermore, the initiation codon must be in phase with the reading frame of the SHR coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the SHR protein may be engineered. Rather than using expression vectors which contain viral origins of replication, host cells can be transformed with the SHR coding sequence controlled by appropriate expression control elements (e.g., promoter and/or enhancer sequences, transcription terminators, polyadenylation sites, etc.), and a selectable marker. Following the introduction of foreign DNA, genetically engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the SHR protein. Such engineered cell lines are particularly useful in screening for molecules or drugs that affect SHR function.

A number of selection systems may be used, including but not limited to, the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻ or aprt⁻ cells, respectively. Also, antimetabolite resistance can be used as the basis of selection for dhfr, which confers resistance to methotrexate (Wigler, et al., 1980, Proc. Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G418 (Colberre-Garapin, et al., 1981, J. Mol. Biol.

150:1); and hygro, which confers resistance to hygromycin (Santerre, et al., 1984, Gene 30:147) genes. Additional selectable genes include trpB, which allows cells to utilize indole in place of tryptophan; hisD, which allows cells to utilize histinol in place of histidine (Hartman & Mulligan, 1988, Proc. Natl. Acad. Sci. USA 85:8047); ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.) and glutamine synthetase (Bebbington et al., 1992, Biotech 10: 169).

The expression characteristics of an endogenous SHR gene within a cell line, plant or microorganism may be modified by inserting a heterologous DNA regulatory element into the genome of a stable cell line, plant or cloned microorganism such that the inserted regulatory element is operatively linked with the endogenous SHR gene. For example, an endogenous SHR gene which is normally "transcriptionally silent", i.e., an SHR gene which is normally not expressed, or is expressed only at very low levels in a cell line, plant or microorganism, may be activated by inserting a regulatory element which is capable of promoting the expression of a normally expressed gene product in that cell line, plant or microorganism. Alternatively, a transcriptionally silent, endogenous SHR gene may be activated by insertion of a promiscuous regulatory element that works across cell types.

A heterologous regulatory element may be inserted into a stable cell line, plant or cloned microorganism, such that it is operatively linked with an endogenous SHR gene, using techniques which are well known to those of skill in the art, such as targeted homologous recombination (e.g., in Chappel, U.S. Pat. No. 5,272,071; PCT publication No. WO 91/06667, published May 16, 1991).

5.3.2. Protein Purification

Once a recombinant protein is expressed, it can be identified by assays based on the physical or functional properties of the product, including radioactive labeling of the product followed by analysis by gel electrophoresis, radioimmunoassay, ELISA, bioassays, etc.

Once the encoded protein is identified, it may be isolated and purified by standard methods including chromatography (e.g., high performance liquid chromatography, ion exchange, affinity, and sizing column chromatography), centrifugation, differential solubility, or by any other standard technique for the purification of proteins. The actual conditions used will depend, in part, on factors such as net charge, hydrophobicity, hydrophilicity, etc., and will be apparent to those having skill in the art. The functional properties may be evaluated using any suitable assay, e.g. an assay for the ability to alter root formation. For the practice of the present invention, it is preferred that the polypeptide is at least 80% purified from other proteins. It is more preferred that they are at least 90% purified. For in vivo administration, it is preferred that it is greater than 95% purified, and more preferably greater than 99%.

5.4. Identification of Cells That Express SHR

The host cells which contain the coding sequence and which express a SHR gene product, fragments thereof, or a SHR fusion protein may be identified by at least four general approaches; (a) DNA-DNA or DNA-RNA hybridization; (b) the presence or absence of "marker" gene functions; (c) assessing the level of transcription as measured by the expression of SHR mRNA transcripts in the host cell; and (d) detection of the gene product as measured by its biological activity or by use of analytical techniques such mass-spectroscopy, amino acid sequencing or immunodetection. Prior to the identification of gene expression, the host cells may be first mutagenized in an effort to increase the level of expression of SHR, especially in cell lines that produce low amounts of SHR.

In the first approach, the presence of the SHR coding sequence inserted in the expression vector can be detected by DNA-DNA or DNA-RNA hybridization using probes comprising nucleotide sequences that are homologous to the SHR coding sequence or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the SHR coding sequence is inserted within a marker gene sequence of the vector, recombinants containing the SHR coding sequence can be identified by the absence of the marker gene function. Alternatively, a marker gene can be placed in tandem with the SHR coding sequence under the control of the same or different promoter used to control the expression of the SHR coding sequence. Expression of the marker in response to induction or selection indicates expression of the SHR coding sequence.

In the third approach, transcriptional activity for the SHR coding region can be assessed by hybridization assays. For example, RNA can be isolated and analyzed by Northern blot using a probe homologous to the SHR coding sequence or particular portions thereof. Alternatively, total nucleic acids of the host cell may be extracted and assayed for hybridization to such probes. Additionally, RT-PCR may be used to detect low levels of gene expression.

In the fourth approach, the expression of the SHR protein product can be assessed immunologically, for example by Western blots, immunoassays such as radioimmunoprecipitation, enzyme-linked immunoassays and the like. This can be achieved by using an anti-SHR antibody. Expression of the SHR protein product can also be assessed using analytical techniques such as amino acid sequencing, which can be accomplished by means of, for example, Edman degradation or tandem mass spectroscopy, or by analysis of the masses of peptides generated by partial hydrolysis of the protein product using mass spectroscopy. In the identification of SHR protein by mass spectroscopy, it will often be desirable to separate the SHR protein from other protein constituents of the cell by means of two-dimensional gel electrophoresis, partially hydrolyze the isolated protein using an amino acid specific protease (e.g., Lys-C, trypsin), and then determine the mass of the resulting peptide fragments using mass spectroscopy. Determination of peptide mass can then be used to identify the protein as SHR, or a variant thereof, using a database of the predicted masses of protein proteolysis products and analysis software such as Protein Prospector, which is publicly available on the internet at http://prospector.ucsf.edu.

5.4.1. Antibodies to SHR Proteins and Polypeptides

Antibodies that specifically recognize one or more epitopes of SHR, or epitopes of conserved variants of SHR, or peptide fragments of the SHR are also encompassed by the invention. Such antibodies include, but are not limited to, polyclonal antibodies, monoclonal antibodies (mAbs), human, humanized or chimeric antibodies, single chain antibodies, Fab fragments, F(ab')$_2$ fragments, fragments produced by a Fab expression library, anti-idiotypic (anti-Id) antibodies and epitope-binding fragments of any of the above.

For the production of antibodies, various host animals may be immunized by injection with the SHR protein, a SHR peptide (e.g., one corresponding to a functional domain of the protein), a truncated SHR polypeptide (SHR in which one or more domains has been deleted), functional equivalents of the SHR protein or mutants of the SHR protein. Such SHR proteins, polypeptides, peptides or fusion proteins can be prepared and obtained as described, supra. Host animals may include, but are not limited to, rabbits, mice and rats, to name but a few. Various adjuvants may be used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies to SHR may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). Such antibodies may be of any immunoglobulin class including, but not limited to, IgG, IgM, IgE, IgA, IgD and any subclass thereof. The hybridoma producing the monoclonal antibodies of this invention may be cultivated in vitro or in vivo.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison (1985) *Science* 229:1202–1207; Oi et al. (1986) *Bio/Techniques* 4:214; U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, *Int. Rev. Immunol.* 13:65–93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Fremont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et at. (1994) *Bio/technology* 12:899–903).

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against SHR proteins or polypeptides. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a SHR protein and/or polypeptide can, in turn, be utilized to generate anti-idiotype antibodies that "mimic" SHR, using techniques well known to those skilled in the art. (See, e.g., Greenspan & Bona, 1993, FASEB J 7(5):437–444; and Nissinoff, 1991, J. Immunol. 147(8):2429–2438).

5.4.2. SHR Gene or Gene Products as Markers for Quantitative Trait Loci

Any of the nucleotide sequences and/or polypeptides described above, can be used as markers for quantitative trait loci in breeding programs for crop plants. To this end, the nucleic acid molecules, including, but not limited to, full length SHR coding sequences, and/or partial sequences, can be used in hybridization and/or DNA amplification assays to identify the endogenous SHR genes, shr mutant alleles and/or SHR expression products in cultivars as compared to wild-type plants. They can be used also as markers for linkage analysis of quantitative trait loci. It is possible also that the SHR gene may encode a product responsible for a qualitative trait that is desirable in a crop breeding program. Alternatively, the SHR protein, peptides and/or antibodies can be used as reagents in immunoassays to detect expression of the SHR gene in cultivars and wild-type plants.

5.4.3. SHR-Like Genes

Short-root-like (SHL) genes are genes which show a high degree of similarity to the SHR gene. Sequence analysis of SHL genes showed that a variable amino-terminal (N-terminal) and a highly conserved carboxyl-termini (C-termini) region exist throughout these putative gene products. The highly conserved region does not show significant similarity to members of any recognized gene family, indicating that these sequences likely define a novel gene family. Based on the high degree of similarity of the gene products to SHR, the genes corresponding to these sequences were designated SHORT-ROOT-LIKE (SHL). Recently, the importance of this gene family has been confirmed. Two components of the gibberellin signal transduction pathway, the gene products of the GIBBERELLIN-ACID INSENSITIVE (GAI) and the REPRESSOR OF GAI (RGA) loci, have been shown to be members of this family (Peng et al., 1997, Genes & Dev. 11, 3194–3205; Silverstone et al., 1998, Plant Cell 10, 155–169). Thus, this family of gene products has been designated as the GRAS gene family, an acronym based on the designations of the known genes: GAI, RGA, and SCR. An alignment of various GRAS gene products shows that the gene products have at least five recognizable motifs that are highly conserved: the VHIID and SAW motifs, the hydrophobic residues of the leucine heptads, the P-F-Y-R-E residues of the PFYRE motif, and the two short sequences that define the end of the VHIID motif and the beginning of the PFYRE motif. Intriguingly, the majority of the SHL genes are expressed predominantly in the root. In addition to root, many of the SHL genes are expressed in siliques and shoots.

The SHL genes and gene products may be isolated and expressed with methods similar to those discussed for SHR genes, supra. Furthermore, antibodies to SHL proteins and polypeptides may be produced as was discussed, supra. Finally, SHL genes and gene products may be used as markers for quantitative trait loci as was discussed, supra.

5.5. SHR Promoters

According to the present invention, SHR promoters and functional portions thereof described herein refer to regions of the SHR gene which are capable of promoting tissue-specific expression in embryos, roots and shoots of an operably linked coding sequence in plants. The SHR promoter described herein refers to the regulatory elements of SHR genes, i.e., regulatory regions of genes which are capable of selectively hybridizing to the nucleic acids described in Section 5.1, or regulatory sequences contained therein, or which are homologous by sequence analysis (containing a span of 10 or more nucleotides in which at least 50 percent of the nucleotides are identical to the sequences presented herein). Homologous nucleotide sequences refer to nucleotide sequences including, but not limited to, SHR promoters in diverse plant species (e.g., promoters of orthologs of *Arabidopsis* SHR) as well as genetically engineered derivatives of the promoters described herein.

Methods which could be used for the synthesis, isolation, molecular cloning, characterization and manipulation of SHR promoter sequences are well known to those skilled in the art. See, e.g., the techniques described in Sambrook et al., Molecular Cloning: A Laboratory Manual, 2nd. ed., Cold Spring Harbor Laboratory, Cold Spring Harbor, N.Y. (1989).

According to the present invention, SHR promoter sequences or portions thereof described herein may be obtained from appropriate plant or mammalian sources from cell lines or recombinant DNA constructs containing SHR promoter sequences, and/or by chemical synthetic methods. SHR promoter sequences can be obtained from genomic clones containing sequences 5' upstream of SHR coding sequences. Such 5' upstream clones may be obtained by screening genomic libraries using SHR protein coding sequences, particularly those encoding SHR N-terminal sequences, from SHR gene clones obtained as described above. Standard methods that may used in such screening include, for example, the method set forth in Benton & Davis, 1977, Science 196:180 for bacteriophage libraries; and Grunstein & Hogness, 1975, Proc. Nat. Acad. Sci. U.S.A. 72:3961–3965 for plasmid libraries.

The full extent and location of SHR promoters within such 5' upstream clones may be determined by the functional assay described below. In the event a 5' upstream clone does not contain the entire SHR promoter as determined by the functional assay, the insert DNA of the clone may be used to isolate genomic clones containing sequences further 5' upstream of the SHR coding sequences. Such further upstream sequences can be spliced on to existing 5' upstream sequences and the reconstructed 5' upstream region tested for functionality as a SHR promoter (i.e., promoting tissue-specific expression in embryos and/or roots of an operably linked gene in plants). This process may be repeated until the complete SHR promoter is obtained.

The location of the SHR promoter within genomic sequences 5' upstream of the SHR gene isolated as described above may be determined using any method known in the art. For example, the 3' end of the promoter may be identified by locating the transcription initiation site, which may be determined by methods such as RNase protection (e.g., Liang et al., 1989, J. Biol. Chem. 264:14486–14498), primer extension (e.g., Weissenborn & Larson, 1992, J. Biol. Chem. 267:6122–6131) and/or reverse transcriptase/PCR. The location of the 3' end of the promoter may be confirmed by sequencing and computer analysis, examining for the canonical AGGA or TATA boxes of promoters that are typically 50–60 base pairs (bp) and 25–35 bp, respectively, 5' upstream of the transcription initiation site. The 5' end promoter may be defined by deleting sequences from the 5' end of the promoter containing fragment, constructing a transcriptional or translational fusion of the resected fragment and a reporter gene and examining the expression characteristics of the chimeric gene in transgenic plants. Reporter genes that may be used to such ends include, but are not limited to, GUS, CAT, luciferase, β-galactosidase and C1 and R gene controlling anthocyanin production.

According to the present invention, a SHR promoter is one that confers to an operably linked gene in a transgenic plant tissue-specific expression in roots, root nodules, stems and/or embryos. A SHR promoter comprises the region between about −5,000 bp and +1 bp upstream of the transcription initiation site of a SHR gene. In a particular embodiment, the *Arabidopsis* SHR promoter comprises the region between positions about −2.5 kb and +1 in the 5' upstream region of the *Arabidopsis* SHR gene.

5.5.1. Cis-regulatory Elements of SHR Promoters

According to the present invention, the cis-regulatory elements within a SHR promoter may be identified using any method known in the art. For example, the location of cis-regulatory elements within an inducible promoter may be identified using methods such as DNase or chemical footprinting (e.g., Meier et al., 1991, Plant Cell 3:309–315) or gel retardation (e.g., Weissenborn & Larson, 1992, J. Biol. Chem. 267-6122–6131; Beato, 1989, Cell 56:335–344; Johnson et al., 1989, Ann. Rev. Biochem. 58:799–839). Additionally, resectioning experiments also may be employed to define the location of the cis-regulatory elements. For example, an inducible promoter-containing fragment may be resected from either the 5' or 3' end using restriction enzyme or exonuclease digests.

To determine the location of cis-regulatory elements within the sequence containing the inducible promoter, the 5' or 3' resected fragments, internal fragments to the inducible promoter containing sequence or inducible promoter fragments containing sequences identified by footprinting or gel retardation experiments may be fused to the 5' end of a truncated plant promoter, and the activity of the chimeric promoter in transgenic plant examined. Useful truncated promoters to these ends comprise sequences starting at or about the transcription initiation site and extending to no more than 150 bp 5' upstream. These truncated promoters generally are inactive or are only minimally active. Examples of such truncated plant promoters may include, among others, a "minimal" CaMV 35S promoter whose 5' end terminates at position −46 bp with respect to the transcription initiation site (Skriver et al., Proc. Natl. Acad. Sci. USA 88:7266–7270); the truncated "−90 35S" promoter in the X-GUS-90 vector (Benfey & Chua, 1989, Science 244:174–181); a truncated "−101 nos" promoter derived from the nopaline synthase promoter (Aryan et al., 1991, Mol. Gen. Genet. 225:65–71); and the truncated maize Adh-1 promoter in pADcat 2 (Ellis et al., 1987, EMBO J. 6:11–16).

According to the present invention, a cis-regulatory element of a SHR promoter is a sequence that confers to a truncated promoter tissue-specific expression in embryos, stems, root nodules and/or roots.

5.5.2. SHR Promoter-Driven Expression Vectors

The properties of the nucleic acid sequences are varied as are the genetic structures of various potential host plant cells. In the preferred embodiments of the present invention, described herein, a number of features which an artisan may recognize as not being absolutely essential, but clearly advantageous are used. These include methods of isolation, synthesis or construction of gene constructs, the manipulation of the gene constructs to be introduced into plant cells, certain features of the gene constructs, and certain features of the vectors associated with the gene constructs.

Further, the gene constructs of the present invention may be encoded on DNA or RNA molecules. According to the present invention, it is preferred that the desired, stable genotypic change of the target plant be effected through genomic integration of exogenously introduced nucleic acid construct(s), particularly recombinant DNA constructs. Nonetheless, according to the present invention, such genotypic changes also can be effected by the introduction of episomes (DNA or RNA) that can replicate autonomously and that are somatically and germinally stable. Where the introduced nucleic acid constructs comprise RNA, plant transformation or gene expression from such constructs may proceed through a DNA intermediate produced by reverse transcription.

The present invention provides for use of recombinant DNA constructs which contain tissue-specific and developmental-specific promoter fragments and functional portions thereof. As used herein, a functional portion of a SHR promoter is capable of functioning as a tissue-specific promoter in the embryo, stem, root nodule and/or root of a plant. The functionality of such sequences can be readily established by any method known in the art. Such methods include, for example, constructing expression vectors with such sequences and determining whether they confer tissue-specific expression in the embryo, stem, root nodule and/or root to an operably linked gene.

The SHR promoters of the invention may be used to direct the expression of any desired protein, or to direct the expression of a RNA product, including, but not limited to, an "antisense" RNA or ribozyme. Such recombinant constructs generally comprise a native SHR promoter or a recombinant SHR promoter derived therefrom, ligated to the nucleic acid sequence encoding a desired heterologous gene product.

A recombinant SHR promoter is used herein to refer to a promoter that comprises a functional portion of a native SHR promoter or a promoter that contains native promoter sequences that is modified by a regulatory element from a SHR promoter. Alternatively, a recombinant inducible promoter derived from the SHR promoter may be a chimeric promoter, comprising a full-length or truncated plant promoter modified by the attachment of one or more SHR cis-regulatory elements.

The manner of chimeric promoter constructions may be any well known in the art. For examples of approaches that can be used in such constructions, see Section 5.1.2., above and Fluhr et al., 1986, Science 232:1106–1112; Ellis et al., 1987, EMBO J. 6:11–16; Strittmatter & Chua, 1987, Proc. Natl. Acad. Sci. USA 84:8986–8990; Poulsen & Chua, 1988, Mol. Gen. Genet. 214:16–23; Comai et al., 1991, Plant Mol. Biol. 15:373–381; Aryan et al., 1991, Mol. Gen. Genet. 225:65–71.

According to the present invention, where a SHR promoter or a recombinant SHR promoter is used to express a desired protein, the DNA construct is designed so that the protein coding sequence is ligated in phase with the translational initiation codon downstream of the promoter. Where the promoter fragment is missing 5' leader sequences, a DNA fragment encoding both the protein and its 5' RNA leader sequence is ligated immediately downstream of the transcription initiation site. Alternatively, an unrelated 5' RNA leader sequence may be used to bridge the promoter and the protein coding sequence. In such instances, the design should be such that the protein coding sequence is ligated in phase with the initiation codon present in the leader sequence, or ligated such that no initiation codon is interposed between the transcription initiation site and the first methionine codon of the protein.

Further, it may be desirable to include additional DNA sequences in the protein expression constructs. Examples of additional DNA sequences include, but are not limited to, those encoding: a 3' untranslated region; a transcription termination and polyadenylation signal; an intron; a signal peptide (which facilitates the secretion of the protein); or a transit peptide (which targets the protein to a particular cellular compartment such as the nucleus, chloroplast, mitochondria or vacuole).

5.6. Production of Transgenic Plants And Plant Cells

According to the present invention, a desirable plant or plant cell may be obtained by transforming a plant cell with the nucleic acid constructs described herein. In some instances, it may be desirable to engineer a plant or plant cell with several different gene constructs. Such engineering may be accomplished by transforming a plant or plant cell with all of the desired gene constructs simultaneously. Alternatively, the engineering may be carried out sequentially. That is, transforming with one gene construct, obtaining the desired transformant after selection and screening, transforming the transformant with a second gene construct, and so on.

In an embodiment of the present invention, *Agrobacterium* is employed to introduce the gene constructs into plants. Such transformations preferably use binary *Agrobacterium* T-DNA vectors (Bevan, 1984, Nuc. Acid Res. 12:8711–8721) and the co-cultivation procedure (Horsch et al., 1985, Science 227:1229–1231). Generally, the *Agrobacterium* transformation system is used to engineer dicotyledonous plants (Bevan et al., 1982, Ann. Rev. Genet. 16:357–384; Rogers et al., 1986, Methods Enzymol. 118:627–641). The *Agrobacterium* transformation system also may be used to transform, as well as transfer, DNA to monocotyledonous plants and plant cells (see Hernalsteen et al., 1984, EMBO J. 3:3039–3041; Hooykass-Van Slogteren et al., 1984, Nature 311:763–764; Grimsley et al., 1987, Nature 325:1677–179; Boulton et al., 1989, Plant Mol. Biol. 12:3140.; Gould et al., 1991, Plant Physiol. 95:426–434).

In other embodiments, various alternative methods for introducing recombinant nucleic acid constructs into plants and plant cells also may be utilized. These other methods are particularly useful where the target is a monocotyledonous plant or plant cell. Alternative gene transfer and transformation methods include, but are not limited to, protoplast transformation through calcium-, polyethylene glycol (PEG), electroporation-mediated uptake of naked DNA (see Paszkowski et al., 1984, EMBO J. 3:2717–2722, Potrykus et al., 1985, Mol. Gen. Genet. 199:169–177; Fromm et al., 1985, Proc. Natl. Acad. Sci. USA 82:5824–5828; Shimamoto, 1989, Nature 338:274–276) and electroporation of plant tissues (D'Halluin et al., 1992, Plant Cell 4:1495–1505). Additional methods for plant cell transformation include microinjection, silicon carbide mediated DNA uptake (Kaeppler et al., 1990, Plant Cell Reporter 9:415418) and microprojectile bombardment (see Klein et al., 1988, Proc. Natl. Acad. Sci. USA 85:4305–4309; Gordon-Kamm et al., 1990, Plant Cell 2:603–618).

According to the present invention, a wide variety of plants may be engineered for the desired physiological and agronomic characteristics described herein using the nucleic acid constructs of the instant invention and the various transformation methods mentioned above. In preferred embodiments, target plants for engineering include, but are not limited to, crop plants such as maize, wheat, rice, soybean, tomato, tobacco, carrots, peanut, potato, sugar beets, sunflower, yam, *Arabidopsis*, rape seed and petunia; and trees such as spruce.

According to the present invention, desired plants and plant cells may be obtained by engineering the gene constructs described herein into a variety of plant cell types, including, but not limited to, protoplasts, tissue culture cells, tissue and organ explants, pollen, embryos as well as whole plants. In an embodiment of the present invention, the engineered plant material is selected or screened for transformants (i.e., those that have incorporated or integrated the introduced gene construct(s)) following the approaches and methods described below. An isolated transformant may then be regenerated into a plant. Alternatively, the engineered plant material may be regenerated into a plant, or plantlet, before subjecting the derived plant, or plantlet, to selection or screening for the marker gene traits. Procedures for regenerating plants from plant cells, tissues or organs, either before or after selecting or screening for marker gene(s), are well known to those skilled in the art.

A transformed plant cell, callus, tissue or plant may be identified and isolated by selecting or screening the engineered plant material for traits encoded by the marker genes present on the transforming DNA. For instance, selection may be performed by growing the engineered plant material on media containing inhibitory amounts of the antibiotic or herbicide to which the transforming marker gene construct confers resistance. Further, transformed plants and plant cells also may be identified by screening for the activities of any visible marker genes (e.g., the β-glucuronidase, luciferase, B or C1 genes) that may be present on the recombinant nucleic acid constructs of the present invention. Such selection and screening methodologies are well known to those skilled in the art.

Physical and biochemical methods also may be used to identify a plant or plant cell transformant containing the gene constructs of the present invention. These methods include, but are not limited to: 1) Southern analysis or PCR amplification for detecting and determining the structure of the recombinant DNA insert; 2) Northern blot, S-1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, western blot techniques, immunoprecipitation, or enzyme-linked immunoassays, where the gene construct products are proteins; 5) biochemical measurements of compounds produced as a consequence of the expression of the introduced gene constructs. Additional techniques, such as in situ hybridization, enzyme staining, and immunostaining also may be used to detect the presence or expression of the recombinant construct in specific plant organs and tissues. The methods for doing all of these assays are well known to those skilled in the art.

5.6.1. Transgenic Plants That Ectopically Express SHR

In accordance with the present invention, a plant that expresses a recombinant SHR gene may be engineered by transforming a plant cell with a gene construct comprising a plant promoter operably associated with a sequence encoding a SHR protein or a fragment thereof. (Operably associated is used herein to mean that transcription controlled by the "associated" promoter would produce a functional messenger RNA, whose translation would produce the enzyme.) The plant promoter may be constitutive or inducible. Useful constitutive promoters include, but are not limited to, the CaMV 35S promoter, the T-DNA mannopine synthetase promoter and their various derivatives. Useful inducible promoters include, but are not limited to, the promoters of ribulose bisphosphate carboxylase (RUBISCO) genes, chlorophyll a/b binding protein (CAB) genes, heat shock genes, the defense responsive gene (e.g., phenylalanine ammonia lyase genes), wound induced genes (e.g., hydroxyproline rich cell wall protein genes), chemically-inducible genes (e.g., nitrate reductase genes, gluconase genes, chitinase genes, PR-1 genes etc.), dark-inducible genes (e.g., asparagine synthetase gene (Coruzzi and Tsai, U.S. Pat. No. 5,256,558, Oct. 26, 1993, Gene Encoding Plant Asparagine Synthetase)) and developmentally regulated genes (e.g., Shoot Meristemless gene), to name just a few.

In yet another embodiment of the present invention, it may be advantageous to transform a plant with a gene construct operably linking a modified or artificial promoter to a sequence encoding a SHR protein or a fragment thereof. Typically, such promoters, constructed by recombining structural elements of different promoters, have unique expression patterns and/or levels not found in natural promoters. See, e.g., Salina et al., 1992, Plant Cell 4:1485–1493, for examples of artificial promoters constructed from combining cis-regulatory elements with a promoter core.

In a preferred embodiment of the present invention, the associated promoter is a strong and root, root nodule, stem and/or embryo-specific plant promoter such that the SHR protein is overexpressed in the transgenic plant. Examples of root- and root nodules-specific promoters include, but are not limited to, the promoters of SCR genes, SHR genes, legehemoglobin genes, nodulin genes and root-specific glutamine synthetase genes (See e.g., Tingey et al., 1987, EMBO J. 6:1–9; Edwards et al., 1990, Proc. Nat. Acad. Sci. USA 87:3459–3463).

In yet another preferred embodiment of the present invention, the overexpression of SHR protein in roots may be engineered by increasing the copy number of the SHR gene. One approach to producing such transgenic plants is to transform with nucleic acid constructs that contain multiple copies of the complete SHR gene (i.e., with its own native SHR promoter). Another approach is to repeatedly transform successive generations of a plant line with one or more copies of the complete SHR gene. Yet another approach is to place a complete SHR gene in a nucleic acid construct containing an amplification-selectable marker (ASM) gene such as the glutamine synthetase or dihydrofolate reductase gene. Cells transformed with such constructs are subjected to culturing regimes that select cell lines with increased copies of complete SHR genes. See, e.g., Donn et al., 1984, J. Mol. Appl. Genet. 2:549–562, for a selection protocol used to isolate a plant cell line containing amplified copies of the GS gene. Because the desired gene is closely linked to the ASM, cell lines that amplify the ASM gene are likely also to have amplified the SHR gene. Cell lines with amplified copies of the SHR gene can then be regenerated into transgenic plants.

5.6.2. Transgenic Plants That Suppress Endogenous SHR Expression

In accordance with the present invention, a desired plant may be engineered by suppressing SHR activity. In one embodiment, the suppression may be engineered by transforming a plant with a gene construct encoding an antisense RNA or ribozyme complementary to a segment, or the whole, of the SHR RNA transcript, including the mature target mRNA. In another embodiment, SHR gene suppression may be engineered by transforming a plant cell with a gene construct encoding a ribozyme that cleaves the SHR mRNA transcript. Alternatively, the plant can be engineered, e.g., via targeted homologous recombination, to inactive or "knock-out" expression of the plant's endogenous SHR.

For all of the aforementioned suppression constructs, it is preferred that such gene constructs express specifically in the root, root nodule, stem and/or embryo tissues. Alternatively, it may be preferred to have the suppression constructs expressed constitutively. Thus, constitutive promoters, such as the nopaline and the CAMV 35S promoter, also may be used to express the suppression constructs. A most preferred promoter for these suppression constructs is a SCR or SHR promoter.

In accordance with the present invention, desired plants with suppressed target gene expression may be engineered also by transforming a plant cell with a co-suppression construct. A co-suppression construct comprises a functional promoter operatively associated with a complete or partial SHR gene sequence. It is preferred that the operatively associated promoter be a strong, constitutive promoter, such as the CaMV 35S promoter. Alternatively, the co-suppression construct promoter can be one that expresses with the same tissue and developmental specificity as the SHR gene.

According to the present invention, it is preferred that the co-suppression construct encodes an incomplete SHR mRNA, although a construct encoding a fully functional SHR mRNA or enzyme also may be useful in effecting co-suppression.

In accordance with the present invention, desired plants with suppressed target gene expression also may be engineered by transforming a plant cell with a construct that can effect site-directed mutagenesis of the SHR gene. (See, e.g., Offringa et al., 1990, EMBO J. 9:3077–84; and Kanevskii et al., 1990, Dokl. Akad. Nauk. SSSR 312:1505–1507 for discussions of nucleic constructs for effecting site-directed mutagenesis of target genes in plants.) It is preferred that such constructs effect suppression of the SHR gene by replacing the endogenous SHR gene sequence through homologous recombination with either none, or inactive SHR protein coding sequences. In other embodiments, antisense, gene "knock-out," ribozyme, RNA interference (RNA-i) and/or triple helix methods can be used to affect SHR expression.

Antisense RNA and DNA molecules act to directly block the translation of mRNA by hybridizing to targeted mRNA and preventing protein translation. Antisense approaches involve the design of oligonucleotides which are complementary to an mRNA sequence. The antisense oligonucleotides will bind to the complementary mRNA sequence transcripts and prevent translation. Absolute complementarity, although preferred, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the sequence of interest could be used in an antisense approach to inhibit translation of endogenous mRNA. Antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit sequence expression. It is preferred that these studies utilize controls that distinguish between antisense gene inhibition and non-specific biological effects of oligonucleotides. Additionally, it is envisioned that results obtained using the antisense oligonucleotide are compared with those obtained using a control oligonucleotide. It is preferred that the control oligonucleotide is of approximately the same length as the test oligonucleotide and that the nucleic acid of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, Proc. Natl. Acad. Sci. U.S. 86:6553–6556; Lemaitre, et al., 1987, Proc. Natl. Acad. Sci. U.S.A. 84:648–652; PCT Publication No. WO88/09810, published Dec. 15, 1988) or hybridization-triggered cleavage agents (see, e.g., Krol et al., 1988, BioTechniques 6:958–976) or intercalating agents (see, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier, et al., 1987, Nucl. Acids Res. 15:6625–6641). The oligonucleotide is a 2'-0-methylribonucleotide (Inoue, et al., 1987, Nucl. Acids Res. 15:6131–6148), or a chimeric RNA-DNA analogue (Inoue, et al., 1987, FEBS Lett. 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (1988, Nucl. Acids Res. 16:3209), methylphosphonate oligonucleotides can be prepared by use of controlled pore glass polymer supports (Sarin, et al., 1988, Proc. Natl. Acad. Sci. U.S.A. 85:7448–7451), etc.

While antisense nucleotides complementary to the coding region sequence could be used, those complementary to the transcribed, untranslated region are most preferred.

Antisense molecules should be delivered to cells that express the SHR sequence in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies which specifically bind receptors or antigens expressed on the target cell surface) can be administered systemically.

A preferred approach to achieve intracellular concentrations of the antisense sufficient to suppress translation of endogenous mRNAs utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs which will form complementary base pairs with the endogenous sequence transcripts and thereby prevent translation of the mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3'-long terminal repeat of Rous sarcoma virus (Yamamoto, et al., 1980, Cell 22:787–797), the herpes thymidine kinase promoter (Wagner, et al., 1981, Proc. Natl. Acad. Sci. U.S.A. 78:1441–1445), the regulatory sequences of the metallothionein gene (Brinster, et al., 1982, Nature 296:39–42), etc. Any type of plasmid, cosmid, YAC or viral vector can be used to prepare the recombinant DNA construct that can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO90/11364, published Oct. 4, 1990; Sarver, et al., 1990, Science 247, 1222–1225).

Ribozymes are enzymatic RNA molecules capable of catalyzing the specific cleavage of RNA. (For a review, see Rossi, 1994, Current Biology 4:469471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions which form complementary base pairs with the target mRNA. The sole requirement is that the target mRNA have the following sequence of two bases: 5'-UG-3'. The construction and production of hammerhead ribozymes is well known in the art and is described more fully in Myers, 1995, *Molecular Biology and Biotechnology: A Comprehensive Desk Reference*, VCH Publishers, New York, (see especially FIG. 4, page 833) and in Haseloff and Gerlach, 1988, *Nature*, 334:585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, *Science,* 224:574–578; Zaug and Cech, 1986, *Science,* 231:470–475; Zaug, et al., 1986, *Nature,* 324:429–433; published International patent application No. WO 88/04300 by University Patents Inc.; Been and Cech, 1986, *Cell,* 47:207–216). The Cech-type ribozymes have an eight base pair active site that hybridizes to a target RNA sequence whereafter cleavage of the target RNA takes place. The invention encompasses those Cech-type ribozymes that target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes, unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, *Nature* 317:230–234; Thomas and Capecchi, 1987, *Cell* 51:503–512; Thompson, et al., 1989, *Cell* 5:313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells which express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra). However this approach can be adapted for use in plants provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures which prevent transcription of the target gene in target cells in the plant. (See generally, Helene, 1991, *Anticancer Drug Des.,* 6(6):569–584; Helene, et al., 1992, *Ann. N.Y. Acad. Sci.,* 660:27–36; and Maher, 1992, *Bioassays* 14(12):807–815).

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizable stretches of either purines or pyrimidines to be present on one strand of a duplex. Nucleic acids may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen which are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so-called "switchback" nucleic acid molecule. Switchback molecules are synthesized in an alternating 5'-3',3'-5' manner, such that they base pair with first one strand of a duplex and then the other, eliminating the necessity for a sizable stretch of either purines or pyrimidines to be present on one strand of a duplex.

In an alternate embodiment, double stranded RNA interference (RNA-i) can be used to specifically disrupt gene expression. More specifically, RNA-i can be used for the targeted disruption of given genetic functions in *Drosophila* (Misquitta, L., et al., 1999, PNAS 96:1451–1456), in plants such as *Arabidopsis thaliana* (Chuang, C. F., et al., 2000, PNAS 97:4985–4990), etc.

Anti-sense RNA and DNA, ribozyme, RNA-i and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid-phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.6.3. Transgenic Plants That Express a Transgene Controlled by the SHR Promoter In accordance with the present invention, a desired plant may be engineered to express a gene of interest under the control of the SHR promoter. SHR promoters and functional portions thereof refer to regions of the nucleic acid sequence which are capable of promoting tissue-specific transcription of an operably linked gene of interest in the embryo, stem, root nodule and/or root of a plant. The SHR promoter described herein refers to the regulatory elements of SHR genes as described above.

Genes that may be beneficially expressed in the roots and/or root nodules of plants include genes involved in nitrogen fixation or cytokines or auxins, or genes which regulate growth, or growth of roots. In addition, genes encoding proteins that confer on plants herbicide, salt or pest resistance may be engineered for root specific expression. The nutritional value of root crops may be enhanced also through SHR promoter driven expression of nutritional proteins. Alternatively, therapeutically useful proteins may be expressed specifically in root crops.

Genes that may be beneficially expressed in the stems of plants include those involved in starch lignin or cellulose biosynthesis.

In accordance with the present invention, desired plants which express a heterologous gene of interest under the control of the SHR promoter may be engineered by transforming a plant cell with SHR promoter driven constructs using those techniques described, supra.

5.6.4. Screening of Transformed Plants For Those Having Desired Altered Traits

It will be recognized by those skilled in the art that in order to obtain transgenic plants having the desired engineered traits, screening of transformed plants (i.e., those having an gene construct of the invention) having those traits may be required. For example, where the plants have been engineered for ectopic overexpression of a SHR gene, transformed plants are examined for those expressing the SHR gene at the desired level and in the desired tissues and developmental stages. Where the plants have been engineered for suppression of the SHR gene product, transformed plants are examined for those expressing the SHR gene product (e.g., RNA or protein) at reduced levels in various tissues. The plants exhibiting the desired physiological changes, e.g., ectopic SHR overexpression or SHR suppression, may then be subsequently screened for those plants that have the desired structural changes at the plant level (e.g., transgenic plants with overexpression or suppression of SHR gene having the desired altered root structure). The same principle applies to obtaining transgenic plants having tissue-specific expression of a heterologous gene in embryos and/or roots by the use of a SHR promoter driven expression construct.

Alternatively, the transformed plants may be directly screened for those exhibiting the desired structural and functional changes. In one embodiment, such screening may be for the size, length or pattern of the root of the transformed plants. In another embodiment, the screening of the transformed plants may be for altered gravitropism or decreased susceptibility to lodging. In other embodiments, the screening of the transformed plants may be for improved agronomic characteristics (e.g., faster growth, greater vegetative or reproductive yields or improved protein contents, etc.), as compared to unengineered progenitor plants, when cultivated under various growth conditions (e.g., soils or media containing different amounts of nutrients and water content).

According to the present invention, plants engineered with SHR overexpression may exhibit improved vigorous growth characteristics when cultivated under conditions where large and thicker roots are advantageous. Plants engineered for SHR suppression may exhibit improved vigorous growth characteristics when cultivated under conditions where thinner roots are advantageous.

Engineered plants and plant lines possessing such improved agronomic characteristics may be identified by examining any of following parameters: 1) the rate of growth, measured in terms of rate of increase in fresh or dry weight; 2) vegetative yield of the mature plant, in terms of fresh or dry weight; 3) the seed or fruit yield; 4) the seed or fruit weight; 5) the total nitrogen content of the plant; 6) the total nitrogen content of the fruit or seed; 7) the free amino acid content of the plant; 8) the free amino acid content of the fruit or seed; 9) the total protein content of the plant; and 10) the total protein content of the fruit or seed. The procedures and methods for examining these parameters are well known to those skilled in the art.

According to the present invention, a desired plant is one that exhibits improvement over the control plant (i.e., progenitor plant) in one or more of the aforementioned parameters. In an embodiment, a desired plant is one that shows at least 5% increase over the control plant in at least one parameter. In a preferred embodiment, a desired plant is one that shows at least 20% increase over the control plant in at least one parameter. Most preferred is a plant that shows at least 50% increase in at least one parameter.

5.7. Screening Assays

Genetically engineered cells, cell lines and/or transgenic plants containing a SHR promoter, or fragment thereof, operably linked to a reporter gene, can be used as systems for the screening of agents that modulate SHR promoter activity. Such transgenic plants provide an experimental model in vivo (or can be used as a source of primary cells or cell lines for use in vitro) which can be used to develop new methods of treating root and/or shoot-related disorders.

The present invention encompasses screening assays designed to identify compounds that modulate activity of the SHR promoter. The present invention encompasses in vitro and cell-based assays, as well as in vivo assays in transgenic plants. As described hereinbelow, compounds to be tested may include, but are not limited to, oligonucleotides, peptides, proteins, small organic or inorganic compounds, antibodies, etc.

Examples of compounds may include, but are not limited to, peptides, such as, for example, soluble peptides, including, but not limited to, Ig-tailed fusion peptides, and 4 members of random peptide libraries; (see, e.g., Lam, et al., 1991, Nature 354:82–84; Houghten, et al., 1991, Nature 354:84–86), and combinatorial chemistry-derived molecular library made of D- and/or L-configuration amino acids, phosphopeptides (including, but not limited to members of random or partially degenerate, directed phosphopeptide libraries; see, e.g., Songyang, et al., 1993, Cell 72:767–778), antibodies (including, but not limited to, polyclonal, monoclonal, human, humanized, anti-idiotypic, chimeric or single chain antibodies, and FAb, F(ab')$_2$ and FAb expression library fragments, and epitope-binding fragments thereof), and small organic or inorganic molecules.

In one preferred embodiment, genetically engineered cells, cell lines or primary cultures of germ and/or somatic cells containing a plant SHR promoter operatively linked to a heterologous gene are used to develop assay systems to screen for compounds which can inhibit sequence-specific DNA-protein interactions. Such methods comprise contacting a compound to a cell that expresses a gene under the control of a SHR promoter, or a transcriptionally active fragment thereof, measuring the level of the gene expression or gene product activity and comparing this level to the level of gene expression or gene product activity produced by the cell in the absence of the compound, such that if the level obtained in the presence of the compound differs from that obtained in its absence, a compound capable of modulating the expression of the plant SHR promoter has been identified. Alterations in gene expression levels may be by any number of methods known to those of skill in the art e.g., by assaying for reporter gene activity, assaying cell lysates for mRNA transcripts, e.g. by Northern analysis or using other methods known in the art for assaying for gene products expressed by the cell.

In another embodiment, microdissection and transillumination can be used. In this embodiment, a test agent is delivered to the transgenic plant by any of a variety of methods. The effect of such test compounds on the root and/or shoot cells can be analyzed by the microdissection and transillumination of the cells. If the level of reporter gene expression observed or measured in the presence of the compound differs from that obtained in its absence, a compound capable of modulating the expression of the plant SHR promoter has been identified.

In various embodiments of the invention, compounds that may be used in screens for modulators include peptides, small molecules, both naturally occurring and/or synthetic (e.g., libraries of small molecules or peptides), cell-bound or soluble molecules, organic, non-protein molecules and recombinant molecules that may have SHR promoter binding capacity and, therefore, may be candidates for pharmaceutical agents.

Alternatively, the proteins and compounds include endogenous cellular components which interact with SHR promoter sequences in vivo. Cell lysates or tissue homogenates may be screened for proteins or other compounds which bind to the SHR promoter, or fragment thereof. Such endogenous components may provide new targets for pharmaceutical and therapeutic interventions.

In one embodiment, libraries can be screened. Many libraries are known in the art that can be used, e.g., peptide libraries, chemically synthesized libraries, recombinant (e.g., phage display libraries), and in vitro translation-based libraries. In one embodiment of the present invention, peptide libraries may be used to screen for agonists or antagonists of SHR promoter-linked reporter expression. Diversity libraries, such as random or combinatorial peptide or non-peptide libraries can be screened for molecules that specifically modulate SHR promoter activity. Random peptide libraries consisting of all possible combinations of amino acids attached to a solid phase support may be used to identify peptides that are able to activate or inhibit SHR promoter activities (Lam, K. S. et al., 1991, Nature 354: 82–84). The screening of peptide libraries may have therapeutic value in the discovery of pharmaceutical agents that stimulate or inhibit the expression of SHR promoter regions.

Examples of chemically synthesized libraries are described in Fodor et al., 1991, Science 251:767–773; Houghten et al., 1991, Nature 354:84–86; Lam et al., 1991, Nature 354:82–84; Medynski, 1994, BioTechnology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott and Smith, 1990, Science 249:386–390; Devlin et al., 1990, Science, 249:404–406; Christian, et al., 1992, J. Mol. Biol. 227:711–718; Lenstra, 1992, J. Immunol. Meth. 152:149–157; Kay et al., 1993, Gene 128:59–65; and PCT Publication No. WO 94/18318 dated Aug. 18, 1994.

By way of example of non-peptide libraries, a benzodiazepine library (see e.g., Bunin et al., 1994, Proc. Natl. Acad. Sci. USA 91:4708–4712) can be adapted for use. Peptoid libraries (Simon et al., 1992, Proc. Natl. Acad. Sci. USA 89:9367–9371) also can be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

The assays of the present invention may be first optimized on a small scale (i.e., in test tubes), and then scaled up for high-throughput assays. The screening assays of the present invention may be performed in vitro, i.e., in test tubes, using purified components or cell lysates. The screening assays of the present invention may also be carried out in intact cells in culture and in plant models. In accordance with the present invention, test compounds which are shown to modulate the activity of the SHR promoter in vitro, as described herein, will further be assayed in vivo in cultured cells and plant models to determine if the test compound has the similar effects in vivo.

6. Example

Short-Root Expression, Cloning and Characterization 6.1. Materials and Methods 6.1.1. *Arabidopsis* Strains and Growth Condition shr-1 (in WS ecotype), shr-2 (Col), and scr-1 (WS) have been previously described (Benfey et al., 1993, Development 119, 57–70; Scheres et al., 1995, Development 121, 53–62; Fukaki et al., 1998, Plant J. 14, 425–430; Di Laurenzio et al., 1996, Cell 86, 423–433). Unstable shr-3 and shr-4 alleles (Col) were identified in lines containing the autonomous maize transposon, En (Wisman et al., 1998, Plant Mol. Biol. 37, 989–999). The SCR::GFP line has been described previously (Sabatini et al., 1999, Cell 99, 463–472; Wysocka-Diller et al., 2000, Development 127, 593–603). The growth condition of seedlings and plants has been described previously (Benfey et al., 1993, Development 119, 57–70).

6.1.2. Genetic Crosses

To determine allelism, a heterozygote carrying the shr-2 allele was pollinated by shr-3. In the resulting progeny (n=30) 34% showed the mutant phenotype indicating that the two mutations are allelic. The cross was confirmed by amplifying En specific sequences from the mutant plants (Wisman et al., 1998, Plant Mol. Biol. 37, 989–999). A line homozygous for shr-2 and gl1 was pollinated by shr-4. In the resulting F1 progeny (n=15) 100% showed the mutant phenotype indicating that the two mutations are allelic. The cross was confirmed by the presence of normal trichomes on the mutant.

To construct the shr-1, shr-2, and shr-3 lines containing SCR::GFP, each shr allele was pollinated by a plant homozygous for the SCR::GFP fusion, and the resulting F1 and F2 plants were self-pollinated to generate F3 plants homozygous for both the fusion and the shr mutation. To construct the shr-1 and scr-3 lines containing SHR::GFP, each mutant line was pollinated by a plant heterozygous for a SHR::GFP fusion, and the resulting kanamycin-resistant F1 plants were self-pollinated to generate F2 plants which segregated lines homozygous for each mutation and containing the transgene.

6.1.3. Mapping

The following mapping crosses were performed: shr-1/Ws×Col, shr-2/Col×Ler and shr-2/Col×ap2-10/C24. In each case homozygous wild-type or ap2-10 plants were pollinated with shr pollen (with the exception of shr-2/Col×Ler in which Ler pollen was used to pollinate shr-2), and the resulting F1 plants were self-pollinated to generate F2 plants segregating the shr mutation. The rough map position of shr-1 was obtained using SSLP (Bell and Ecker, 1994, Genomics 18, 137–144) and CAPS (Konieczny and Ausubel, 1993, Plant J. 4, 403–410) markers by analyzing DNAs from 30 to 40 F2 shr-1 mutant plants resulting from the mapping cross. For fine mapping, DNAs isolated from 74 and 56 F2 shr mutants resulting from crosses of shr-1 and shr-2 with wild type, respectively, were analyzed for linkage to the marker ngal 107 (Li and Chory, 1997, Cell 90, 929–38). For the cross between shr-2 and ap2-10, F2 plants carrying the recombinant chromosome were selected for kanamycin resistance conferred by the NPT II gene in the T-DNA linked to the AP2 locus (Jofuku et al., 1994, Plant Cell 6, 1211–1225). After identification of the recombinant chromosomes, the order of shr in respect to the marker loci was determined by three-point analyses with flanking markers. Based on the analysis of 148, 112 and 486 chromosomes derived from the mapping crosses, 2, 4 and 1 recombination events were observed between shr-1 and ngal 107, shr-2 and ngal 107 and shr-2 and ap2, respectively. The analysis of the recombinant chromosomes with flanking markers indicated that the SHR locus is on chromosome IV, between markers ap2 (0.2 cM) and ngal 107 (2.62 cM).

6.1.4. Cosegregation Analysis and Inverse PCR

Figure 3A:
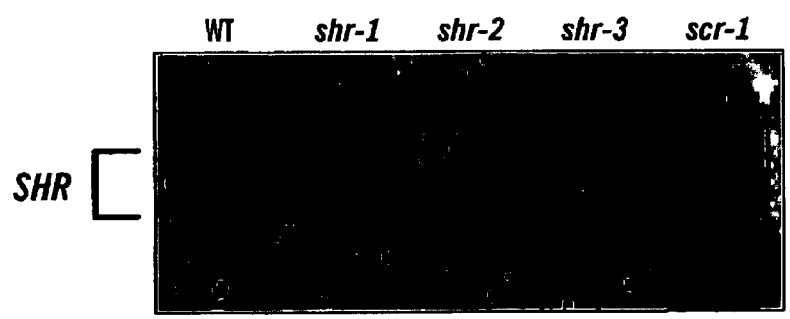

The segregating population representing the progeny of a shr-3 heterozygote was genotyped based on phenotype and a DNA sample was extracted from the same individuals for Southern analysis. An end fragment (generated with oligos: En7631 5'-GGCTCACATCATGCTAGTCC-3' (SEQ ID NO: 10) and En8183 5'-GTTGACCGACACTCTTAGCC-3' (SEQ ID NO: 11)) of the En transposon was used as probe. A band present in all mutants was identified in lanes corresponding to EcoRV digested DNA (FIG. 3a). A band with identical segregation pattern in the population was observed with EcoRI digestion. In this case the fragment size was 2.6 kb, indicating that the plant derived part of the sequence was about 200 bp.

The 2.6 kb EcoRI fragment was isolated from an agarose gel. Inverse PCR was performed (essentially as described by Long et al., 1993, Proc. Natl. Acad. Sci. USA 90, 10370–10374) using En sequences as a basis with primers 5'-TCATACGAATAAGAGCGTCC-3' (fwd) (SEQ ID NO: 12) and 5'-TATTCGCGTCACAATAGTTCC-3' (rev) (SEQ ID NO: 13). An amplification product of approximately 500 bp was obtained, subcloned into a pCRII vector and sequenced.

6.1.5. Sequence Analysis

Sequence of the amplified product was analyzed using the BLAST program (Altschul et al., 1990, J. Mol. Biol. 215, 403410). It was identical to the end sequence of the BAC F 18N2. The 2.8 kb ClaIEcoRI end fragment containing the SHR gene was subcloned into pBluescript (Stratagene) and sequenced. Subsequently the sequence was confirmed by the *Arabidopsis* Genomic Initiative analysis of chromosome IV (Mayer et al., 1999, Nature 402, 769–777).

The SHR gene was amplified from the mutant lines using primers that had been designed based on the wildtype sequence. The shr-2 allele contained an insertion sequence identical to a region from the BAC F2 1117TRB (Accession number; B24674).

6.1.6. Molecular Techniques

RNA gel blot analysis was performed essentially as described (Di Laurenzio et al., 1996, Cell 86, 423–433). A 440 bp fragment representing a region of non-conserved coding region was used as a probe. This probe was also used to screen approximately 150,000 plaques of a cDNA library made from whole seedlings. RT-PCR was performed with M-MLV reverse transcriptase (Promega) according to the manufacturer's protocol on mRNA obtained separately from roots and shoots of 10 day-old seedlings. The two cDNA species and the amplification products from the RT-PCR were subsequently analyzed by sequencing.

The 35S::SHR construct was made by placing the protein-coding region of SHR between the CaMV 35S promoter and the nopaline synthase polyadenylation sequence. The SHR-coding region as well as 31 bp from the 3'UTR were first amplified by PCR with the primers 5'-CAGTCGACT AGTCATATGGATACTCTCTTTAGATTA-3' (SEQ ID NO: 14) and 5'-TGTGGAATTGTGAGCCG-3' (SEQ ID NO: 15) using the 2.8-kb subclone of the SHR genomic region as a template. The former primer removed an Spe I site at codon 7 of SHR, while creating new Spe I and Nde I sites around the first ATG. These mutations did not alter the encoded amino acid sequence. The latter primer was designed to anneal to downstream vector sequence in the template subclone. The PCR amplified DNA fragment was cloned into pCR2.1 (Invitrogen) and sequenced. The SHR-coding region was excised as an Spe I fragment and inserted into the Xba I site of plasmid W104. The resulting plasmid was transformed into *Agrobacterium tumefaciens* (LBA4404) and used to transform wild-type *Arabidopsis* plants (Col) by the floral dipping method (Clough and Bent, 1998, Plant J. 16, 735–743).

6.1.7. Histochemical Techniques and In Situ Hybridization

Histochemical analysis using monoclonal antibodies (JIM13 and CCRC-M2 antibodies) was performed essentially as described (Di Laurenzio et al., 1996, Cell 86, 423–433). For the construction of the SHR promoter::β-glucuronidase (GUS) marker gene line, the 2.5 kb region upstream of the SHR translational start site was amplified by PCR using the primers: 5'-CGGGATCCAGAA GCAGAGCGTGGGGTTTC-3'(fwd) (SEQ ID NO: 16) and 5'-CGGGATCCTTTTAATGAATAAGAAAATG-3' (rev) (SEQ ID NO: 17) (GGATCC BamHI site). The 2.5 kb PCR fragment was inserted into the pCR 2.1 vector using the TA cloning kit (Invitrogen) and, after BamHI digestion, it was subcloned into the BamHI site upstream of the GUS coding region in pBI101 (Clontech). This binary vector was used to generate transgenic plants as described above. T1 seeds were collected in separate pools and transgenic plants were selected by planting on media containing kanamycin (50 µg/ml). GUS staining of the SHR::GUS line was performed as described previously (Malamy and Benfey, 1997, Development 124, 33–44). In situ hybridization analysis was performed essentially as described in Di Laurenzio et al. (1996), Cell 86, 423–433.

6.1.8. GFP Imaging of Gene Expression

The 2.5 kb region upstream of the SHR translational start site was inserted directly upstream of the mGFP5-ER coding region in pBIN, and used to generate transgenic plants as described above. For GFP analysis, roots were counterstained with 10 µg/ml propidium iodide (Sigma) and placed on slides in a drop of water. For analysis in embryos, embryo sacs were dissected from siliques and mounted in $^{50}\!/\!_{\!o}$ glycerol in water. GFP fluorescence was imaged with a Leica confocal microscope, and the FITC channel (green: GFP) was overlaid onto the TRITC channel (red: autofluorescence and propidium iodide) to permit identification of the GFP expressing cells.

6.2. Results

6.2.1. SHORT-ROOT Is Required for Asymmetric Cell Division and Cell Specification in Ground Tissue Previous analysis of two shr alleles (shr-1 and shr-2) had shown that there is only a single cell layer between the epidermis and the pericycle of primary and secondary roots (FIG. 1D) as compared to the normal radial organization of two ground tissue layers, cortex and endodermis (FIG. 1C) (Benfey et al., 1993, Development 119, 57–70; Scheres et al., 1995, Development 121, 53–62). Two additional alleles (shr-3 and shr-4) were identified in a screen of *Arabidopsis* lines containing the autonomous maize En transposon (Wisman et al., 1998, Plant Mol. Biol. 37, 989–999). All four alleles have a similar phenotype—seedlings have highly reduced root growth and darker cotyledons as compared to wildtype (FIG. 1B) (with the exception of some shr-3 and shr-4 roots which contain revertant sectors).

Longitudinal optical sections indicate the presence of a cell at the normal position of the cortex/endodermal initial and no evidence for a periclinal division occurring in its immediate progeny (compare WT and shr in FIGS. 3D and 3G, 5B and 5C). This indicates that a primary defect in shr is disruption of this asymmetric cell division.

Figure 1G:
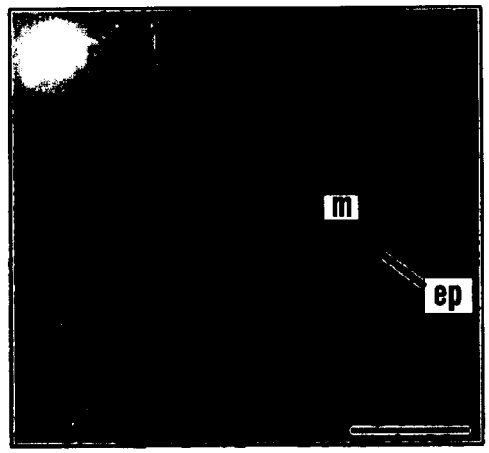
Figure 1H:
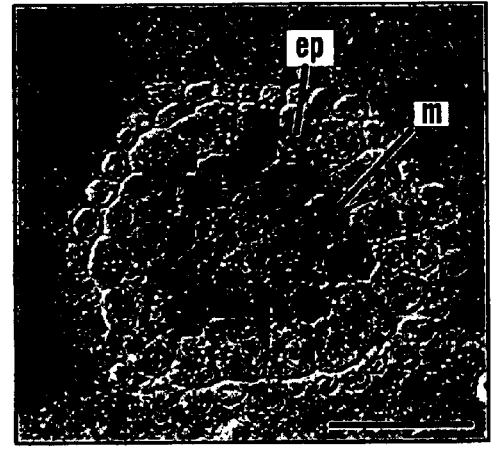

To gain insight into the role of SHR in regulating cell specification, the identity of the single mutant ground tissue cell layer present in shr roots was determined. It had previously shown that two endodermal markers, production of the Casparian strip, and binding of the JIM13 antibody (Knox et al., 1990, Planta 181, 512–521) do not occur in the mutant layer in shr-1 (Scheres et al. 1995, Development 121, 53–62; Benfey et al., 1993, Development 119, 57–70) (compare WT and shr in FIGS. 6B and 6D). Here, the status of two markers normally expressed in the cortex were analyzed. The CCRC-M2 antibody binds to a carbohydrate epitope in the cell walls of epidermis and cortex (Freshour et al., 1996, Plant Physiol. 110, 1413–1429; Di Laurenzio et al., 1996, Cell 86, 423–433). In shr-1, antibody staining is detected in the epidermis as well as the mutant ground tissue layer (compare WT and shr in FIGS. 1E and 1F). Expression of an AX92::GUS construct which is specifically expressed in the root cortex was further tested (Dietrich et al., 1992, Plant Cell 4, 1371–1382; Malamy and Benfey, 1997, Development 124, 33–44). In shr-1, this construct expresses exclusively in the mutant layer (FIGS. 1G and 1H). These results indicate that the shr mutant layer has attributes of cortex and that SHR is necessary for the specification of endodermis cell identity.

6.2.2. Transposon Tagging and Molecular Cloning of SHR

The shr-3 and shr-4 alleles segregated a variable number (5–15%) of seedlings with a wild-type appearance suggesting excision of an En element from the SHR locus. Analysis of the progeny of several putative revertants indicated segregation ratios close to the expected 3:1 (wild type to mutant) consistent with these being heterozygotes. These two alleles were derived from lines that typically harbor more than ten copies of the En transposon (Wisman et al., 1998, Plant Mol. Biol. 37, 989–999). To identify which En element was inserted into the SHR locus, a cosegregation analysis was carried out. A candidate band present in all mutants was identified (FIG. 2A). Inverse PCR amplification was used to identify plant sequences flanking the candidate En element. Comparison to the databases revealed identity to a BAC-end sequence (see Materials and Methods).

Sequence analysis of the BAC revealed an ORF whose deduced amino acid sequence has significant homology to GRAS family genes (FIG. 2 B; Pysh et al., 1999, Plant J. 18, 111–119). To verify the identity of the cloned gene, this region was amplified from shr-1 and shr-2 and sequenced. In shr-1, a deletion of 50 bp towards the 3' end of the ORF results in a frameshift and premature termination of translation of the putative amino acid sequence (FIG. 2C). In shr-2, the full sequence for which is shown in FIG. 10 (SEQ ID NO:3), there is a deletion of 10 bp followed by an insertion of 431 bp (sequence that is identical to a moderately repetitive sequence) towards the 5' end of the ORF (FIG. 2C). This alteration in the DNA sequence would lead to premature termination of the putative peptide. The sites of insertion of the En elements in shr-3 and shr-4 were also determined (FIG. 2C).

Further support for the identity of the cloned gene was obtained by analysis of the segregation of the shr locus-specific En element in the cloned gene in a population of plants representing progeny of a revertant. Excision of the En element cosegregated with the wild type phenotype and no other En elements cosegregated with the mutation. The nature of the molecular defects and the identical phenotype of the four alleles indicates that they are likely to represent the null phenotype.

The protein encoded by the SHR locus would be 531 amino acids in length. FIG. 9 and SEQ ID NO:2. The nucleotide sequence of the *Arabidopsis thaliana* SHR (SEQ ID NO: 1) is shown in FIG. 8. The sequence is from 1 to 2825 base pairs. Further, the mRNA spans 1199 to 2794. All of the motifs found in SCR and the other members of the GRAS gene family (Pysh et al., 1999, Plant J. 18, 111–119) are present in SHR. Unlike SCR, there do not appear to be any introns in the SHR locus.

6.2.3. SHR is Expressed in Stele Tissue

RNA blot analysis revealed two transcripts in wild-type seedlings (FIG. 3A, lane 1). The basis for the two transcripts was investigated by isolation and sequencing of two species of SHR cDNA. The only difference between the two species was in their 3' UTRs in which one species' polyA tail was 109 bp further downstream than the other. Analysis of the 3' genomic UTRs revealed two putative polyadenylation signals positioned 239 bp and 118 bp downstream of the putative termination codon. RT-PCR on either shoot or root tissue confirmed the presence of these two RNA species. These results indicate that the two bands in the RNA blot probably represent transcripts with different polyadenylation sites although additional factors such as different lengths of the polyA tails are possible.

SHR expression was analyzed in three shr alleles. The shr-1 allele has the same level of SHR RNA as wild type (FIG. 3A, lane 2). Transcript levels are severely reduced but still detectable in shr-I (FIG. 3A, lane 3). In shr-3, no transcripts were detected (FIG. 3A, lane 4) which may be the result of the large insertion by the En transposon.

Figure 3B:
Figure 3C:
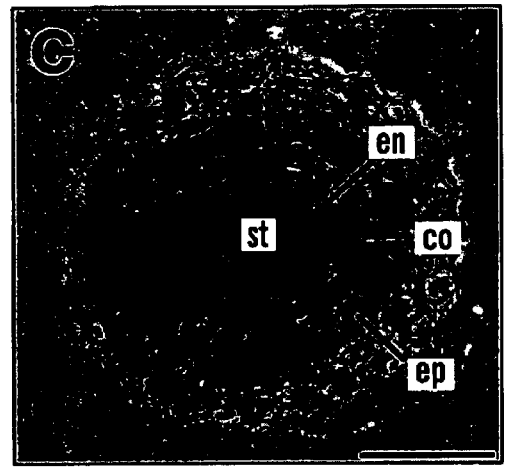
Figure 3D:
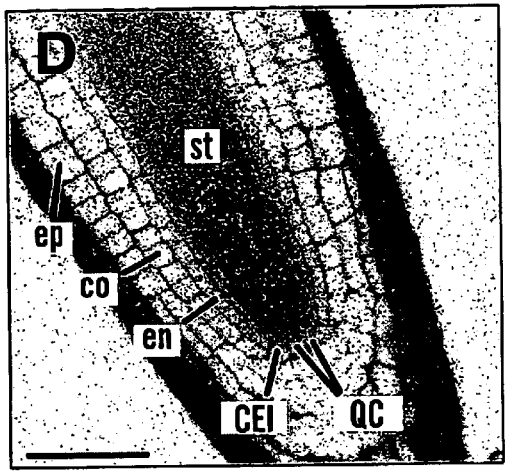
Figure 3E:
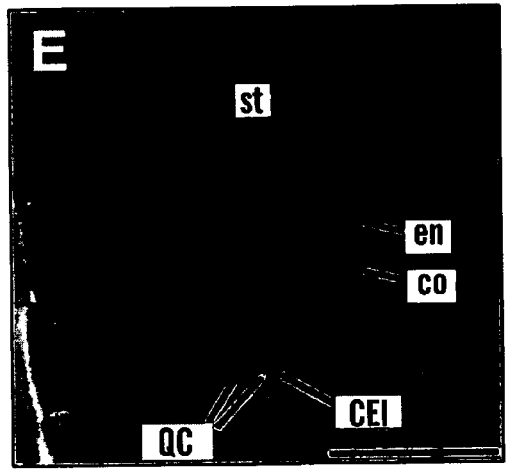
Figure 3F:
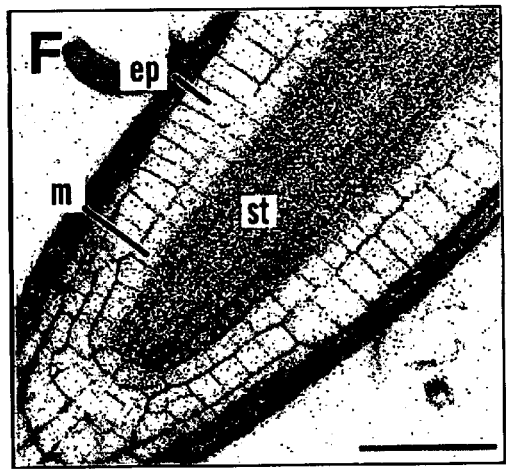
Figure 3G:
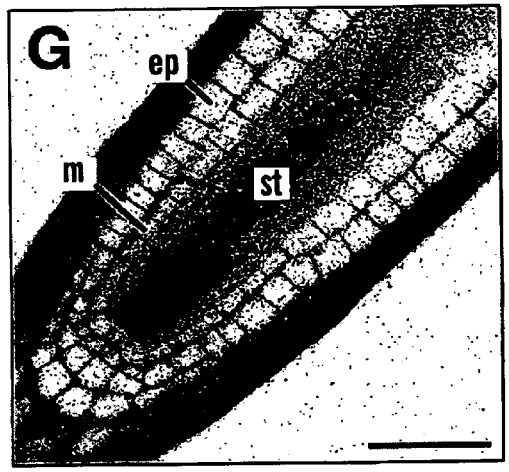

To determine the spatial pattern of SHR expression, RNA in situ hybridization analysis was performed. By in situ hybridization, expression in the root appeared to be primarily in the stele which comprises the central vascular cylinder and the surrounding pericycle (FIGS. 3B and 3C). To determine if the localization of SHR RNA was regulated at the transcriptional or posttranscriptional level, 2.5 kb of 5' upstream sequence was fused to either the Green Fluorescent Protein (GFP) coding region (Haseloff et al. 1997, Proc. Natl. Acad. Sci. USA 94, 2122–2127) or to the GUS coding region. The SHR promoter region conferred expression that was restricted to the stele and extends down to the vascular initial cells (FIGS. 3D and 3E). No SHR expression was ever observed in the ground tissue cell lineage of the root, suggesting that SHR controls radial organization of ground tissue in a non-cell-autonomous manner.

Endodermis and cortex are first formed by an asymmetric cell division of the embryonic ground tissue (Scheres et al., 1995, Development 121, 53–62). It has previously been shown that the shr mutation results in an absence of this asymmetric cell division (Scheres et al., 1995, Development 121, 53–62). The SHR::GFP reporter construct was used to characterize SHR expression at various stages of embryogenesis.

Figure 4A:
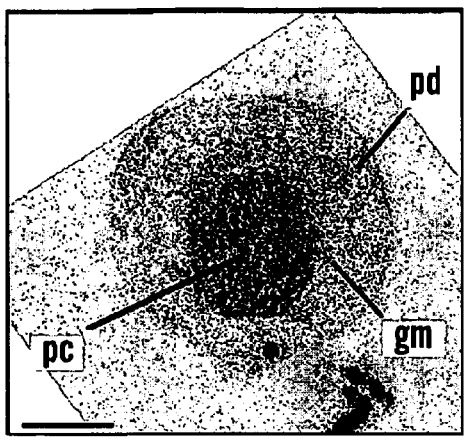
Figure 4B:
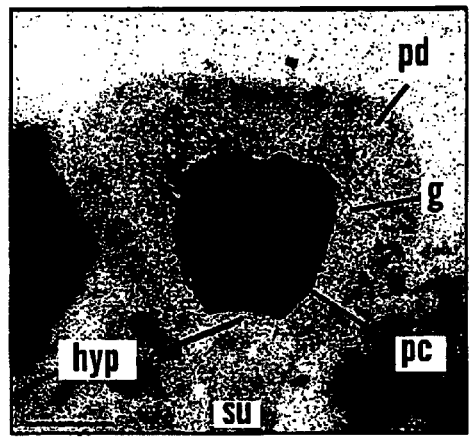
Figure 4C:
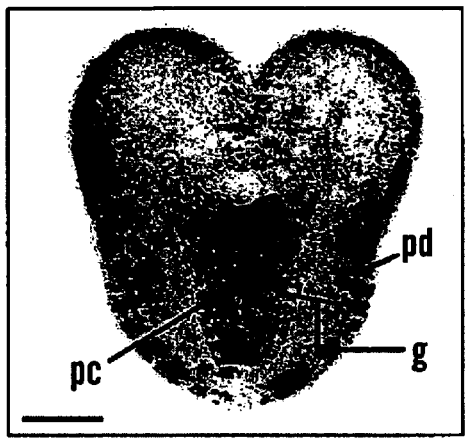
Figure 4D:
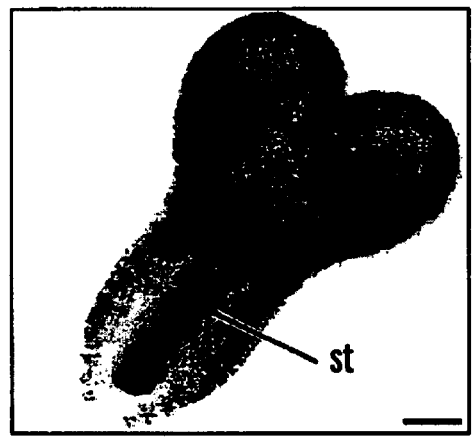
Figure 4E:
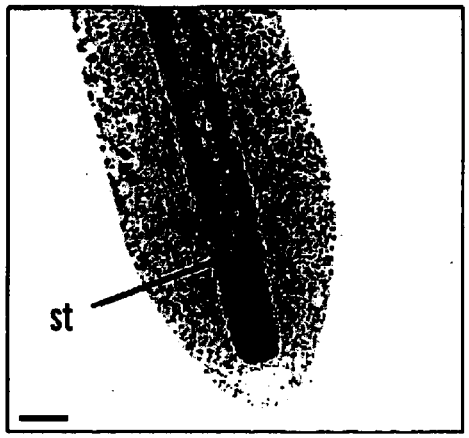
Figure 4F:
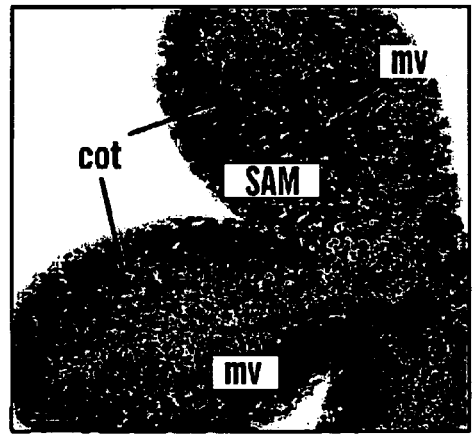

At the late globular stage, SHR::GFP is expressed in procambium cells in the lower tier which is presumptive stele tissue (FIG. 4A). At this stage, SCR is expressed in the ground tissue and hypophysis (Wysocka-Diller et al., 2000, Development 127, 593–603). At the triangular stage, SHR::GFP expression is observed in the procambium (FIG. 4B). SCR expression, at this stage is in the adjacent ground tissue and presumptive center cells (Wysocka-Diller et al., 2000, Development 127, 593–603). SHR::GFP expression in the procambium/stele is consistently observed at later stages of embryogenesis (FIG. 4C, heart stage; FIG. 4D, torpedo stages, FIGS. 4E and 4F, mature embryo). In addition, this expression extends into the cotyledon petiole, in the region of the presumptive cotyledon procambium (FIGS. 4D and 4F). No SHR expression was ever observed in the ground tissue cell lineage or presumptive center cells, consistent with the SHR controlling radial organization of ground tissue in a non-cell-autonomous manner during embryogenesis.

6.2.4. SHR Is a Positive Regulator of SCR Expression

Both SHR and SCR regulate the asymmetric cell division of the endodermis/cortex initial daughter cell and of the embryonic ground tissue. SHR regulates both cell division and endodermis specification, whereas SCR appears to regulate primarily the cell division process. As an initial test to determine whether SHR might be an upstream regulator of SCR in a pathway that results in asymmetric cell division, double mutants were generated and found to have a phenotype identical to shr-1. The epistasis of shr is consistent with the previous findings and argues against a pathway in which SCR would be upstream of SHR.

To determine the relationship between SCR and SHR activity, the effect of the scr mutation on SHR expression was first examined. From RNA blot analysis the level of SHR expression appears to be unaffected by the putative null scr-1 mutation (FIG. 3A, lane 5), indicating that SHR expression is not dependent on SCR activity. To investigate the spatial distribution of SHR expression in scr mutant roots, the SHR::GFP transgene was crossed into scr-3. In scr-3 roots, SHR::GFP expression was still confined to the stele (FIG. 3F), indicating that the establishment of the SHR expression pattern is not dependent on SCR activity. These results are consistent with the observation that the mutant ground tissue layer in scr retains endodermal differentiation attributes (Di Laurenzio et al., 1996, Cell 86, 423–433).

To investigate the possibility that there might be a regulatory relationship at the transcriptional level with SHR upstream of SCR, an RNA blot analysis of SCR expression was performed in the shr background (FIG. 5A). The consistently reduced expression of SCR in the shr mutant background indicates that SHR is essential for normal levels of SCR expression in the root. To investigate the spatial distribution of the remaining SCR expression in shr roots, a SCR::GFP transgene (Wysocka-Diller et al., 2000, Development 127, 593–603) was crossed into shr. In all shr alleles analyzed, the level of GFP expression was dramatically lowered compared to that in wild type (compare FIGS. 5B and 5C). Faint expression in the single ground tissue layer and sometimes in the epidermal layer was observable near the meristematic region. No expression was detected in more differentiated tissue. SHR is, thus, essential for maintenance of SCR expression in the promeristem and in more differentiated root cells. The residual level of SCR expression detected in the shr mutant ground tissue is apparently not sufficient for the correct radial patterning of the ground tissue.

To determine if SHR is involved in an autoregulation pathway, the effect of the shr mutation on SHR expression using shr-1 plants containing the SHR::GFP transgene was examined. In these plants, expression was still restricted to the stele tissue (FIG. 3G) indicating that SHR activity is not necessary for the transcriptional regulation of SHR.

6.2.5. Cell division and Cell Specification are Uncoupled in Somatic Revertant Sectors The genetic instability of the shr-3 allele was used to investigate the relationship between SCR expression, ground tissue cell division and cell specification. Infrequently, shr-3 seedlings develop indeterminate primary or secondary roots. A relatively rare class of putative somatic sector roots are those with mutant cotyledons and an indeterminately growing primary root. These plants were used in the present analysis because the embryonic origins of the primary root are well documented (Mayer et al., 1993, Development 117, 149–162).

Figure 6E:
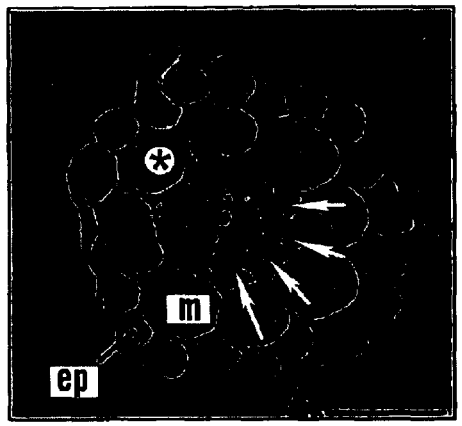
Figure 6F:
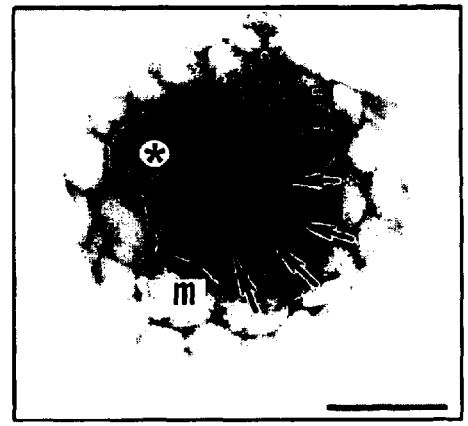
Figure 6G:
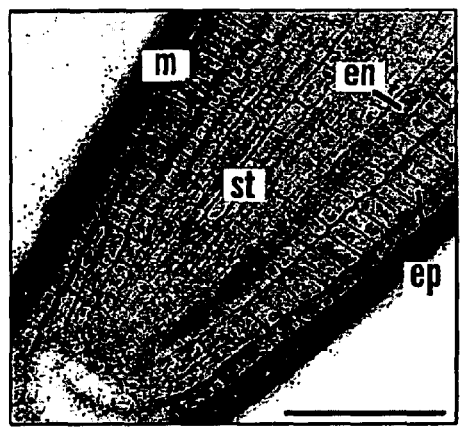
Figure 6H:
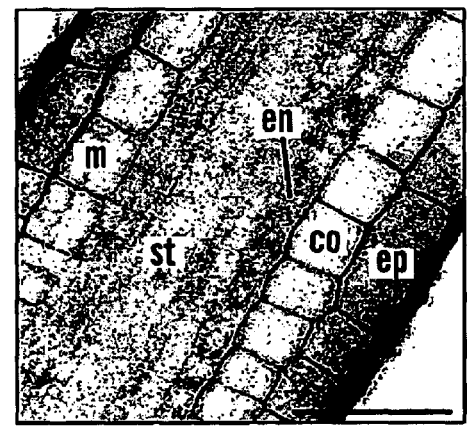

SCR::GFP was crossed into the shr-3 background and seedlings with indeterminate primary roots and mutant cotyledons were visualized by confocal laser scanning microscopy. In all primary revertant roots, a sector of wild-type ground tissue with GFP expression in the inner of the two layers was observed (FIGS. 6G and 6H). This indicates that there is a partial restoration of the wild-type radial pattern. There was complete concordance of longer roots, sectors with divided ground tissue and high-level GFP expression in the inner layer.

To determine the differentiation status of the primary revertant roots scored for SCR::GFP expression, transverse sections were analyzed for the presence of the epitope recognized by the JIM 13 monoclonal antibody (Knox et al., 1990, Planta 181, 512–521; Di Laurenzio et al., 1996, Cell 86, 423–433). In wildtype, the antibody decorates endodermis and some stele cells (FIGS. 6A and 6B), while in shr, antibody binding is restricted to the stele and is excluded from the mutant ground tissue layer (FIGS. 6C and 6D). In sections from partially revertant roots, the ground tissue cells that had divided always expressed this marker (FIGS. 6E and 6F). Occasionally the continuous domain of divided cells was slightly broader than half of the root, although in most cases it was very narrow. Ground tissue cells that had not divided (and did not express SCR::GFP) but were decorated by the antibody also were consistently detected (cell with star in FIGS. 6E and 6F). This indicates that there has been a spatial uncoupling of cell division and cell specification resulting from the partial reversion process.

6.2.6. Ectopic SHR Expression Alters Cell Division and Cell Specification

Figure 7A:
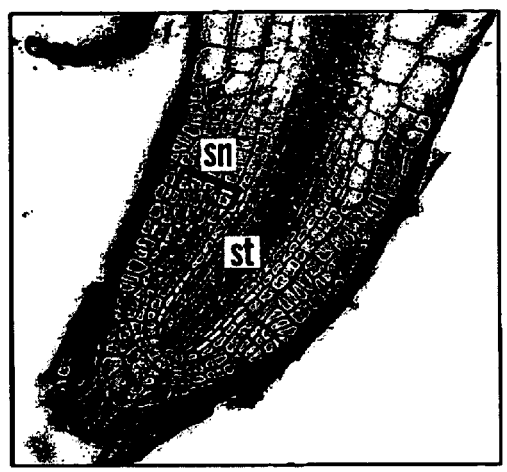
Figure 7B:
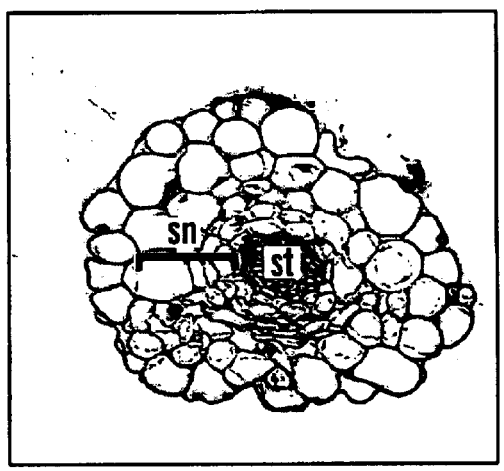

To determine if SHR is sufficient for cell division and cell specification when ectopically expressed, the SHR coding region was placed under the control of the Cauliflower Mosaic virus (CaMV) 35S promoter, which is constitutively active in most plant tissues (Odell et al., 1985, Nature 313, 810–812). Analysis of five independent transformants revealed supernumerary cell layers (from 3 to 7 layers) surrounding the stele in the seedling root (FIGS. 7A and 7B). The number of extra layers varied among the different independent lines and among progeny from a single line and the radial pattern was not always symmetric in the root. In all lines the stele appeared similar to wild type. In longitudinal optical sections it appeared that the additional cell layers were the result of extra cell divisions that originated in the root meristem (FIG. 7A).

Figure 7C:
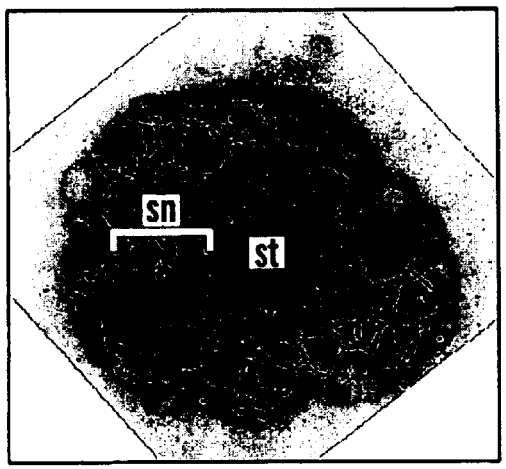

To determine if ectopic SHR expression affects cell specification, root sections from 35S::SHR seedlings were stained with the JIM13 antibody. Staining was observed in most of the supernumerary cells in addition to the stele and presumptive endodermis (FIG. 7C).

Figure 7D:
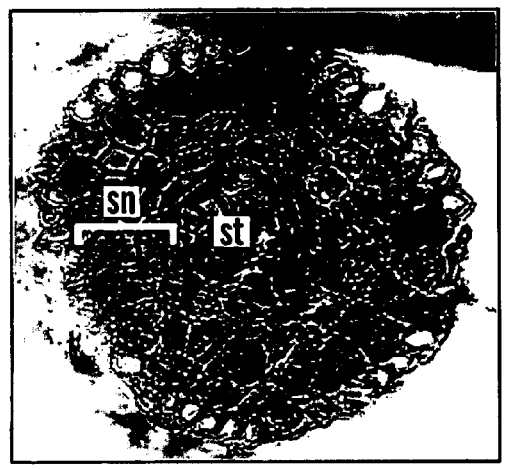
Figure 7E:
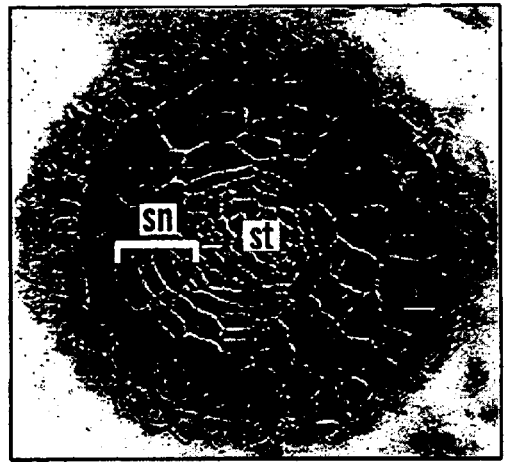

To determine the spatial localization of SHR expression and its affect on SCR expression, in situ hybridizations were performed on root tissue from 35S::SHR seedlings. As would be expected with expression driven by the 35S promoter, SHR RNA appeared to be in all tissues (except possibly in the external root cap cells) (FIG. 7D). In the meristematic zone of wildtype roots, SCR is expressed very specifically in the endodermis (Di Laurenzio et al. 1996, Cell 86, 423–433; Pysh et al., 1999, Plant J. 18, 111–119). In the meristematic zone of 35S::SHR roots, SCR expression appeared to be in all tissues except for the stele and the root cap. The ectopic expression of SCR in the 35S::SHR plants is consistent with the hypothesis that SHR is upstream of SCR in a pathway that leads to transcriptional activation of SCR. Taken together these results indicate that ectopic SHR expression causes extra cell divisions and alters cell specification in the root meristem.

6.2.7. SHR Promoter Cloning and Characterization

To determine if the SHR promoter is capable of driving tissue specific expression, a SHR promoter-glucocorticoid receptor translational fusion (SHR-GR) and a SHR promoter-green fluorescent protein translational fusion (SHR-GFP) were made. The sequence of the SHR promoter used in the experiments is shown at FIG. 11 (SEQ ID NO:4). As depicted in the figure, the sequence is from 1 to 2502 base pairs. A schematic showing the structure of the SHR-GR and the SHR-GFP is shown at FIG. 12A. The methods by which the SHR-GR and the SHR-GFP were made are shown schematically in FIGS. 12B–12D.

Experiments with these constructs demonstrated that dexamethasone applied to short-root mutant plants that have the SHR-GR transgene causes complete rescue of the root phenotype, i.e., restoration of the endodermal layer. The SHR-GFP construct is also able to rescue short-root mutant plants. This indicates that a SHR promoter fragment is able to rescue the root phenotype similar to the native promoter.

6.2.8. SHR Coding Sequence Driven by SCR Promoter

To determine if the SCR promoter is capable of driving tissue specific expression of a SHR coding sequence, a construct containing the SCR promoter upstream of the SHR coding sequence was prepared. Briefly, wildtype, *Arabidopsis* plants (ecotype Columbia) were transformed with the plasmid pBIH-SCRprom-SHR by the floral dip method. A schematic showing the method by which the plasmid was prepared is shown in FIG. 13. After obtaining transformants, the T2 progeny were analyzed. Observation of transverse sections revealed nine layers of cell files between the stele and epidermis in both hypocotyl and root of the transformants, in place of the normal three and two layers in the wildtype hypocotyl and root, respectively. These ectopic cell layers were found to have endodermal characteristics, as determined by suberin staining which detects the casparian strip and by the JIM 13 antibody which detects an arabinogalactan epitope in some of the ectopic cell layers.

Moreover, transgenic plants containing the SCR promoter-SHR transgene demonstrate additional cell divisions only in the ground tissue (the tissue between the external epidermis and the vascular cylinder), which is where the SCR promoter is active.

FIG. 14 shows the results of attaching the promoter region from the SCR gene to the SHR coding sequence. In contrast to the ectopic cell divisions found throughout the outer layers of the root when the SHR gene is driven by the constitutive 35S promoter (left), with the SCR promoter, ectopic divisions appear to be restricted to the ground tissue (right) (the $2^{nd}$ and $3^{rd}$ layers in from the outside of the root. FIG. 15 shows cross-sections of hypocotyl and root comparing wildtype plants and SCR promoter-SHR transgenic plants. Note that there are up to nine layers where, normally, there are only two between the epidermis and the stele. FIG. 16 shows staining for the Casparian strip. Note that in wildtype plants, the Casparian strip is found only in the endodermis, while in the SCR promoter-SHR transgenic plants, there is evidence for additional Casparian strip in the supernumerary layers. Because the Casparian strip functions to impede water flow from the external environment to the vascular tissue of the plant allowing for selective uptake of solutes, the ability to direct specifically the formation of the Casparian strip could be beneficial in drought tolerance, etc.

6.3. Discussion

6.3.1. SHR Is a New Member of the GRAS Family of Putative Transcription Factors The deduced amino acid sequence of SHORT-ROOT places it in the GRAS gene family, whose founding member is SCARECROW (Di Laurenzio et al., 1996, Cell 86, 423–433; Pysh et al., 1999, Plant J. 18, 111–119). Motifs including homopolymeric repeat regions, leucine heptad repeats, and putative nuclear localization signals found in all members of this family raised the possibility that they act as transcription factors. Nuclear localization of at least one member of the family (RGA) has been demonstrated. (Silverstone et al., 1998, Plant Cell 10, 155–169). Moreover, it has been suggested that within the C-terminus of some GRAS family proteins is a region similar to the SH2 domain of STAT proteins (Peng et al., 1999, Nature 400, 256–261).

In addition to SCR and SHR, a third member of the GRAS family has been shown to be a possible regulator of radial patterning. The expression pattern of SHR is restricted to the endodermis in the root (Pysh et al., 1999, Plant J. 18, 111–119). This indicates that there is a subfamily of GRAS genes that participate in radial patterning.

Another subfamily of GRAS genes which is involved in gibberellic acid signaling has been shown to share a conserved domain (Peng et al., 1997, Genes & Dev. 11, 3194–3205; Silverstone et al., 1998, Plant Cell 10, 155–169). No conserved domain that might be specific to GRAS genes involved in radial patterning was found in a comparison of SCR and SHR to other members of the family.

6.3.2. SHR is Upstream of SCR

Previously, it had been shown that shr does not express endodermal markers in the root (Benfey et al., 1993, Development 119, 57–70; Scheres et al., 1995, Development 121, 53–62). The use of cortex markers revealed that the remaining ground tissue layer has differentiated attributes of cortex. From this, it can be concluded that SHR is required for both the asymmetric cell division that generates cortex and endodermis and for endodermal specification. Because SCR has been shown to regulate primarily the same asymmetric cell division, it was hypothesized that SHR might function upstream of SCR in a common pathway. The epistasis of shr to scr was consistent with this hypothesis as was the down-regulation of SCR RNA expression in a shr background.

Because SHR is a putative transcription factor, the simplest scenario was that SHR interacts directly with the SCR promoter. The expectation then was that SHR would be expressed in the precursor cells of the ground tissue. By in situ hybridization and promoter::marker gene expression, SHR expression is not detectable in the ground tissue lineage. Rather it appears to be expressed exclusively in stele cells. Because the root radial pattern is established during embryogenesis, it was possible that SHR was first expressed in the embryonic ground tissue and then became restricted to stele tissue after germination. The present analysis of embryonic expression was not consistent with this hypothesis. On the contrary, SHR expression was found only in the precursors to the stele.

Expression of SHR in the stele suggested that it might play a role in development of this tissue. However, all cell types present in the wild-type stele appear to be present in shr indicating that if there is a phenotype it is subtle.

6.3.3. SHR Participates in Radial Signaling

The fact that SHR is required for ground tissue patterning and transcriptional regulation of SCR but is not expressed in ground tissue cells indicates that it may act in a non-cell autonomous manner. A trivial explanation would be that SHR expression in the ground tissue is just below detection limits. Analysis of revertant sectors in primary roots of the unstable shr-3 allele which harbors the SCR::GFP construct was not consistent with this hypothesis. In these plants, partial restoration of a two-layer ground tissue was found, with the inner layer expressing GFP and binding the JIM 13 antibody. Moreover, ground tissue cells that had not divided, did not express GFP but did bind JIM 13 were found. Because this combination of marker expression was found in many roots, it is highly unlikely that this is due to multiple reversion events.

The simplest explanation of the partial reversion events, consistent with the fate map of Arabidopsis embryo (Mayer et al., 1993, Development 117, 149–162; Scheres et al., 1994, Development 120, 2475–2487), is that reversion results in SHR expression in a subset of stele cells. The first division in the embryo proper always occurs vertically before the horizontal divisions that separate the root and shoot poles. This would indicate that the excision event in plants with revertant roots and mutant cotyledons must have taken place after the first vertical division which would result in, at most, reversion of half of the root tissue.

In this hypothesis, there are different effects on neighboring ground tissue cells depending on their proximity to the revertant tissue. This suggests that either SHR regulates differentiation and the asymmetric cell division by two signals with distinct radial mobility or that one process has a higher sensitivity to the radially moving signal than the other process.

Two alternatives for the non-cell-autonomous regulation of SCR expression by SHR are possible. First, it is possible that the SHR gene product is present only in the stele cells where it is expressed. In this scenario, SHR would regulate SCR expression through an intermediate that moves from the stele to the ground tissue cell lineage. Alternatively, the SHR protein itself might be transported via plasmodesmata from the stele to the ground tissue cell lineage. The latter scenario is supported by evidence that the maize knotted 1 transcription factor can move from one cell lineage to another (Lucas et al., 1995, Science 270, 1980–1983).

The phenotype of 35S::SHR roots supports the finding that SHR is a positive regulator of root radial patterning. The presence of supernumerary cell layers and altered cell specification in the extra cell layers strongly suggests that SHR is both necessary and sufficient for cell division and cell specification in the root meristem.

6.3.4. Three-Dimensional Cell Communication in the Root Meristem

The present results concerning the non-cell autonomous mode of interaction of SHR with SCR provide new insight into how positional information related to patterning is distributed in the plant meristem. Recently, the role of vascular tissue as a source of positional information has been demonstrated in the context of auxin signaling in organizing the distal pattern of the root (Sabatini et al., 1999, Cell 99, 463–472). SHR-mediated radial patterning of the ground tissue provides further evidence for the role of vascular tissue as playing an important role in organizing plant organogenesis.

For the cortex/endodermal initial cell of the root meristem, van den Berg et al (1995, Nature 378, 62–65; 1997, Nature 390, 287–289) have shown that a "top-down" signal is essential for the asymmetric division of its immediate daughter cell, and that another contact dependent signal from the underlying quiescent center is essential for the maintenance of the undifferentiated status of the initial. The present invention now identifies a new radial signaling pathway, which regulates the asymmetric division of the immediate daughter cell of the initial through the SHR and SCR genes. This indicates the presence of a three-dimensional signaling network, which controls the developmental status of the initial cell and its derivatives.

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

All publications, patents and patent applications mentioned in this specification are herein incorporated by reference to the same extent as if each individual publication, patent or patent application was specifically and individually indicated to be incorporated by reference.

What is claimed is:

1. A transgenic plant comprising a transgene comprising a nucleic acid of interest operatively associated with a SHORT-ROOT promoter, said promoter comprising the nucleic acid sequence of SEQ ID NO:4, wherein said promoter functions to promote stele-specific expression in roots and embryos of the plant.

2. The transgenic plant of claim 1, in which the nucleic acid of interest encodes a gene product that confers herbicide, salt, pathogen, or insect resistance.

3. A transgenic plant comprising a transgene comprising a nucleic acid of interest operatively associated with a SHORT-ROOT promoter, said promoter comprising the nucleic acid sequence of SEQ ID NO:4, wherein said promoter functions to promote stele-specific expression in shoots of the plant.

4. The transgenic plant of claim 3, in which the nucleic acid of interest encodes a gene product that increases starch, lignan or cellulose biosynthesis.

5. The plant of claim 1, wherein said nucleic acid of interest is a SHORT-ROOT nucleic acid.

* * * * *